(12) United States Patent
Zhou et al.

(10) Patent No.: US 9,387,200 B2
(45) Date of Patent: Jul. 12, 2016

(54) ISOTHIAZOLE-PYRIDINE DERIVATIVES AS MODULATORS OF HIF (HYPOXIA INDUCIBLE FACTOR) ACTIVITY

(71) Applicant: FibroGen, Inc., San Francisco, CA (US)

(72) Inventors: Xiaoti Zhou, Burlingame, CA (US); Michael P. Arend, Foster City, CA (US); Min Wu, Sunnyvale, CA (US); Lee A. Flippin, Woodside, CA (US)

(73) Assignee: FibroGen, Inc., San Francisco, CA (US)

( * ) Notice: Subject to any disclaimer, the term of this patent is extended or adjusted under 35 U.S.C. 154(b) by 0 days.

(21) Appl. No.: 14/609,216

(22) Filed: Jan. 29, 2015

(65) Prior Publication Data

US 2015/0209336 A1 Jul. 30, 2015

Related U.S. Application Data

(62) Division of application No. 12/811,821, filed as application No. PCT/US2009/030775 on Jan. 12, 2009, now Pat. No. 8,952,160.

(60) Provisional application No. 61/020,665, filed on Jan. 11, 2008.

(51) Int. Cl.
| A61K 31/437 | (2006.01) |
|---|---|
| C07D 513/04 | (2006.01) |
| A61K 31/497 | (2006.01) |
| A61K 45/06 | (2006.01) |

(52) U.S. Cl.
CPC ............. *A61K 31/437* (2013.01); *A61K 31/497* (2013.01); *A61K 45/06* (2013.01); *C07D 513/04* (2013.01)

(58) Field of Classification Search
CPC ................................. A61K 31/4439
See application file for complete search history.

(56) References Cited

U.S. PATENT DOCUMENTS

| 7,323,475 B2 | 1/2008 | Arend et al. |
|---|---|---|
| 7,618,940 B2 | 11/2009 | Fourney et al. |
| 7,629,357 B2 | 12/2009 | Arend et al. |
| 7,696,223 B2 | 4/2010 | Deng et al. |
| 7,713,986 B2 | 5/2010 | Seeley et al. |
| 8,269,008 B2 | 9/2012 | Arend et al. |
| 8,324,405 B2 | 12/2012 | Ho et al. |
| 8,952,160 B2 | 2/2015 | Zhou et al. |
| 2003/0153503 A1 | 8/2003 | Klaus et al. |
| 2003/0176317 A1 | 9/2003 | Guenzler-Pukall et al. |
| 2004/0204356 A1 | 10/2004 | Guenzler-Pukall et al. |
| 2005/0020487 A1 | 1/2005 | Klaus et al. |
| 2006/0178316 A1 | 8/2006 | Klaus et al. |
| 2006/0183695 A1 | 8/2006 | Klaus et al. |
| 2006/0199836 A1 | 9/2006 | Turtle et al. |
| 2006/0258660 A1 | 11/2006 | Guenzler-Pukall et al. |
| 2006/0258702 A1 | 11/2006 | Guenzler-Pukall et al. |
| 2006/0270699 A1 | 11/2006 | Guenzler-Pukall et al. |
| 2006/0276477 A1 | 12/2006 | Klaus et al. |
| 2007/0004627 A1 | 1/2007 | Seeley et al. |
| 2007/0155784 A1 | 7/2007 | Arend et al. |
| 2007/0185159 A1 | 8/2007 | Arend et al. |
| 2007/0293575 A1 | 12/2007 | Seeley et al. |
| 2007/0298104 A1 | 12/2007 | Arend et al. |
| 2008/0004309 A1 | 1/2008 | Deng et al. |
| 2008/0293763 A1 | 11/2008 | Arend et al. |
| 2010/0047367 A1 | 2/2010 | Deng et al. |

FOREIGN PATENT DOCUMENTS

| WO | WO 02/074981 | 9/2002 |
|---|---|---|
| WO | WO 03/049686 | 6/2003 |
| WO | WO 03/053997 | 7/2003 |
| WO | WO 03/080566 | 10/2003 |
| WO | WO 2004/052284 | 6/2004 |

(Continued)

OTHER PUBLICATIONS

Edwards et. al. Molecular genetics of AMD and current animal models. Angiogenesis 2007 10:119-132.*
Campochiaro "The Complexity of Animal Model Generation for Complex Diseases" JAMA, Feb. 17, 2010—vol. 303, No. 7 657-658.*
Ford "Liver disease related to the heart" Transplantation Reviews 29 (2015) 33-37.*

(Continued)

*Primary Examiner* — David K. O'Dell
(74) *Attorney, Agent, or Firm* — Leanne C. Price; Sheppard Mullin Richter & Hampton LLP

(57) ABSTRACT

The present invention relates to novel compounds according to Formula I or II, methods, and compositions capable of decreasing HIF hydroxylase enzyme activity, thereby increasing the stability and/or activity of hypoxia inducible factor (HIF). Formula (I) or (II).

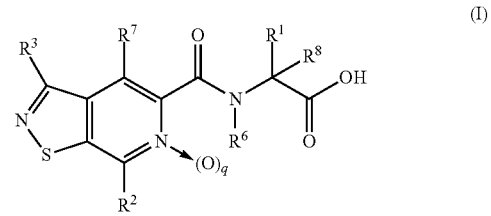

(I)

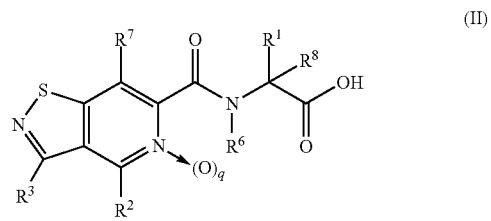

(II)

17 Claims, No Drawings

(56) References Cited

FOREIGN PATENT DOCUMENTS

| WO | WO 2004/052285 | 6/2004 |
|---|---|---|
| WO | WO 2004/108121 | 12/2004 |
| WO | WO 2004/108681 | 12/2004 |
| WO | WO 2005/007192 | 1/2005 |
| WO | WO 2006/094292 | 9/2006 |
| WO | WO 2006/133391 | 12/2006 |
| WO | WO 2006/138511 | 12/2006 |
| WO | WO 2007/025169 | 3/2007 |
| WO | WO 2007/038571 | 4/2007 |
| WO | WO 2007/070359 | 6/2007 |
| WO | WO 2007/090068 | 8/2007 |
| WO | WO 2007/103905 | 9/2007 |
| WO | WO 2007/115315 | 10/2007 |
| WO | WO 2007/136990 | 11/2007 |
| WO | WO 2007/146425 | 12/2007 |
| WO | WO 2007/146438 | 12/2007 |
| WO | WO 2007/150011 | 12/2007 |
| WO | WO 2008/076425 | 6/2008 |
| WO | WO 2008/076427 | 6/2008 |
| WO | WO 2008/089051 | 7/2008 |
| WO | WO 2008/089052 | 7/2008 |
| WO | WO 2008/130508 | 10/2008 |
| WO | WO 2008/130600 | 10/2008 |
| WO | WO 2008/137060 | 11/2008 |
| WO | WO 2008/137084 | 11/2008 |
| WO | WO 2009/039321 | 3/2009 |
| WO | WO 2009/039322 | 3/2009 |
| WO | WO 2009/039323 | 3/2009 |
| WO | WO 2009/049112 | 4/2009 |
| WO | WO 2009/070644 | 6/2009 |
| WO | WO 2009/073497 | 6/2009 |
| WO | WO 2009/073669 | 6/2009 |
| WO | WO 2009/075822 | 6/2009 |
| WO | WO 2009/075826 | 6/2009 |
| WO | WO 2009/086044 | 7/2009 |
| WO | WO 2009/089547 | 7/2009 |
| WO | WO 2010/022240 | 2/2010 |
| WO | WO 2010/056767 | 5/2010 |

OTHER PUBLICATIONS

Rabinowitz "Inhibition of Hypoxia-Inducible Factor Prolyl Hydroxylase Domain Oxygen Sensors: Tricking the Body into Mounting Orchestrated Survival and Repair Responses" J. Med. Chem. 2013, 56, 9369-9402.*

Bishop "HIF Hydroxylase Pathways in Cardiovascular Physiology and Medicine" Circulation Research Jun. 19, 2015, 65-79.*

Arjamaa "Regulatory role of HIF-1a in the pathogenesis of age-related macular degeneration (AMD)" Ageing Research Reviews 8 (2009) 349-358.*

Wolff, Manfred E. "Burger's Medicinal Chemistry and Drug Discovery, 5ed, Part I", John Wiley & Sons, 1995, pp. 975-977.

Banker (Modern Pharmaceutics) Banker, G.S. et al, "Modern Pharmaceutics, 3ed.", Marcel Dekker, New York, 1996, pp. 451 and 596.

Baldwin et. al. "Heterocyclic Analogues of the Antihypertensive β-Adrenergic Blocking Agent (5)-2-[3-(*tert*-Butylamino)-2hydroxypropoxy]-3-Cyanopyridine" J. Med. Chem. 1980, 23, 65-70.

Bruegge, K. et al., "Hydroxylation of Hypoxia-Inducible Transcription Factors and Chemical Compounds Targeting the HIF-alpha Hydroxylases," Current Medicinal Chemistry, vol. 14, pp. 1853-1862, XP002517838 (2007).

Wermuth, C.G., "Molecular Variants Based on Isosteric Replacements," The Practice of Medicinal Chemistry, Elsevier, pp. 189-214, XP009112544 (2003).

International Search Report and Written Opinion for PCT/US2009/030775, dated Mar. 31, 2009, 10 pages.

* cited by examiner

ISOTHIAZOLE-PYRIDINE DERIVATIVES AS MODULATORS OF HIF (HYPOXIA INDUCIBLE FACTOR) ACTIVITY

CROSS-REFERENCE TO RELATED APPLICATION

This application is a divisional application of U.S. patent application Ser. No. 12/811,821, filed Sep. 14, 2010, which application is a National Phase application under 35 U.S.C. §371 of PCT Application PCT/US2009/030775, filed Jan. 12, 2009, which application claims priority benefit under 35 U.S.C. §119(e) to U.S. Provisional Application No. 61/020,665, filed Jan. 11, 2008, which applications are hereby incorporated by reference in their entirety.

BACKGROUND OF THE INVENTION

1. Field of the Invention

The present invention relates to novel compounds, methods, and compositions capable of decreasing HIF hydroxylase enzyme activity, thereby increasing the stability and/or activity of hypoxia inducible factor (HIF).

2. State of the Art

Hypoxia inducible factor (HIF) is a basic helix-loop-helix (bHLH) PAS (Per/Arnt/Sim) transcriptional activator that mediates changes in gene expression in response to changes in cellular oxygen concentration. HIF is a heterodimer containing an oxygen-regulated α-subunit (HIFα), and a constitutively expressed β-subunit (HIFβ/ARNT). In oxygenated (normoxic) cells, HIFα subunits are rapidly degraded by a mechanism that involves ubiquitination by the von Hippel-Lindau tumor suppressor (pVHL) E3 ligase complex. Under hypoxic conditions, HIFα is not degraded, and an active HIFα/β complex accumulates in the nucleus, and activates the expression of several genes including glycolytic enzymes, glucose transporters, erythropoietin (EPO), and vascular endothelial growth factor (VEGF). (Jiang et al. (1996) *J. Biol. Chem.* 271:17771-17778; Iliopoulus et al. (1996) *Proc. Natl. Acad. Sci. USA,* 93:10595-10599; Maxwell et al. (1999) *Nature* 399:271-275; Sutter et al. (2000) *Proc. Natl. Acad. Sci. USA* 97:4748-4753; Cockman et al. (2000) *J. Biol. Chem.* 275:25733-25741; and Tanimoto et al. (2000) *EMBO J.* 19:4298-4309.)

Levels of HIFα are elevated in most cells in response to hypoxia, and HIFα is induced in vivo when animals are subjected ischemia or hypoxia, or develop anemia. The increase in HIFα levelsleads to formation of HIFα/β complexes. HIFα/β complexes induce numerous beneficial cellular processes including cytoprotective effects, enhanced erythropoiesis, and physiological adaptation to ischemic or hypoxic states. Induction of HIFα is potentially beneficial in conditions such as myocardial infarction, stroke, peripheral vascular disease, chronic ischemia, inflammation, and anemia.

HIFα levels can be increased by a number of factors that mimic hypoxia, including iron chelators such as desferrioxamine (DFO), and divalent metal salts such as $CoCl_2$. Additionally, several compounds originally identified as inhibitors of procollagen prolyl hydroxylase enzymes have been found to stabilize HIFα. Examples of such compounds can be found, e.g., in Majamaa et al. (1984) *Eur. J. Biochem.* 138:239-245; Majamaa et al. (1985) *Biochem. J.* 229:127-133; Kivirikko, and Myllyharju (1998) *Matrix Biol.* 16:357-368; Bickel et al. (1998) *Hepatology* 28:404-411; Friedman et al. (2000) *Proc. Natl. Acad. Sci. USA* 97:4736-4741; Franklin (1991) *Biochem. Soc. Trans.* 19):812-815; and Franklin et al. (2001) *Biochem. J.* 353:333-338. Additionally, compounds that stabilize HIFα have been described in, e.g., International Publication Nos. WO 03/049686, WO 02/074981, WO 03/080566, WO 2004/108681, WO 06/094292, WO 07/038571, WO 07/090068, and WO 07/103905.

There remains a need for compounds that are effective in the treatment and prevention of conditions and disorders associated with HIF, including anemia, and tissue damage caused by ischemia and/or hypoxia. The compounds provided herein modulate HIF and can be used to treat and prevent HIF-associated conditions and disorders including conditions involving anemia, ischemia, and hypoxia.

SUMMARY OF THE INVENTION

The present invention is directed to novel compounds and methods of using these compounds to modulate hydroxylation of the alpha subunit of hypoxia inducible factor.

In one aspect, there are provided compounds of Formula I or II:

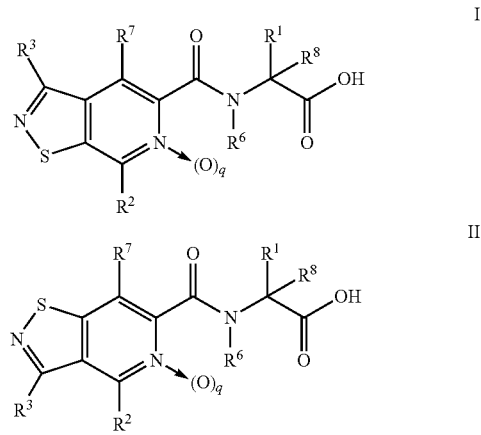

wherein
q is 0 or 1;
$R^1$ is selected from the group consisting of hydrogen, deuterium, alkyl, and substituted alkyl;
$R^2$ is selected from the group consisting of hydrogen, hydroxyl, halo, cyano, alkyl, substituted alkyl, alkenyl, substituted alkenyl, alkynyl, substituted alkynyl, alkoxy, substituted alkoxy, cycloalkyl, substituted cycloalkyl, cycloalkoxy, substituted cycloalkoxy, amino, substituted amino, aminoacyl, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyloxy, substituted heterocyclyloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, and acyl;
$R^3$ is selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, aryl, substituted aryl, aryloxy, substituted aryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl;

R⁶ is selected from the group consisting of hydrogen, alkyl, and substituted alkyl;

R⁷ is selected from the group consisting of hydroxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, thio, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, amino, substituted amino, and acylamino; and R⁸ is selected from the group consisting of hydrogen, deuterium, and methyl;

or a pharmaceutically acceptable salt, single stereoisomer, mixture of stereoisomers, ester, or prodrug thereof.

In one embodiment, there are provided compounds of Formula III or IV:

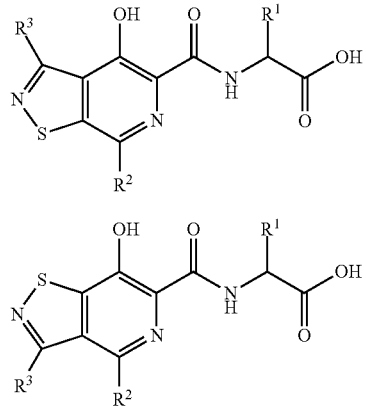

wherein

R¹ is hydrogen or alkyl;

R² is selected from the group consisting of
  hydrogen,
  hydroxyl,
  bromo,
  cyano,
  alkyl such as C1-C4 alkyl, for example, methyl, ethyl, propyl, or butyl,
  substituted alkyl wherein alkyl is substituted with one or more of halo, hydroxyl, cyano, or phenyl,
  alkynyl such as ethynyl,
  aryl such as phenyl or naphthalenyl,
  substituted aryl wherein aryl is substituted with one or more of cyano, hydroxyl, halo such as fluoro, or alkoxy such as methoxy, or phenoxy,
  heteroaryl such as a 6-membered heteroaryl, for example, pyridinyl, or pyrazinyl,
  substituted heteroaryl such as a 6-membered substituted heteroaryl, for example, substituted pyridinyl substituted with hydroxyl or alkoxy, and
  acyl such as acetyl; and R³ is selected from the group consisting of
  alkyl such as C1-C4 alkyl, for example, methyl, ethyl or propyl,
  substituted alkyl wherein alkyl is substituted with a heteroaryl such as a bicyclic heteroaryl for example, indolyl,
  aryl such as phenyl, and
  substituted aryl wherein aryl is substituted with one or more of a halo such as fluoro or chloro, cyano, hydroxyl, or alkoxy;

or a pharmaceutically acceptable salt, single stereoisomer, mixture of stereoisomers, ester, or prodrug thereof.

The invention also provides pharmaceutical compositions comprising one or more compounds of Formula I, II, III, or IV, and a pharmaceutically acceptable excipient. In some embodiments, the composition further comprises at least one additional therapeutic agent. In some embodiments, the agent is selected from the group consisting of vitamin $B_{12}$, folic acid, ferrous sulfate, recombinant human erythropoietin, and an erythropoiesis stimulating agent (ESA).

The invention is also directed to methods of treating, pretreating, or delaying onset or progression of a condition associated with or mediated, at least in part, by hypoxia inducible factor (HIF), the method comprising administering to a patient a therapeutically effective amount of a compound of Formula I, II, III, or IV, or a pharmaceutical composition comprising one or more compounds of Formula I, II, III, or IV. In one embodiment, the condition associated with or mediated by HIF is tissue damage associated with ischemia or hypoxia. In one aspect, the ischemia is associated with an acute event including, but not limited to, an acute event selected from the group consisting of myocardial infarction, pulmonary embolism, intestinal infarction, ischemic stroke, and renal ischemic-reperfusion injury. In another aspect, the ischemia is associated with a chronic event including, but not limited to, a chronic event selected from the group consisting of cardiac cirrhosis, transient ischemic attack, macular degeneration, chronic kidney failure, peripheral artery disease, and congestive heart failure.

The invention is also directed to methods of treating, pretreating, or delaying onset or progression of a condition associated with or mediated, at least in part, by erythropoietin (EPO), the method comprising administering to a patient a therapeutically effective amount of a compound of Formula I, II, III, or IV, or a pharmaceutical composition comprising one or more compounds of Formula I, II, III, or IV.

The invention is also directed to methods of treating, pretreating, or delaying onset or progression of anemia, the method comprising administering to a patient a therapeutically effective amount of a compound of Formula I, II, III, or IV, or a pharmaceutical composition comprising one or more compounds of Formula I, II, III, or IV.

The invention is also directed to methods of inhibiting the activity of at least one HIF hydroxylase enzyme, the method comprising bringing into contact the HIF hydroxylase enzyme and a compound of the invention. In one embodiment, the HIF hydroxylase enzyme is an asparaginyl hydroxylase such as Factor Inhibiting HIF (FIH). In another embodiment, the HIF hydroxylase enzyme is a prolyl hydroxylase including, but not limited to, a HIF prolyl hydroxylase selected from the group consisting of human EGLN1, EGLN2, or EGLN3, or an orthologous enzyme from another species.

DETAILED DESCRIPTION OF THE INVENTION

Before the present compositions and methods are described, it is to be understood that the invention is not limited to the particular compounds, compositions, methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

1. Compounds of the Invention

The invention is directed to compounds of Formula I or II:

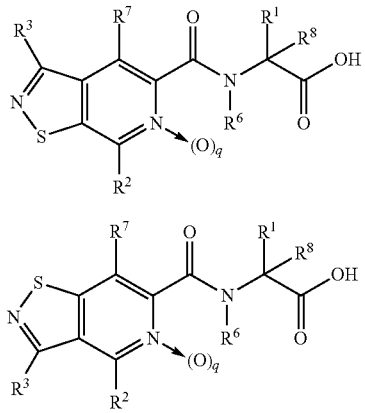

wherein q is 0 or 1;

$R^1$ is selected from the group consisting of hydrogen, deuterium, alkyl, and substituted alkyl;

$R^2$ is selected from the group consisting of hydrogen, hydroxyl, halo, cyano, alkyl, substituted alkyl, alkenyl, substituted alkenyl, alkynyl, substituted alkynyl, alkoxy, substituted alkoxy, cycloalkyl, substituted cycloalkyl, cycloalkoxy, substituted cycloalkoxy, amino, substituted amino, aminoacyl, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyloxy, substituted heterocyclyloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, and acyl;

$R^3$ is selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, aryl, substituted aryl, aryloxy, substituted aryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl;

$R^6$ is selected from the group consisting of hydrogen, alkyl, and substituted alkyl;

$R^7$ is selected from the group consisting of hydroxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, thio, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, amino, substituted amino, and acylamino; and $R^8$ is selected from the group consisting of hydrogen, deuterium, and methyl;

or a pharmaceutically acceptable salt, single stereoisomer, mixture of stereoisomers, ester, or prodrug thereof In certain embodiments, q is 0.

In certain embodiments, $R^1$ is hydrogen or alkyl. In particular embodiments, $R^1$ is methyl.

In certain embodiments, $R^2$ is selected from the group consisting of hydrogen, hydroxyl, halo, cyano, alkyl, substituted alkyl, alkynyl, aryl, substituted aryl, heteroaryl, substituted heteroaryl, and acyl. In particular embodiments, $R^2$ is selected from the group consisting of hydrogen, hydroxyl, bromo, cyano, methyl, ethyl, benzyl, trifluoromethyl, ethynyl, phenyl, naphthalene-1-yl, 4-cyanophenyl, 4-fluorophenyl, 3-methoxyphenyl, 4-methoxyphenyl, 4-phenoxyphenyl, pyrid-2-yl, pyrid-3-yl, pyrid-4-yl, pyrazin-2-yl, 6-methoxypyridin-3-yl, 1-benzyl-1H-[1,2,3]triazol-4-yl, and acetyl.

In certain embodiments, substituted alkyl for $R^2$ is benzyl or trifluoromethyl.

In certain embodiments, substituted aryl for $R^2$ is 4-cyanophenyl, 4-fluorophenyl, 3-methoxyphenyl, 4-methoxyphenyl, or 4-phenoxyphenyl.

In certain embodiments, substituted heteroaryl for $R^2$ is 6-methoxypyridin-3-yl or 1-benzyl-1H-[1,2,3]triazol-4-yl.

In certain embodiments, $R^3$ is alkyl, substituted alkyl, aryl or substituted aryl. In particular embodiments, the $R^3$ is methyl, indol-1-ylmethyl, phenyl, 2-fluorophenyl, 4-fluorophenyl, or 4-chlorophenyl.

In certain embodiments, substituted alkyl for $R^3$ is indol-1-ylmethyl.

In certain embodiments, substituted aryl for $R^3$ is 2-fluorophenyl, 4-fluorophenyl, or 4-chlorophenyl.

In some embodiments, $R^6$ and $R^8$ are hydrogen.

In some embodiments, $R^7$ is hydroxy. In particular embodiments wherein $R^7$ is hydroxy, $R^1$, $R^6$ and $R^8$ are all hydrogen. In other embodiments wherein $R^7$ is hydroxy, $R^1$ is methyl and $R^6$ and $R^8$ are hydrogen.

In certain embodiments, the invention relates to compounds of Formula I or II wherein $R^1$ is hydrogen or alkyl;

$R^6$ and $R^8$ are hydrogen;

$R^2$ is selected from the group consisting of hydrogen, hydroxyl, halo, cyano, alkyl, substituted alkyl, alkynyl, aryl, substituted aryl, heteroaryl, substituted heteroaryl, and acyl;

$R^3$ is alkyl, substituted alkyl, aryl or substituted aryl; and $R^7$ is hydroxy.

In certain embodiments, the invention relates to compounds of Formula I or II wherein $R^1$ is hydrogen or methyl;

$R^6$ and $R^8$ are hydrogen;

$R^2$ is selected from the group consisting of hydrogen, hydroxyl, bromo, cyano, methyl, ethyl, benzyl, trifluoromethyl, ethynyl, phenyl, naphthalene-1-yl, 4-cyanophenyl, 4-fluorophenyl, 3-methoxyphenyl, 4-methoxyphenyl, 4-phenoxyphenyl, pyrid-2-yl, pyrid-3-yl, pyrid-4-yl, pyrazin-2-yl, 6-methoxypyridin-3-yl, 1-benzyl-1H-[1,2,3]triazol-4-yl, and acetyl;

$R^3$ is methyl, indol-1-ylmethyl, phenyl, 2-fluorophenyl, 4-fluorophenyl, or 4-chlorophenyl; and $R^7$ is hydroxy.

In one embodiment, there are provided compounds of Formula III or IV:

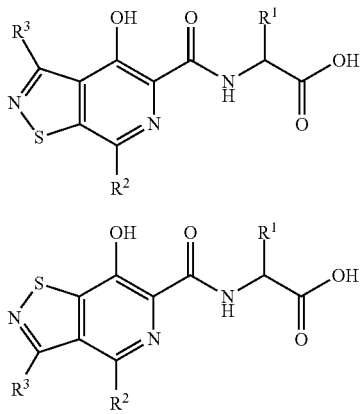

wherein
R¹ is hydrogen or alkyl;
R² is selected from the group consisting of
hydrogen,
hydroxyl,
bromo,
cyano,
alkyl such as C1-C4 alkyl, for example, methyl, ethyl, propyl, or butyl,
substituted alkyl wherein alkyl is substituted with one or more of halo, hydroxyl, cyano, or phenyl,
alkynyl such as ethynyl,
aryl such as phenyl or naphthalenyl,
substituted aryl wherein aryl is substituted with one or more of cyano, hydroxyl, halo such as fluoro, or alkoxy such as methoxy, or phenoxy,
heteroaryl such as a 6-membered heteroaryl, for example, pyridinyl, or pyrazinyl,
substituted heteroaryl such as a 6-membered substituted heteroaryl, for example, substituted pyridinyl substituted with hydroxyl or alkoxy, and
acyl such as acetyl; and
R³ is selected from the group consisting of
alkyl such as C1-C4 alkyl, for example, methyl, ethyl or propyl,
substituted alkyl wherein alkyl is substituted with a heteroaryl such as a bicyclic heteroaryl for example, indolyl,
aryl such as phenyl, and
substituted aryl wherein aryl is substituted with one or more of a halo such as fluoro or chloro, cyano, hydroxyl, or alkoxy;
or a pharmaceutically acceptable salt, single stereoisomer, mixture of stereoisomers, ester,
or prodrug thereof.

Compounds of the invention include, but are not limited to, {[7-(4-Fluoro-phenyl)-4-hydroxy-3-phenyl-isothiazolo[5,4-c]pyridine-5-carbonyl]-amino}-acetic acid; {[4-Hydroxy-7-(4-methoxy-phenyl)-3-phenyl-isothiazolo[5,4-c]pyridine-5-carbonyl]-amino}-acetic acid; [(4-Hydroxy-3-phenyl-7-pyridin-3-yl-isothiazolo[5,4-c]pyridine-5-carbonyl)-amino]-acetic acid; [(4-Hydroxy-3-phenyl-7-pyridin-2-yl-isothiazolo[5,4-c]pyridine-5-carbonyl)-amino]-acetic acid; [(4-Hydroxy-3-phenyl-7-pyridin-4-yl-isothiazolo[5,4-c]pyridine-5-carbonyl)-amino]-acetic acid; {[7-Ethynyl-3-(4-fluoro-phenyl)-4-hydroxy-isothiazolo[5,4-c]pyridine-5-carbonyl]-amino}-acetic acid; {[7-Bromo-3-(4-fluoro-phenyl)-4-hydroxy-isothiazolo[5,4-c]pyridine-5-carbonyl]-amino}-acetic acid; {[7-Cyano-3-(4-fluoro-phenyl)-4-hydroxy-isothiazolo[5,4-c]pyridine-5-carbonyl]-amino}-acetic acid; {[3-(4-Fluoro-phenyl)-4-hydroxy-7-methyl-isothiazolo[5,4-c]pyridine-5-carbonyl]-amino}-acetic acid; {[3-(4-Fluoro-phenyl)-4-hydroxy-7-phenyl-isothiazolo[5,4-c]pyridine-5-carbonyl]-amino}-acetic acid; {[7-(4-Cyano-phenyl)-3-(4-fluoro-phenyl)-4-hydroxy-isothiazolo[5,4-c]pyridine-5-carbonyl]-amino}-acetic acid; {[3-(4-Fluoro-phenyl)-4-hydroxy-isothiazolo[5,4-c]pyridine-5-carbonyl]-amino}-acetic acid; {[3-(4-Chloro-phenyl)-4-hydroxy-7-(4-methoxy-phenyl)-isothiazolo[5,4-c]pyridine-5-carbonyl]-amino}-acetic acid; {[3-(4-Chloro-phenyl)-7-ethynyl-4-hydroxy-isothiazolo[5,4-c]pyridine-5-carbonyl]-amino}-acetic acid; {[3-(4-Chloro-phenyl)-4-hydroxy-7-methyl-isothiazolo[5,4-c]pyridine-5-carbonyl]-amino}-acetic acid; {[3-(4-Chloro-phenyl)-4-hydroxy-isothiazolo[5,4-c]pyridine-5-carbonyl]-amino}-acetic acid; {[3-(4-Chloro-phenyl)-4-hydroxy-7-phenyl-isothiazolo[5,4-c]pyridine-5-carbonyl]-amino}-acetic acid; (R)-2-{[3-(4-Chloro-phenyl)-4-hydroxy-isothiazolo[5,4-c]pyridine-5-carbonyl]-amino}-propionic acid; (S)-2-{[3-(4-Chloro-phenyl)-4-hydroxy-isothiazolo[5,4-c]pyridine-5-carbonyl]-amino}-propionic acid; {[3-(4-Chloro-phenyl)-4-hydroxy-7-(3-methoxy-phenyl)-isothiazolo[5,4-c]pyridine-5-carbonyl]-amino}-acetic acid; {[3-(4-Chloro-phenyl)-4-hydroxy-7-(6-methoxy-pyridin-3-yl)-isothiazolo[5,4-c]pyridine-5-carbonyl]-amino}-acetic acid; {[7-Benzyl-3-(4-chloro-phenyl)-4-hydroxy-isothiazolo[5,4-c]pyridine-5-carbonyl]-amino}-acetic acid; { [7-(1-Benzyl-1H-[1,2,3]triazol-4-yl)-3-(4-chloro-phenyl)-4-hydroxy-isothiazolo[5,4-c]pyridine-5-carbonyl]-amino}-acetic acid; {[3-(4-Chloro-phenyl)-4-hydroxy-7-naphthalen-1-yl-isothiazolo[5,4-c]pyridine-5-carbonyl]-amino}-acetic acid; {[7-Acetyl-3-(4-chloro-phenyl)-4-hydroxy-isothiazolo[5,4-c]pyridine-5-carbonyl]-amino}-acetic acid; {[3-(4-Chloro-phenyl)-4-hydroxy-7-trifluoromethyl-isothiazolo[5,4-c]pyridine-5-carbonyl]-amino}-acetic acid; [(4-Bromo-7-hydroxy-3-phenyl-isothiazolo[4,5-c]pyridine-6-carbonyl)-amino]-acetic acid; [(4-Hydroxy-3,7-dimethyl-isothiazolo[5,4-c]pyridine-5-carbonyl)-amino]-acetic acid; [(7-Hydroxy-3,4-dimethyl-isothiazolo[4,5-c]pyridine-6-carbonyl)-amino]-acetic acid; [(4-Hydroxy-3-methyl-7-phenyl-isothiazolo[5,4-c]pyridine-5-carbonyl)-amino]-acetic acid; [(7-Hydroxy-3-methyl-4-phenyl-isothiazolo[4,5-c]pyridine-6-carbonyl)-amino]-acetic acid; [(7-Hydroxy-3-methyl-isothiazolo[4,5-c]pyridine-6-carbonyl)-amino]-acetic acid; {[3-(2-Fluoro-phenyl)-4-hydroxy-isothiazolo[5,4-c]pyridine-5-carbonyl]-amino}-acetic acid; {[3-(2-Fluoro-phenyl)-4-hydroxy-7-phenyl-isothiazolo[5,4-c]pyridine-5-carbonyl]-amino}-acetic acid; {[3-(2-Fluoro-phenyl)-4-hydroxy-7-(4-phenoxy-phenyl)-isothiazolo[5,4-c]pyridine-5-carbonyl]-amino}-acetic acid; {[3-(2-Fluoro-phenyl)-4-hydroxy-7-methyl-isothiazolo[5,4-c]pyridine-5-carbonyl]-amino}-acetic acid; [(4-Hydroxy-3-methyl-7-pyridin-3-yl-isothiazolo[5,4-c]pyridine-5-carbonyl)-amino]-acetic acid; [(4-Hydroxy-3-methyl-7-pyridin-2-yl-isothiazolo[5,4-c]pyridine-5-carbonyl)-amino]-acetic acid; [(7-Ethynyl-4-hydroxy-3-methyl-isothiazolo[5,4-c]pyridine-5-carbonyl)-amino]-acetic acid; [(4-Hydroxy-3-methyl-7-pyrazin-2-yl-isothiazolo[5,4-c]pyridine-5-carbonyl)-amino]-acetic acid; [(7-Hydroxy-3-methyl-4-pyrazin-2-yl-isothiazolo[4,5-c]pyridine-6-carbonyl)-amino]-acetic acid; [(7-Hydroxy-3-indol-1-ylmethyl-4-phenyl-isothiazolo[4,5-c]pyridine-6-carbonyl)-amino]-acetic acid; [(4-Hydroxy-3-phenyl-isothiazolo[5,4-c]pyridine-5-carbonyl)-amino]-acetic acid; [(4-Hydroxy-7-methyl-3-phenyl-isothiazolo[5,4-c]pyridine-5-carbonyl)-amino]-acetic acid; [(4-Hydroxy-3,7-diphenyl-isothiazolo[5,4-c]pyridine-5-carbonyl)-amino]-acetic acid;

[(7-Ethyl-4-hydroxy-3-methyl-isothiazolo[5,4-c]pyridine-5-carbonyl)-amino]-acetic acid; and [(4-Ethyl-7-hydroxy-3-methyl-isothiazolo[4,5-c]pyridine-6-carbonyl)-amino]-acetic acid, or a pharmaceutically acceptable salt, single stereoisomer, mixture of stereoisomers, ester, or prodrug thereof.

2. Compositions and Methods of the Invention

The invention provides for use of a compound of Formula I, II, III or IV, for the manufacture of a medicament for use in treating various conditions or disorders as described herein. In one embodiment, a pharmaceutical composition or medicament is provided comprising at least one compound of Formula I, II, III or IV and a pharmaceutically acceptable excipient or carrier.

In various embodiments, the medicament or pharmaceutical composition can further comprise at least one additional therapeutic agent. In one embodiment, the agent is selected from the group consisting of vitamin $B_{12}$, ferrous sulfate, folic acid, and/or recombinant erythropoietin or an erythropoiesis stimulating agent (ESA).

The compounds of the present invention, or medicaments or compositions comprising the compounds, can be used to decrease HIF hydroxylase enzyme activity, thereby modulating the stability and/or activity of HIF, and activating HIF-regulated gene expression. The compound, or composition or medicament thereof, can be used in methods to treat, pretreat, or delay progression or onset of conditions mediated at least in part by HIF, including, but not limited to, anemia and various aspects of ischemic and hypoxic conditions. In various embodiments, the compound is administered immediately following an acute condition producing ischemia, e.g., myocardial infarction, pulmonary embolism, intestinal infarction, ischemic stroke, acute respiratory failure, renal ischemic-reperfusion injury, etc. In another embodiment, the compound, or composition or medicament thereof, is administered to a patient diagnosed with a chronic condition associated with the development of ischemia, e.g., cardiac cirrhosis, macular degeneration, neonatal respiratory distress syndrome, peripheral artery disease, chronic kidney failure, congestive heart failure, etc. In yet another embodiment, the compound, or composition or medicament thereof, is administered immediately after a trauma or injury. In other embodiments, the compound, or composition or medicament thereof, can be administered to a subject based on predisposing conditions, e.g., hypertension, diabetes, occlusive arterial disease, chronic venous insufficiency, Raynaud's disease, chronic skin ulcers, cirrhosis, congestive heart failure, transient ischemic attack, and systemic sclerosis. In still other embodiments, compounds may be administered to a subject to decrease or prevent the development of tissue damage associated with ischemia or hypoxia.

The compounds of the present invention, or compositions or medicaments thereof, can also be used to increase endogenous erythropoietin (EPO). The compounds, or composition or medicament thereof, can be administered to prevent, pretreat, or treat EPO-associated conditions, including, e.g., conditions associated with anemia and neurological disorders. In one embodiment, the compounds of the present invention, or compositions or medicaments thereof, can be used to treat, pretreat, or delay onset of anemia, such as anemia that may develop in association with various conditions or disorders. Conditions associated with anemia include disorders such as acute or chronic kidney disease, diabetes, cancer, ulcers, infection with virus, e.g., HIV, bacteria, or parasites; inflammation, etc. Anemic conditions can further include those associated with procedures or treatments including, e.g., radiation therapy, chemotherapy, dialysis, anesthesia, and surgery. Disorders associated with anemia additionally include abnormal hemoglobin and/or erythrocytes, such as found in disorders such as microcytic anemia, hypochromic anemia, aplastic anemia, etc.

The compounds can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Additionally, the compounds can be used to increase endogenous EPO levels in an anemic or non-anemic patient scheduled to undergo surgery to reduce the need for allogenic blood transfusions or to facilitate banking of blood prior to surgery.

The invention is also directed to a method of inhibiting the activity of at least one hydroxylase enzyme which modifies the alpha subunit of hypoxia inducible factor. The HIF hydroxylase enzyme may be an asparaginyl hydroxylase such as Factor Inhibiting HIF (FIH). The HIF hydroxylase enzyme may be a prolyl hydroxylase including, but not limited to, a prolyl hydroxylase selected from the group consisting of EGLN1, EGLN2, and EGLN3. In one embodiment, the method comprises contacting the hydroxylase enzyme with an effective amount of one or more compounds selected from the group comprising compounds of Formula I, II, III, or IV.

3. Definitions

It must be noted that as used herein, and in the appended claims, the singular forms "a," "an," and "the" include plural references unless the context clearly dictates otherwise.

Unless defined otherwise, all technical, and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology, and pharmacology, within the skill of the art. Such techniques are explained fully in the literature. (See, e.g., Gennaro, A. R., ed. (1990) Remington's Pharmaceutical Sciences, 18$^{th}$ ed., Mack Publishing Co.; Colowick, S. et al., eds., Methods In Enzymology, Academic Press, Inc.; D. M. Weir, and C. C. Blackwell, eds. (1986) Handbook of Experimental Immunology, Vols. I-IV, Blackwell Scientific Publications; Maniatis, T. et al., eds. (1989) Molecular Cloning: A Laboratory Manual, 2$^{nd}$ edition, Vols. I-III, Cold Spring Harbor Laboratory Press; Ausubel, F. M. et al., eds. (1999) Short Protocols in Molecular Biology, 4$^{th}$ edition, John Wiley & Sons; Ream et al., eds. (1998) Molecular Biology Techniques: An Intensive Laboratory Course, Academic Press; Newton & Graham eds. (1997) PCR (Introduction to Biotechniques Series), 2nd ed., Springer Verlag).

The term "HIFα" refers to the alpha subunit of hypoxia inducible factor protein. HIFα may be any human or other mammalian protein, or fragment thereof, including, but not limited to, human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130, and AAB41496), and HIF-3α (Genbank Accession No. AAC72734); rat HIF-1α (Genbank Accession No. CAA70701), HIF-2α (Genbank Accession No. CAB96612), and HIF-3α (Genbank Accession No. CAB96611); and bovine HIF-1α (Genbank Accession No. BAA78675), HIF-2α (GenBank Accession No. BAA78676), and HIF-3α (Genbank Accession No. NP 001098812). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1α (Genbank Accession No. BAA34234).

A fragment of HIFα includes any fragment retaining at least one functional or structural characteristic of HIFα. Fragments of HIFα include, e.g., the regions defined by human HIF-1α from amino acids 401 to 603 (Huang et al., supra), amino acid 531 to 575 (Jiang et al. (1997) *J. Biol. Chem.* 272:19253-19260), amino acid 556 to 575 (Tanimoto et al., supra), amino acid 557 to 571 (Srinivas et al. (1999) *Biochem. Biophys. Res. Commun.* 260:557-561), and amino acid 556 to 575 (Ivan and Karlin (2001) *Science* 292:464-468). Further, HIFα fragments include any fragment containing at least one occurrence of the motif LXXLAP, e.g., such as occurs in the human HIF-1α native sequence from $L_{397}$ to $P_{402}$, and from $L_{559}$ to $P_{564}$.

The terms "HIF-associated conditions" and "conditions mediated at least in part by HIF" are used inclusively and refer to any condition that can be associated with below normal, abnormal, or inappropriate modulation of HIF. HIF-associated conditions include any condition wherein an increase in HIF level would provide therapeutic benefit. HIF-associated conditions include anemic conditions and tissue damage or disorders associated with ischemic or hypoxic conditions.

The term "HIF hydroxylase" refers to any enzyme that modifies the alpha subunit of HIF by hydroxylation of one or more amino acid residues. HIF hydroxylases include Factor Inhibiting HIF (FIH) (GenBank Accession AAL27308; Mahon et al. (2001) *Genes Dev.* 15:2675-2686; Lando et al. (2002) *Science* 295:858-861; and Lando et al. (2002) *Genes Dev.* 16:1466-1471, which modifies at least one asparagine residue found within HIFα. (Also, see, Elkins et al. (2002) *J. Biol. Chem.* C200644200.) HIF hydroxylases also include HIF prolyl hydroxylases (HIF PHs), each of which modifies at least one proline residue found within HIFα.

The terms "HIF prolyl hydroxylase" and "HIF PH" refer to any enzyme that modifies the alpha subunit of HIF protein by hydroxylation of one or more proline residues. Preferably, the proline residue hydroxylated by HIF PH includes the proline found within the motif LXXLAP. HIF PH includes members of the Egl-Nine (EGLN) gene family described by Taylor (2001, *Gene* 275:125-132), and characterized by Aravind, and Koonin (2001, Genome Biol 2: RESEARCH 0007), Epstein et al. (2001, *Cell* 107:43-54), and Bruick and McKnight (2001, *Science* 294:1337-1340). HIF PH2, as used in examplary assays described herein (infra), may be any HIF PH2, e.g., human EGLN1 (GenBank Accession No. AAG33965; Dupuy et al. (2000) *Genomics* 69:348-54), mouse EGLN1 (GenBank Accession No. CAC42515), rat EGLN1 (GenBank Accession No. P59722), etc. Alternatively, another HIF PH may be used in the assay. Such HIF PH enzymes include, but are not limited to, human EGLN2 isoform 1 (GenBank Accession No. CAC42510; Taylor, supra), human EGLN2 isoform 3 (GenBank Accession No. NP_542770), mouse EGLN2 (GenBank Accession No. CAC42516), and rat EGLN2 (GenBank Accession No. AA046039); and human EGLN3 (GenBank Accession No. AA046039); and human EGLN3 (GenBank Accession No. CAC42511; Taylor, supra), mouse EGLN3 (GenBank Accession No. CAC42517), and rat EGLN3 (SM-20) (GenBank Accession No. AAA19321). In other embodiments of the present invention, EGLN may include *Caenorhabditis elegans* EGL-9 (GenBank Accession No. AAD56365) and *Drosophila melanogaster* CG1114 gene product (GenBank Accession No. AAF52050). HIF PH also includes any fragment of the foregoing full-length proteins that retains at least one structural or functional characteristic.

The term "ischemia" refers to a deficient supply of blood to a cell, tissue, organ, etc. Ischemia is associated with a reduction in nutrients, including oxygen, delivered to tissues. Ischemia may arise due to conditions such as atherosclerosis, formation of a thrombus in an artery or vein, blockage of an artery or vein by an embolus, vascular closure due to other causes, e.g., vascular spasm, etc. Such conditions may reduce blood flow, producing a state of hypoperfusion to an organ or tissue, or block blood flow completely. Other conditions that can lead to ischemia include tissue damage due to trauma or injury, such as, e.g., spinal cord injury; viral infection, which can lead to, e.g., congestive heart failure, etc. The term "ischemic condition" refers to conditions or events that are associated with or result in ischemia. Such conditions or events may be acute or chronic. An acute event that is associated with or results in ischemia may include, but is not limited to, an event selected from the group consisting of myocardial infarction, ischemic stroke, pulmonary embolism, perinatal hypoxia, circulatory shock including, e.g., hemorrhagic, septic, cardiogenic, etc., mountain sickness, acute respiratory failure, etc.; intestinal infarction, acute kidney failure, renal ischemia reperfusion injury, etc. A chronic event that is associated with or results in ischemia may include, but is not limited to, an event selected from the group consisting of atherosclerosis, chronic venous insufficiency, congestive heart failure, cardiac cirrhosis, diabetes, macular degeneration, sleep apnea, Raynaud's disease, systemic sclerosis, nonbacterial thrombotic endocarditis, occlusive artery disease, angina pectoris, transient ischemic attacks (TIAs), chronic alcoholic liver disease, chronic kidney failure, peripheral vascular disorders, ulcers, burns, chronic wounds etc. Ischemia can also result when individuals are placed under general anesthesia, and can cause tissue damage in organs prepared for transplant.

The terms "hypoxia" and "hypoxic" refer to an environment with levels of oxygen below normal. The term "hypoxic condition" includes, but is not limited to, ischemic conditions (ischemic hypoxia) such as those listed above, wherein hypoxia results from reduced circulation; pulmonary disorders (hypoxic hypoxia) such as COPD, severe pneumonia, pulmonary edema, pulmonary hypertension, hyaline membrane disease, and the like, wherein hypoxia results from reduced oxygenation of the blood in the lungs; anemic conditions (anemic hypoxia) such as gastric or duodenal ulcers, liver or renal disease, thrombocytopenia or blood coagulation disorders, cancer or other chronic illness, cancer chemotherapy and other therapeutic interventions that produce anemia, and the like, wherein hypoxia results from a decreased concentration of hemoglobin or red blood cells; and altitude sickness, etc.

The term "anemia" as used herein refers to any abnormality or deficiency in hemoglobin or erythrocytes that leads to reduced oxygen levels in the blood. Anemia can be associated with abnormal production, processing, or performance of erythrocytes and/or hemoglobin. The term anemia refers to any reduction in the number of red blood cells and/or in the level of hemoglobin in blood relative to normal blood levels.

The term "anemic condition" refers to any condition, disease, or disorder associated with anemia. Anemia can arise due to various conditions, for example, acute or chronic kidney disease, infections, inflammation, cancer, irradiation, toxins, diabetes, and surgery. Infections may be due to, e.g., virus, bacteria, and/or parasites, etc. Inflammation may be due to infection or autoimmune disorders, such as rheumatoid arthritis, etc. Anemia can be associated with blood loss due to, e.g., stomach ulcers, duodenal ulcers, hemorrhoids, cancer of the stomach or large intestine, trauma, injury, surgical procedures, etc. Anemia can develop in association with radiation therapy, chemotherapy, and kidney dialysis. Anemia can also develop in HIV-infected patients undergoing treatment with azidothymidine (zidovudine) or other reverse transcriptase inhibitors, and can develop in cancer patients undergoing chemotherapy, e.g., with cyclic cisplatin- or non-cisplatin-containing chemotherapeutics. Aplastic anemia and myelodysplastic syndromes are diseases associated with bone marrow failure which results in decreased production of erythrocytes. Further, anemia can result from defective or abnormal hemoglobin or erythrocytes, such as in disorders including microcytic anemia, hypochromic anemia, etc. Anemia can result from disorders in iron transport, processing, and utilization, see, e.g., sideroblastic anemia, etc.

The terms "disorders," "diseases," and "conditions" are used inclusively herein and refer to any condition deviating from normal.

The terms "erythropoietin" and "EPO" refer to any naturally occurring, recombinant, or synthetic erythropoietin, erythropoiesis stimulating protein (ESP), or erythropoiesis stimulating agent (ESA) including, e.g., human erythropoietin (GenBank Accession No. AAA52400; Lin et al. (1985) Proc. Nat'l. Acad. Sci. USA 82:7580-7584), EPOETIN human recombinant erythropoietin (Amgen, Inc., Thousand Oaks Calif.), ARANESP human recombinant erythropoietin (Amgen), PROCRIT human recombinant erythropoietin (Ortho Biotech Products, L.P., Raritan N.J.), Continuous erythropoiesis receptor activator (CERA; F. Hoffmann-La Roche Ltd., Basel, Switzerland), etc.

The terms "erythropoietin-associated conditions" and "conditions mediated at least in part by erythropoietin" are used inclusively and refer to any condition that can be associated with below normal, abnormal, or inappropriate modulation of erythropoietin. EPO-associated conditions include any condition wherein an increase in EPO level would provide therapeutic benefit. Erythropoietin-associated conditions include anemic conditions such as those described above.

EPO-associated conditions further include neurological disorders and/or injuries, including cases of stroke, trauma, epilepsy, neurodegenerative disease and the like, wherein erythropoietin may provide a neuroprotective effect. Neurodegenerative diseases contemplated by the invention include Alzheimer's disease, Parkinson's disease, Huntington's disease, and the like.

The terms "treating," "treatment" and the like, are used herein to mean administering a therapy to a patient in need thereof. The therapy may be administered thereby providing a prophylactic effect in terms of completely or partially preventing a disorder or sign or symptom thereof and/or the therapy may be administered thereby providing a partial or complete cure for a disorder and/or adverse effect attributable to the disorder.

The term "alkyl" refers to saturated monovalent hydrocarbyl groups having from 1 to 10 carbon atoms, more particularly from 1 to 5 carbon atoms, and even more particularly 1 to 3 carbon atoms. This term is exemplified by groups such as methyl, ethyl, n-propyl, iso-propyl, n-butyl, t-butyl, n-pentyl, and the like.

The term "substituted alkyl" refers to an alkyl group of from 1 to 10 carbon atoms, more particularly 1 to 5 carbon atoms, and having from 1 to 5 substituents, preferably 1 to 3 substituents, each of which substituents is independently selected from the group consisting of alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, thio, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, sulfonyl, substituted sulfonyl, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, and —OSO$_2$—NR$^{40}$NR$^{40}$, —NR$^{40}$S(O)$_2$—NR$^{40}$-alkyl, —NR$^{40}$S(O)$_2$—NR$^{40}$-substituted alkyl, —NR$^{40}$S(O)$_2$—NR$^{40}$-aryl, —NR$^{40}$S(O)$_2$—NR$^{40}$-substituted aryl, —NR$^{40}$S(O)$_2$—NR$^{40}$-heteroaryl, —NR$^{40}$S(O)$_2$—NR$^{40}$-substituted heteroaryl, —NR$^{40}$S(O)$_2$—NR$^{40}$-heterocyclic, and —NR$^{40}$S(O)$_2$—NR$^{40}$-substituted heterocyclic, where each R$^{40}$ is independently selected from hydrogen or alkyl. This group is exemplified by groups such as trifluoromethyl, benzyl, pyrazol-1-ylmethyl, etc.

The term "alkoxy" refers to the group "alkyl-O—" which includes, by way of example, methoxy, ethoxy, n-propoxy, iso-propoxy, n-butoxy, t-butoxy, sec-butoxy, n-pentoxy, and the like.

The term "substituted alkoxy" refers to the group "substituted alkyl-O—".

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—, provided that a nitrogen atom of the heterocyclic or substituted heterocyclic is not bound to the —C(O)— group, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminoacyl" or "amide," or the prefix "carbamoyl," "carboxamide," "substituted carbamoyl" or "substituted carboxamide" refers to the group —C(O)NR$^{42}$R$^{42}$ where each R$^{42}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic; or where each $R^{42}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "alkenyl" refers to a vinyl unsaturated monovalent hydrocarbyl group having from 2 to 6 carbon atoms, and preferably 2 to 4 carbon atoms, and having at least 1, and preferably from 1 to 2 sites of vinyl ($>C=C<$) unsaturation. Such groups are exemplified by vinyl (ethen-1-yl), allyl, but-3-enyl and the like.

The term "substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This term includes both E (cis) and Z (trans) isomers as appropriate. It also includes mixtures of both E and Z components.

The term "alkynyl" refers to acetylenic unsaturated monovalent hydrocarbyl groups having from 2 to 6 carbon atoms, and preferably 2 to 3 carbon atoms, and having at least 1, and preferably from 1 to 2 sites of acetylenic (—C≡C—) unsaturation. This group is exemplified by ethyn-1-yl, propyn-1-yl, propyn-2-yl, and the like.

The term "substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This group is exemplified by groups such as phenylethynyl, etc.

The term "amino" refers to the group —$NH_2$.

The term "substituted amino" refers to the group —$NR^{41}R^{41}$, where each $R^{41}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, sulfonyl, and substituted sulfonyl, provided that both $R^{41}$ groups are not hydrogen; or the $R^{41}$ groups can be joined together with the nitrogen atom to form a heterocyclic or substituted heterocyclic ring. This group is exemplified by phenylamino, methylphenylamino, and the like. This group is exemplified by groups such as (ethanic acid-2-yl)amino, etc.

The term "acylamino" refers to the groups —$NR^{45}C(O)$alkyl, —$NR^{45}C(O)$substituted alkyl, —$NR^{45}C(O)$cycloalkyl, —$NR^{45}C(O)$substituted cycloalkyl, —$NR^{45}C(O)$alkenyl, —$NR^{45}C(O)$substituted alkenyl, —$NR^{45}C(O)$alkynyl, —$NR^{45}C(O)$substituted alkynyl, —$NR^{45}C(O)$aryl, —$NR^{45}C(O)$substituted aryl, —$NR^{45}C(O)$heteroaryl, —$NR^{45}C(O)$substituted heteroaryl, —$NR^{45}C(O)$heterocyclic, and —$NR^{45}C(O)$substituted heterocyclic where $R^{45}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are defined herein.

The term "oxycarbonylamino" refers to the groups —$NR^{46}C(O)O$-alkyl, —$NR^{46}C(O)O$-substituted alkyl, —$NR^{46}C(O)O$-alkenyl, —$NR^{46}C(O)O$-substituted alkenyl, —$NR^{46}C(O)O$-alkynyl, —$NR^{46}C(O)O$-substituted alkynyl, —$NR^{46}C(O)O$-cycloalkyl, —$NR^{46}C(O)O$-substituted cycloalkyl, —$NR^{46}C(O)O$-aryl, —$NR^{46}C(O)O$-substituted aryl, —$NR^{46}C(O)O$-heteroaryl, —$NR^{46}C(O)O$-substituted heteroaryl, —$NR^{46}C(O)O$-heterocyclic, and —$NR^{46}C(O)O$- substituted heterocyclic where $R^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "oxythiocarbonylamino" refers to the groups —$NR^{46}C(S)O$-alkyl, —$NR^{46}C(S)O$-substituted alkyl, —$NR^{46}C(S)O$-alkenyl, —$NR^{46}C(S)O$-substituted alkenyl, —$NR^{46}C(S)O$-alkynyl, —$NR^{46}C(S)O$-substituted alkynyl, —$NR^{46}C(S)O$-cycloalkyl, —$NR^{46}C(S)O$-substituted cycloalkyl, —$NR^{46}C(S)O$-aryl, —$NR^{46}C(S)O$-substituted aryl, —$NR^{46}C(S)O$-heteroaryl, —$NR^{46}C(S)O$-substituted heteroaryl, —$NR^{46}C(S)O$-heterocyclic, and —$NR^{46}C(S)O$-substituted heterocyclic where $R^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonyloxy," or the prefix "carbamoyloxy" or "substituted carbamoyloxy," refers to the groups —$OC(O)NR^{47}R^{47}$ where each $R^{47}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic; or where each $R^{47}$ is joined to form, together with the nitrogen atom, a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonylamino" refers to the group —$NR^{49}C(O)N(R^{49})_2$ where each $R^{49}$ is independently selected from the group consisting of hydrogen and alkyl.

The term "aminothiocarbonylamino" refers to the group —$NR^{49}C(S)N(R^{49})_2$ where each $R^{49}$ is independently selected from the group consisting of hydrogen and alkyl.

The term "aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is the aryl group. Preferred aryls include phenyl and naphthyl.

The term "substituted aryl" refers to aryl groups, as defined herein, which are substituted with from 1 to 4, particularly 1 to 3, substituents selected from the group consisting of hydroxy, acyl, acylamino, acyloxy, alkyl, substituted alkyl, alkoxy, substituted alkoxy, alkenyl, substituted alkenyl, alkynyl, substituted alkynyl, amidino (—C(=NH)-amino or substituted amino), amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters, cyano, thio, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino (—NH—C(=NH)-amino or substituted amino), halo, nitro, heteroaryl, substituted heteroaryl, heterocyclic, substituted heterocyclic, oxycarbonylamino, oxythiocarbonylamino, sulfonyl, substituted sulfonyl, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, and —OSO$_2$—NR$^{51}$R$^{51}$, —NR$^{51}$S(O)$_2$—NR$^{51}$-alkyl, —NR$^{51}$S(O)$_2$—NR$^{51}$-substituted alkyl, —NR$^{51}$S(O)$_2$—NR$^{51}$-aryl, —NR$^{51}$S(O)$_2$—NR$^{51}$-substituted aryl, —NR$^{51}$S(O)$_2$—NR$^{51}$-hetero aryl, —NR$^{51}$S(O)$_2$—NR$^{51}$-substituted hetero aryl, —NR$^{51}$S(O)$_2$—NR$^{51}$-heterocyclic, —NR$^{51}$S(O)$_2$—NR$^{51}$-substituted heterocyclic, where each R$^{51}$ is independently selected from hydrogen or alkyl, wherein each of the terms is as defined herein. This group is exemplified by groups such as 4-fluorophenyl, 3-methoxyphenyl, 4-t-butylphenyl, 4-trifluoromethylphenyl, 2-trifluoromethoxyphenyl, 3-trifluoromethoxyphenyl, 4-trifluoromethoxyphenyl, 2-chlorophenyl, 3-chlorophenyl, 4-chlorophenyl, 2-chloro-6-fluorophenyl, 2,4-dichlorophenyl, 4-methoxyphenyl, 3-cyanophenyl, 4-cyanophenyl, 4-phenoxyphenyl, 4-methanesulfonylphenyl, biphenyl-4-yl, etc.

The term "aryloxy" refers to the group aryl-O— that includes, by way of example, phenoxy, naphthoxy, and the like.

The term "substituted aryloxy" refers to substituted aryl-O— groups.

The term "aryloxyaryl" refers to the group -aryl-O-aryl.

The term "substituted aryloxyaryl" refers to aryloxyaryl groups substituted with from 1 to 3 substituents on either or both aryl rings as defined above for substituted aryl.

The term "carboxyl" refers to —COOH or salts thereof.

The term "carboxyl ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-cycloalkyl, —C(O)O-substituted cycloalkyl, —C(O)O-aryl, —C(O)O-substituted aryl, —C(O)O— heteroaryl, —C(O)O-substituted heteroaryl, —C(O)O-heterocyclic, and —C(O)O-substituted heterocyclic.

The term "cyano" refers to the group —CN.

The term "cycloalkyl" refers to a saturated or an unsaturated but nonaromatic cyclic alkyl groups of from 3 to 10, 3 to 8 or 3 to 6 carbon atoms having single or multiple cyclic rings including, by way of example, adamantyl, cyclopropyl, cyclobutyl, cyclopentyl, cyclooctyl, cyclohexenyl, and the like.

The term "substituted cycloalkyl" refers to a cycloalkyl group, having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl esters, cycloalkyl, substituted cycloalkyl, heteroaryl, substituted heteroaryl, heterocyclic, and substituted heterocyclic.

The term "cycloalkoxy" refers to —O-cycloalkyl groups.

The term "substituted cycloalkoxy" refers to —O-substituted cycloalkyl groups.

The term "halo" or "halogen" refers to fluoro, chloro, bromo, and iodo.

The term "hydroxy" or "hydroxyl" refers to the group —OH.

The term "heteroaryl" refers to an aromatic ring of from 1 to 15 carbon atoms, preferably from 1 to 10 carbon atoms, and 1 to 4 heteroatoms within the ring selected from the group consisting of oxygen, nitrogen, and sulfur. Such heteroaryl groups can have a single ring (e.g., pyridinyl, furyl, or thienyl) or multiple condensed rings (e.g., indolizinyl or benzothienyl) provided the point of attachment is through a ring containing the heteroatom and that ring is aromatic. The nitrogen and/or sulfur ring atoms can optionally be oxidized to provide for the N-oxide or the sulfoxide, and sulfone derivatives. Examples of heteroaryls include but are not limited to, pyridinyl, pyrrolyl, indolyl, thiophenyl, thienyl, and furyl.

The term "substituted heteroaryl" refers to heteroaryl groups that are substituted with from 1 to 3 substituents selected from the same group of substituents defined for substituted aryl. This group is exemplified by groups such as 1-benzyl-1H-[1,2,3]triazol-4-yl, 5-bromo-furan-2-yl etc.

The term "heteroaryloxy" refers to the group —O-heteroaryl, and "substituted heteroaryloxy" refers to the group —O-substituted heteroaryl.

The term "heterocyclyl" or "heterocyclic" refers to a saturated or unsaturated (but not aromatic) group having a single ring or multiple condensed rings, from 1 to 10 carbon atoms, and from 1 to 4 hetero atoms selected from the group consisting of nitrogen, sulfur or oxygen within the ring wherein, in fused ring systems, one or more of the rings can be aryl or heteroaryl provided that the point of attachment is at the heterocycle. The nitrogen and/or sulfur ring atoms can optionally be oxidized to provide for the N-oxide or the sulfoxide, and sulfone derivatives.

The term "substituted heterocyclic" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

The term "nitro" refers to the group —NO$_2$.

The term "oxo" refers to the atom (=O) or the atom (—O$^-$).

The term "sulfonyl" refers to the group —S(O)$_2$H. The term "substituted sulfonyl" refers to the group —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$- cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

The term "heterocyclyloxy" refers to the group —O-heterocyclic, and "substituted heterocyclyloxy" refers to the group —O-substituted heterocyclic.

The term "thio" or "mercapto" refers to the group —SH.

The term "alkylsulfanyl," "alkylthio," or "thioether" refers to the groups —S-alkyl where alkyl is as defined above.

The term "substituted alkylthio," "substituted alkylsulfanyl," or "substituted alkylthio" refers to the group —S-substituted alkyl where substituted alkyl is as defined above.

The term "cycloalkylthio" or "cycloalkylsulfanyl" refers to the groups —S-cycloalkyl where cycloalkyl is as defined above.

The term "substituted cycloalkylthio" refers to the group —S-substituted cycloalkyl where substituted cycloalkyl is as defined above.

The term "arylthio" or "arylsulfanyl" refers to the group —S-aryl, and "substituted arylthio" refers to the group —S-substituted aryl where aryl and substituted aryl are as defined above.

The term "heteroarylthio" or "heteroarylsulfanyl" refers to the group —S-heteroaryl, and "substituted heteroarylthio" refers to the group —S-substituted heteroaryl where heteroaryl and substituted heteroaryl are as defined above.

The term "heterocyclicthio" or "heterocyclicsulfanyl" refers to the group —S-heterocyclic, and "substituted heterocyclicthio" refers to the group —S-substituted heterocyclic where heterocyclic, and substituted heterocyclic are as defined above.

The term "pharmaceutically acceptable salt" refers to pharmaceutically acceptable salts of a compound, which salts are derived from a variety of organic, and inorganic counter ions well known in the art, and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like.

The terms "stereoisomer" or "stereoisomers" refer to compounds that differ in the chirality of one or more stereocenters. Stereoisomers include enantiomers (compounds are non-superimposable mirror images) and diastereomers (compounds having more than one stereogenic center that are non-mirror images of each other and wherein one or more stereogenic center differs between the two stereoisomers). The compounds of the invention can be present as a mixture of stereoisomers or as a single stereoisomer.

The term "prodrug," as used herein, refers to compounds of Formula I, II, III, or IV, that include chemical groups which, in vivo, can be converted into the carboxylate group adjacent to the —C(R$^1$)(R$^8$) substituent and/or can be split off from the amide N-atom and/or can be split off from the oxygen atom beta to the N-atom of the pyridyl ring; and/or can be split off from the N-atom of the pyridyl ring to provide for the active drug, a pharmaceutically acceptable salt thereof, or a biologically active metabolite thereof. Suitable groups are well known in the art and particularly include: for the carboxylic acid moiety a prodrug selected from, e.g., esters including, but not limited to, those derived from alkyl alcohols, substituted alkyl alcohols, hydroxy substituted aryls and heteroaryls and the like; amides, particularly amides derived from amines of the formula HNR$^{200}$R$^{210}$ where R$^{200}$ and R$^{210}$ are independently hydrogen, alkyl, substituted alkyl, aryl, substituted aryl, and the like; hydroxymethyl, aldehyde and derivatives thereof and for the pyridyl N atom, a prodrug selected from, e.g., N-oxides and N-alkyl derivatives.

The term "excipient" as used herein means an inert or inactive substance used in the production of pharmaceutical products or other tablets, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose dc, honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

4. Compound Preparation

The compounds of this invention can be prepared from readily available starting materials using, for example, the following general methods, and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis*, 3rd Edition, Wiley, New York, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

Synthesis of Compounds of the Invention

The isothiazolopyridines of this invention are prepared by, for example, the synthetic protocols illustrated in Schemes A, B, and C. The substituents $R^1$, $R^2$, $R^3$, and $R^8$ are as defined herein.

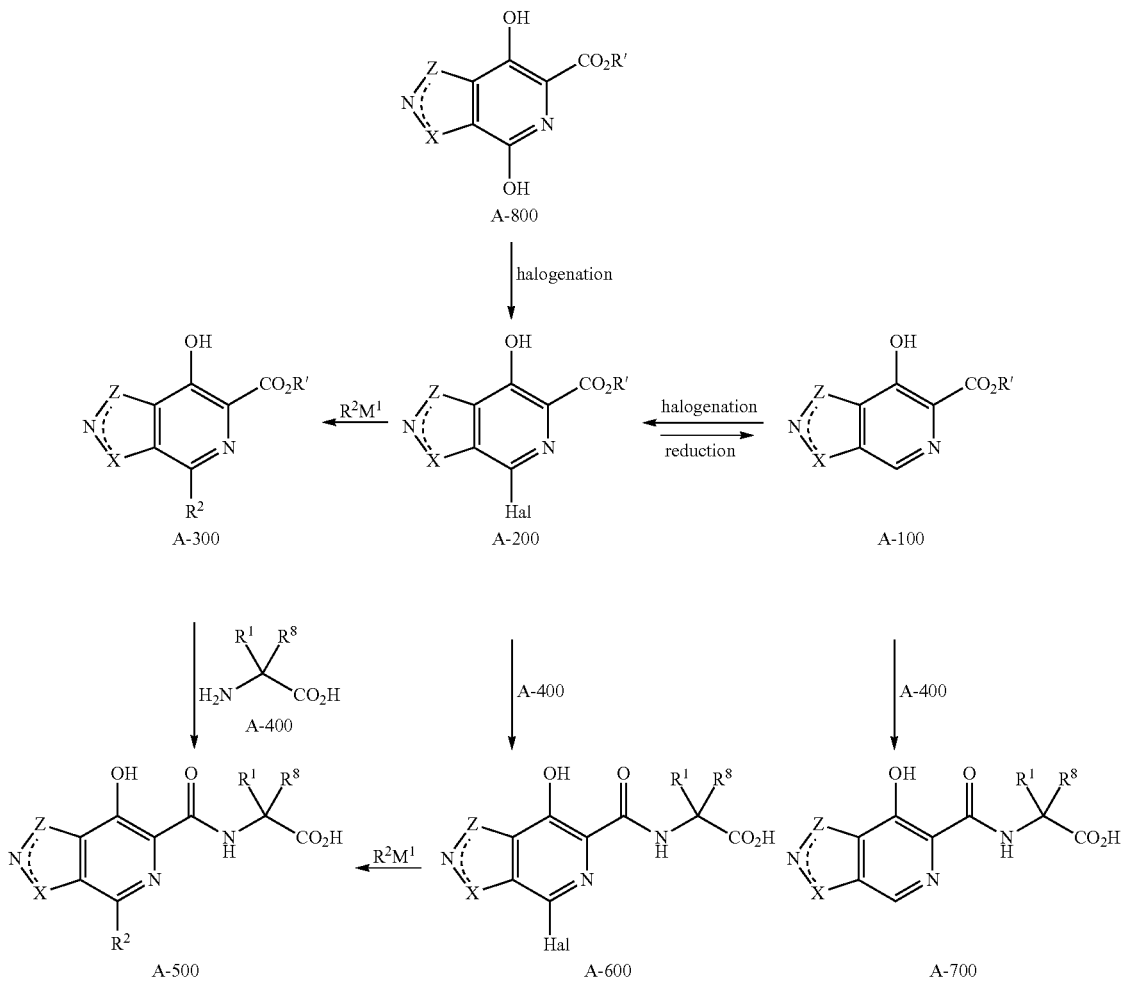

Scheme A one of Z or X is —S—, the other is ═C($R^3$)—

Compounds A-300 (wherein R' refers to a suitable protecting group such as methyl, ethyl, butyl, etc.) are reacted with at least a stoichiometric amount and preferably an excess of a suitable alpha-amino acid, compound A-400 (particularly, but not limited to, glycine). The reaction is conducted under conventional coupling conditions well known in the art. In one embodiment, the reaction is conducted in the presence of sodium methoxide or another suitable base in methanol or another suitable solvent under elevated reaction temperatures and particularly at reflux. The reaction is continued until it is substantially complete which typically occurs within about 1 to 72 h. Alternatively, the reaction can be performed at elevated temperatures in a microwave oven. Upon reaction completion, the compounds A-500 can be recovered by conventional techniques such as neutralization, extraction, precipitation, chromatography, filtration and the like.

Alternatively, compounds A-600 may be reacted with $R^2M^1$, which includes, but is not limited to, $Zn(CN)_2$, suitable boronic acids such as $p$-$FC_6H_4B(OH)_2$ or suitable derivatives thereof such as the corresponding esters, or organotin compounds such as $n$-$Bu_3SnPh$, $Me_4Sn$, etc., or organosilicon compounds such as trimethylsilyl acetylene, etc., or similar reagents known to one skilled in the art in the presence of a suitable catalyst if required (particularly, but not limited to, palladium catalysts known to one skilled in the art such as $Pd(PPh_3)_4$, $Pd_2(dba)_3$, or $Cl_2Pd(PPh_3)_2$) and if required a suitable base or additive known to one skilled in the art using a suitable solvent known to one skilled in the art. Upon reaction completion, compounds A-500 can be recovered by conventional techniques such as neutralization, extraction, precipitation, chromatography, filtration and the like; or, alternatively, used in the next step without purification and/or isolation.

Compounds A-300 are obtained by reacting the compounds A-200 with $R^2M^1$, which includes, but is not limited to, CuCN, suitable boronic acids such as $p$-$FC_6H_4B(OH)_2$ or suitable derivatives thereof such as the corresponding esters, or organotin compounds such as $n$-$Bu_3SnPh$, $Me_4Sn$, etc., or organosilicon compounds such as trimethylsilyl acetylene, etc., or similar reagents known to one skilled in the art in the presence of a suitable catalyst if required (particularly, but not limited to, palladium catalysts known to one skilled in the art such as $Pd(PPh_3)_4$, $Pd_2(dba)_3$, or $Cl_2Pd(PPh_3)_2$) and if required a suitable base or additive known to one skilled in the art using a suitable solvent known to one skilled in the art. Upon reaction completion the compounds A-300 can be recovered by conventional techniques such as neutralization, extraction, precipitation, chromatography, filtration and the like; or, alternatively, used in the next step without purification and/or isolation. Compounds A-300 obtained this way may be further altered by modifying its $R^3$ moiety. For example, if $R^3$ is methyl, it can be transformed into the corresponding $CH_2$-Hal moiety by halogenation and subsequently be reacted with suitable nucleophiles such as indole using conventional techniques known to one skilled in the art to yield $R^3$ moieties such as $CH_2$-indol-1-yl (not depicted).

Compounds A-600 are obtained by reacting the compounds A-200 with at least a stoichiometric amount and preferably an excess of a suitable alpha-amino acid of the formula mentioned above, compound A-400 (particularly, but not limited to, glycine). The reaction is conducted under conventional coupling conditions well known in the art. In one embodiment, the reaction is conducted in the presence of sodium methoxide or another suitable base in methanol or another suitable solvent under elevated reaction temperatures and particularly at reflux. The reaction is continued until it is substantially complete which typically occurs within about 1 to 72 h. Alternatively, the reaction can be performed at elevated temperatures in a microwave oven. Upon reaction completion, the compounds A-600 can be recovered by conventional techniques such as neutralization, extraction, precipitation, chromatography, filtration and the like.

Compounds A-200 are obtained by halogenation of compounds A-100 or A-800 using conventional methods (Hal=Cl, Br, I). The halogenation of compounds A-100 is particularly performed with, but not limited to, a slight excess of NBS if required in the presence of a catalytic amount of $Bz_2O_2$, in $CCl_4$, benzene, or another suitable solvent known to one skilled in the art, typically at, but not limited to, reflux temperature. Alternatively, the halogenation can be performed with iodine or bis(2,4,6-trimethylpyridine)iodine(I) hexafluorophosphate, if necessary in the presence of a suitable base (particularly, but not limited to, $K_2CO_3$) using a suitable solvent (particularly, but not limited to, $CH_2Cl_2$) at a suitable temperature (particularly, at but not limited to, ambient temperature). The halogenation of compounds A-800 is particularly performed with, but not limited to, at least a stoichiometric amount and preferably an excess of $POBr_3$ or $POCl_3$ in a suitable solvent such as 1,2-dichloroethane, toluene, acetonitrile, etc., preferably, but not limited to reflux conditions or in a microwave oven at further elevated temperatures. Upon reaction completion, compounds A-200 can be recovered by conventional techniques such as neutralization, extraction, precipitation, chromatography, filtration and the like; or, alternatively, used in the next step without purification and/or isolation.

Compounds A-100 (wherein R' refers to a suitable protecting group such as methyl, ethyl, butyl, etc.) are reacted with at least a stoichiometric amount and preferably an excess of a suitable alpha-amino acid of the formula mentioned above, compound A-400 (particularly, but not limited to, glycine). The reaction is conducted under conventional coupling conditions well known in the art. In one embodiment, the reaction is conducted in the presence of sodium methoxide or another suitable base in methanol or another suitable solvent under elevated reaction temperatures and particularly at reflux. The reaction is continued until it is substantially complete which typically occurs within about 1 to 72 h. Alternatively, the reaction can be performed at elevated temperatures in a microwave oven. Upon reaction completion, the compounds A-700 can be recovered by conventional techniques such as neutralization, extraction, precipitation, chromatography, filtration and the like.

Compounds A-100 are preferably obtained by, but not limited to, conventional palladium-catalyzed hydrogenation of compounds A-200 (Scheme A). Alternatively, compounds A-100 can be obtained by the synthetic methods outlined in Scheme B.

Scheme B

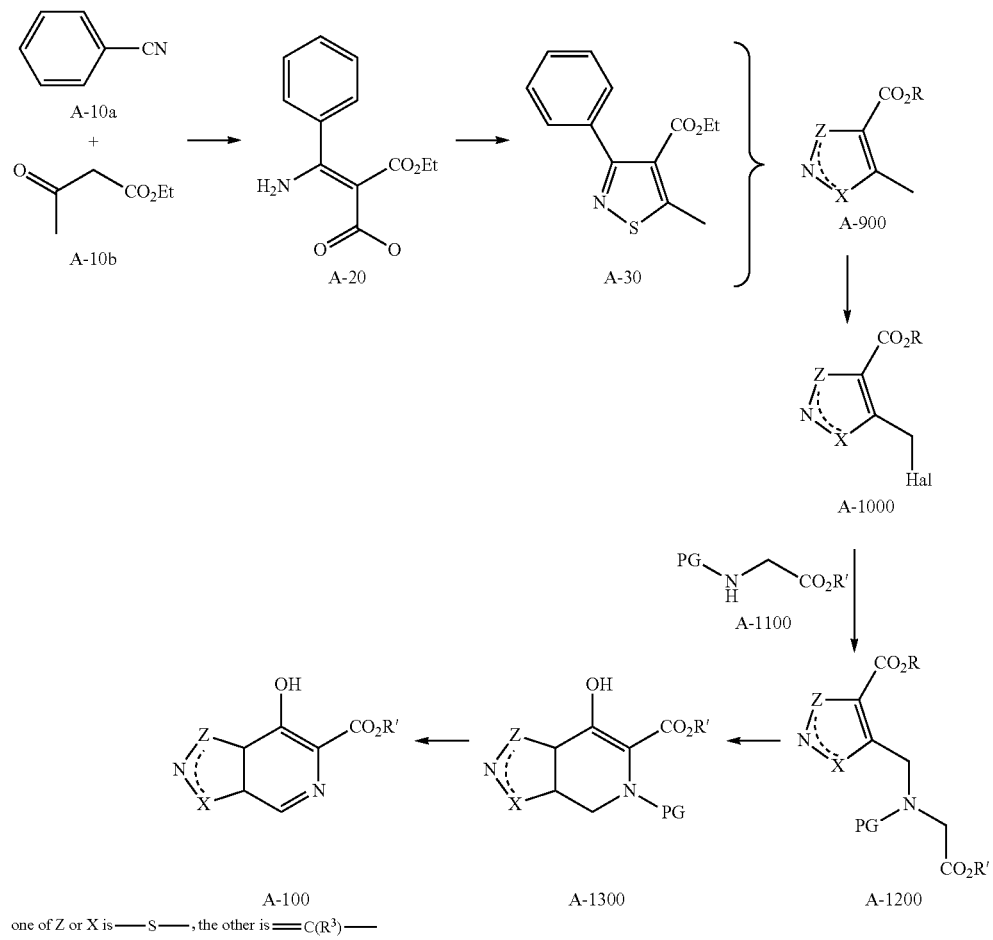

one of Z or X is —S—, the other is =C(R³)—

The synthesis of compounds A-900 (R=e.g., alkyl, such as methyl (Me), ethyl (Et), etc.) can be exemplified by, but is not limited to, the preparation of compound A-30. For example, compound A-20 can be prepared by reacting compound A-10a with A-10b in the presence of SnCl$_4$ using a suitable solvent such as benzene at reflux temperature. Compound A-20 can be recovered by conventional techniques such as neutralization, extraction, precipitation, chromatography, filtration and the like; or, alternatively, used in the next step without purification and/or isolation. Compound A-30 can be obtained by reaction of compound A-20 with P$_2$S$_5$ and tetrachloro-1,4-benzoquinone using a suitable solvent such as toluene at reflux temperature. Compound A-30 can be recovered by conventional techniques such as neutralization, extraction, precipitation, chromatography, filtration and the like; or, alternatively, used in the next step without purification and/or isolation.

The aromatic methyl group of compounds A-900 is halogenated using conventional methods to give compounds A-1000 (Hal=Cl, Br, I). The halogenation of compounds A-900 is particularly performed with, but not limited to, a stoichiometric amount of NBS in the presence of a catalytic amount of Bz$_2$O$_2$, azobisisobutyronitrile (AIBN), or another suitable free radical initiator known to one skilled in the art, in CCl$_4$, benzene, or another suitable solvent known to one skilled in the art, typically at, but not limited to, reflux temperature. Upon reaction completion, compounds A-1000 can be recovered by conventional techniques such as neutralization, extraction, precipitation, chromatography, filtration and the like; or, alternatively, used in the next step without purification and/or isolation.

Compounds A-1000 are used for the N-alkylation of a protected glycine ester A-1100 (R'=e.g., alkyl, such as methyl, ethyl, etc.; PG is particularly, but not limited to, Boc or DMB) to give compounds A-1200. The N-alkylation step is typically performed in DMF, THF or another suitable solvent known to one skilled in the art, typically at, but not limited to, room temperature or 0° C. in the presence of K$_2$CO$_3$, NaH, or another suitable base known to one skilled in the art. Upon reaction completion, compounds A-1200 can be recovered by conventional techniques such as neutralization, extraction, precipitation, chromatography, filtration and the like; or, alternatively, used in the next step without purification and/or isolation.

Compounds A-1200 are reacted in THF or another suitable solvent known to one skilled in the art, typically at, but not limited to, −78° C. to room temperature in the presence of KOtBu, or another suitable base known to one skilled in the art to give the compounds A-1300. Upon reaction completion, A-1300 can be recovered by conventional techniques such as neutralization, extraction, precipitation, chromatography, filtration and the like; or, alternatively, used in the next step without purification and/or isolation.

The compounds A-1300 are transformed into compounds A-100 by subsequent deprotection/oxidation. This can be achieved, in addition to other methods known to one skilled in the art, by treatment of A-1300 with SOCl$_2$ in a suitable solvent such as CH$_2$Cl$_2$ (preferred method for PG=DMB); alternatively, A-1300 can be deprotected with TFA neat or in a suitable solvent known to one skilled in the art followed by air oxidation in the presence of NEt$_3$ or another suitable base known to one skilled in the art to give the compounds A-100 (preferred method for PG=Boc). Upon reaction completion, A-100 can be recovered by conventional techniques such as neutralization, extraction, precipitation, chromatography, filtration and the like; or, alternatively, used in the next step without purification and/or isolation.

Compounds A-800 can be obtained among other things by the synthetic methods outlined in Scheme C.

neutralization, extraction, precipitation, chromatography, filtration and the like; or, alternatively, used in the next step without purification and/or isolation.

Compounds A-1500 can be obtained by hydrolysis of one of the ester groups of compounds A-1400 by treating A-1400 with a suitable base in a suitable solvent system, preferably, but not limited to NaOH in water/THF/MeOH, preferably at, but not limited to ambient temperature. Compounds A-1500 can be recovered by conventional techniques such as neutralization, extraction, precipitation, chromatography, filtration and the like; or, alternatively, used in the next step without purification and/or isolation.

Compounds A-1700 can be obtained by coupling of compounds A-1500 with glycine ester A-1600 (R"=methyl (Me), ethyl (Et), etc., preformed or generated in situ from treatment of its salt, e.g., its hydrochloride, with a suitable base, e.g.,

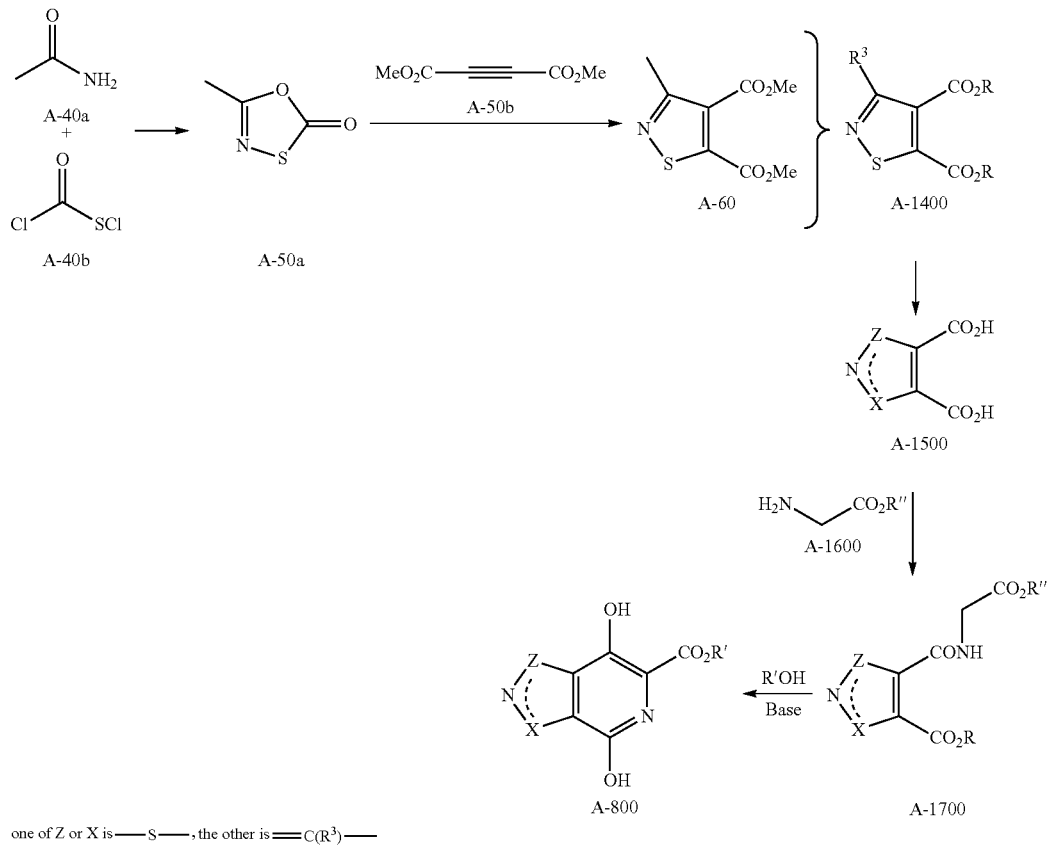

Scheme C one of Z or X is ——S——, the other is ══C(R$^3$)——

The synthesis of compounds A-1400 can be exemplified by, but is not limited to, the preparation of compound A-60. For example, compound A-50a can be prepared by reacting compound A-40a with A-40b in using a suitable solvent such as toluene typically at, but not limited to 100° C. Compound A-50a can be recovered by conventional techniques such as neutralization, extraction, precipitation, chromatography, filtration and the like; or, alternatively, used in the next step without purification and/or isolation. Compound A-60 can be obtained by reaction of compound A-50a with compound A-50b using a suitable solvent such as chlorobenzene typically at, but not limited to reflux temperature. Compound A-60 can be recovered by conventional techniques such as triethylamine) using conventional amide bond forming techniques (peptide coupling methods) known to one skilled in the art. Compounds A-1700 can be recovered by conventional techniques such as neutralization, extraction, precipitation, chromatography, filtration and the like; or, alternatively, used in the next step without purification and/or isolation.

Compounds A-800 can be obtained by treatment of compounds A-1700 with a suitable base (either preformed or generated in situ, e.g., by reaction of sodium with an alcohol) in a suitable solvent, preferably but not limited to alcohols R'OH (R' is preferably, but not limited to, butyl). The reaction is preferably performed at, but not limited to, a reaction temperature of 110° C. Compounds A-800 can be recovered by conventional techniques such as neutralization, extraction, precipitation, chromatography, filtration and the like; or, alternatively, used in the next step without purification and/or isolation.

Other modifications to arrive at compounds of this invention are well within the skill of the art. For example, modification of the hydroxy group that is beta to the nitrogen of the 5,6-membered bicyclic ring may be done by conventional means to corresponding ethers, etc.

5. Use of Compounds of the Invention

The compounds of the present invention can be used to inhibit HIF hydroxylase enzyme activity, thereby modulating the stability and/or activity of HIF and activating HIF-regulated gene expression. The compounds can be used in methods to treat, pretreat, or delay progression or onset of conditions associated with HIF including, but not limited to, anemic, ischemic, and hypoxic conditions. In various embodiments, the compound is administered immediately following an acute condition producing ischemia, e.g., myocardial infarction, pulmonary embolism, intestinal infarction, ischemic stroke, and renal ischemic-reperfusion injury. In another embodiment, the compound is administered to a patient diagnosed with a chronic condition associated with the development of ischemia, e.g., cardiac cirrhosis, macular degeneration, pulmonary embolism, acute respiratory failure, neonatal respiratory distress syndrome, and congestive heart failure. In yet another embodiment, the compound is administered immediately after a trauma or injury. In other embodiments, the compound can be administered to a subject based on predisposing conditions, e.g., hypertension, diabetes, occlusive arterial disease, chronic venous insufficiency, Raynaud's disease, chronic skin ulcers, cirrhosis, congestive heart failure, and systemic sclerosis. In still other embodiments, compounds may be administered to pretreat a subject to decrease or prevent the development of tissue damage associated with ischemia or hypoxia.

In particular embodiments, the compounds of the present invention can be used to increase endogenous erythropoietin (EPO). The compounds can be administered to prevent, pretreat, or treat EPO-associated conditions, including, e.g., conditions associated with anemia and neurological disorders. Conditions associated with anemia include disorders such as acute or chronic kidney disease, diabetes, cancer, ulcers, infection with virus, e.g., HIV, bacteria, or parasites; inflammation, etc. Anemic conditions can further include those associated with procedures or treatments including, e.g., radiation therapy, chemotherapy, dialysis, and surgery. Disorders associated with anemia additionally include abnormal hemoglobin and/or erythrocytes, such as found in disorders such as microcytic anemia, hypochromic anemia, aplastic anemia, etc.

The compounds can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Additionally, the compounds can be used to increase endogenous EPO levels in an anemic or non-anemic patient scheduled to undergo surgery to reduce the need for allogenic blood transfusions or to facilitate banking of blood prior to surgery.

6. Testing and Administration

The biological activity of the compounds of the invention may be assessed using any conventionally known methods. Suitable assay methods are well known in the art. The following assays are presented only as examples and are not intended to be limiting. The compounds of the invention are active in at least one of the following assays.

i. Cell-Based HIFα Stabilization Assay

Human cells derived from various tissues are separately seeded into 35 mm culture dishes, and grown at 37° C., 20% $O_2$, 5% $CO_2$ in standard culture medium, e.g., DMEM (Dulbecco's modification of Eagle's medium), 10% FBS (fetal bovine serum). When cell layers reach confluence, the media is replaced with OPTI-MEM media (Invitrogen Life Technologies, Carlsbad Calif.), and cell layers are incubated for approximately 24 hours in 20% $O_2$, 5% $CO_2$ at 37° C. Compound or 0.013% DMSO (dimethyl sulfoxide) is then added to existing medium and incubation is continued overnight.

Following incubation, the media is removed, centrifuged, and stored for analysis (see VEGF and EPO assays below). The cells are washed two times in cold phosphate buffered saline (PBS) and then lysed in 1 mL of 10 mM Tris (pH 7.4), 1 mM EDTA, 150 mM NaCl, 0.5% IGEPAL (Sigma-Aldrich, St. Louis Mo.), and a protease inhibitor mix (Roche Molecular Biochemicals) for 15 minutes on ice. Cell lysates are centrifuged at 3,000×g for 5 minutes at 4° C., and the cytosolic fractions (supernatant) are collected. The nuclei (pellet) are resuspended and lysed in 100 μL of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fractions (supernatant) are collected.

Nuclear fractions are analyzed for HIF-1α using a QUANTIKINE immunoassay (R&D Systems, Inc., Minneapolis Minn.) according to the manufacturer's instructions.

ii. Cell-Based VEGF and EPO ELISA Assays

Conditioned media collected from cell cultures as described above is analyzed for vascular endothelial growth factor (VEGF) and/or erythropoietin (EPO) expression using an appropriate QUANTIKINE immunoassay (R&D Systems) according to the manufacturer's instructions.

iii. HIF-PH Assay

Ketoglutaric acid α-[$1$-$^{14}C$]-sodium salt, alpha-ketoglutaric acid sodium salt, and HPLC purified peptide may be obtained from commercial sources, e.g., Perkin-Elmer (Wellesley Mass.), Sigma-Aldrich, and SynPep Corp. (Dublin Calif.), respectively. Peptides for use in the assay may be fragments of HIFα as described above or as disclosed in International Publication WO 2005/118836, incorporated by reference herein. For example, a HIF peptide for use in the HIF-PH assay is [methoxycoumarin]-DLDLEALAPYIPAD-DDFQL-amide. HIF-PH, e.g., HIF-PH2 (EGLN1), can be expressed in, e.g., insect Hi5 cells, and partially purified, e.g., through a SP ion exchange chromatography column. Enzyme activity is determined by capturing $^{14}CO_2$ using an assay described by Kivirikko and Myllyla (1982, *Methods Enzymol.* 82:245-304). Assay reactions contain 50 mM HEPES (pH 7.4), 100 μM α-ketoglutaric acid sodium salt, 0.30 μCi/mL ketoglutaric acid α-[$1$-$^{14}C$]-sodium salt, 40 μM $FeSO_4$, 1 mM ascorbate, 1541.8 units/mL Catalase, with or without 50 μM peptide substrate and various concentrations of compound of the invention. Reactions are initiated by addition of HIF-PH enzyme.

The peptide-dependent percent turnover is calculated by subtracting percent turnover in the absence of peptide from percent turnover in the presence of substrate peptide. Percent inhibition and $IC_{50}$ are calculated using peptide-dependent percent turnover at given inhibitor concentrations. Calculation of $IC_{50}$ values for each inhibitor is conducted using GraFit software (Erithacus Software Ltd., Surrey UK).

Representative compounds of the invention were analyzed using the HIF-PH assay described above. Table I below presents enzyme inhibition data for exemplary compounds against HIF-PH2, a representative HIF prolyl hydroxylase enzyme. By inhibiting HIF prolyl hydroxylase enzymes, compounds of the invention stabilize HIFα, which then combines with HIFβ to form an active transcription factor that increases expression of various genes involved in numerous beneficial cellular processes.

TABLE 1

| No. | Name | Concentration (μM) | % Inhibition HIF-PH2 |
|---|---|---|---|
| 1 | {[7-(4-Fluoro-phenyl)-4-hydroxy-3-phenyl-isothiazolo[5,4-c]pyridine-5-carbonyl]-amino}-acetic acid | 200 | 98.0 |
| 2 | {[4-Hydroxy-7-(4-methoxy-phenyl)-3-phenyl-isothiazolo[5,4-c]pyridine-5-carbonyl]-amino}-acetic acid | 200 | 97.9 |
| 3 | [(4-Hydroxy-3-phenyl-7-pyridin-3-yl-isothiazolo[5,4-c]pyridine-5-carbonyl)-amino]-acetic acid | 200 | 100.0 |
| 4 | [(4-Hydroxy-3-phenyl-7-pyridin-2-yl-isothiazolo[5,4-c]pyridine-5-carbonyl)-amino]-acetic acid | 200 | 99.1 |
| 5 | [(4-Hydroxy-3-phenyl-7-pyridin-4-yl-isothiazolo[5,4-c]pyridine-5-carbonyl)-amino]-acetic acid | 200 | 97.1 |
| 6 | {[7-Ethynyl-3-(4-fluoro-phenyl)-4-hydroxy-isothiazolo[5,4-c]pyridine-5-carbonyl]-amino}-acetic acid | 200 | 98.3 |
| 7 | {[7-Bromo-3-(4-fluoro-phenyl)-4-hydroxy-isothiazolo[5,4-c]pyridine-5-carbonyl]-amino}-acetic acid | 200 | 100.0 |
| 8 | {[7-Cyano-3-(4-fluoro-phenyl)-4-hydroxy-isothiazolo[5,4-c]pyridine-5-carbonyl]-amino}-acetic acid | 22.22 | 98.3 |
| 9 | {[3-(4-Fluoro-phenyl)-4-hydroxy-7-methyl-isothiazolo[5,4-c]pyridine-5-carbonyl]-amino}-acetic acid | 200 | 97.4 |
| 10 | {[3-(4-Fluoro-phenyl)-4-hydroxy-7-phenyl-isothiazolo[5,4-c]pyridine-5-carbonyl]-amino}-acetic acid | 200 | 98.2 |
| 11 | {[7-(4-Cyano-phenyl)-3-(4-fluoro-phenyl)-4-hydroxy-isothiazolo[5,4-c]pyridine-5-carbonyl]-amino}-acetic acid | 22.22 | 91.5 |
| 12 | {[3-(4-Fluoro-phenyl)-4-hydroxy-isothiazolo[5,4-c]pyridine-5-carbonyl]-amino}-acetic acid | 200 | 98.9 |
| 13 | {[3-(4-Chloro-phenyl)-4-hydroxy-7-(4-methoxy-phenyl)-isothiazolo[5,4-c]pyridine-5-carbonyl]-amino}-acetic acid | 200 | 94.5 |
| 14 | {[3-(4-Chloro-phenyl)-7-ethynyl-4-hydroxy-isothiazolo[5,4-c]pyridine-5-carbonyl]-amino}-acetic acid | 200 | 100.0 |
| 15 | {[3-(4-Chloro-phenyl)-4-hydroxy-7-methyl-isothiazolo[5,4-c]pyridine-5-carbonyl]-amino}-acetic acid | 200 | 99.5 |
| 16 | {[3-(4-Chloro-phenyl)-4-hydroxy-isothiazolo[5,4-c]pyridine-5-carbonyl]-amino}-acetic acid | 200 | 99.9 |
| 17 | {[3-(4-Chloro-phenyl)-4-hydroxy-7-phenyl-isothiazolo[5,4-c]pyridine-5-carbonyl]-amino}-acetic acid | 200 | 98.7 |
| 18 | (R)-2-{[3-(4-Chloro-phenyl)-4-hydroxy-isothiazolo[5,4-c]pyridine-5-carbonyl]-amino}-propionic acid | 200 | 54.0 |
| 19 | (S)-2-{[3-(4-Chloro-phenyl)-4-hydroxy-isothiazolo[5,4-c]pyridine-5-carbonyl]-amino}-propionic acid | 200 | 100.0 |
| 20 | {[3-(4-Chloro-phenyl)-4-hydroxy-7-(3-methoxy-phenyl)-isothiazolo[5,4-c]pyridine-5-carbonyl]-amino}-acetic acid | 200 | 88.9 |
| 21 | {[3-(4-Chloro-phenyl)-4-hydroxy-7-(6-methoxy-pyridin-3-yl)-isothiazolo[5,4-c]pyridine-5-carbonyl]-amino}-acetic acid | 200 | 77 |
| 22 | {[7-Benzyl-3-(4-chloro-phenyl)-4-hydroxy-isothiazolo[5,4-c]pyridine-5-carbonyl]-amino}-acetic acid | 22.22 | 97 |
| 23 | {[7-(1-Benzyl-1H-[1,2,3]triazol-4-yl)-3-(4-chloro-phenyl)-4-hydroxy-isothiazolo[5,4-c]pyridine-5-carbonyl]-amino}-acetic acid | 22.22 | 100 |
| 24 | {[3-(4-Chloro-phenyl)-4-hydroxy-7-naphthalen-1-yl-isothiazolo[5,4-c]pyridine-5-carbonyl]-amino}-acetic acid | 22.22 | 96 |
| 25 | {[7-Acetyl-3-(4-chloro-phenyl)-4-hydroxy-isothiazolo[5,4-c]pyridine-5-carbonyl]-amino}-acetic acid | 200 | 100 |
| 26 | {[3-(4-Chloro-phenyl)-4-hydroxy-7-trifluoromethyl-isothiazolo[5,4-c]pyridine-5-carbonyl]-amino}-acetic acid | 200 | 100 |
| 27 | [(4-Bromo-7-hydroxy-3-phenyl-isothiazolo[4,5-c]pyridine-6-carbonyl)-amino]-acetic acid | 200 | 98 |
| 28 | [(4-Hydroxy-3,7-dimethyl-isothiazolo[5,4-c]pyridine-5-carbonyl)-amino]-acetic acid | 200 | 100 |
| 29 | [(7-Hydroxy-3,4-dimethyl-isothiazolo[4,5-c]pyridine-6-carbonyl)-amino]-acetic acid | 200 | 100 |
| 30 | [(4-Hydroxy-3-methyl-7-phenyl-isothiazolo[5,4-c]pyridine-5-carbonyl)-amino]-acetic acid | 200 | 100 |
| 31 | [(7-Hydroxy-3-methyl-4-phenyl-isothiazolo[4,5-c]pyridine-6-carbonyl)-amino]-acetic acid | 22.22 | 98 |
| 32 | [(7-Hydroxy-3-methyl-isothiazolo[4,5-c]pyridine-6-carbonyl)-amino]-acetic acid | 200 | 100 |
| 33 | {[3-(2-Fluoro-phenyl)-4-hydroxy-isothiazolo[5,4-c]pyridine-5-carbonyl]-amino}-acetic acid | 200 | 100 |
| 34 | {[3-(2-Fluoro-phenyl)-4-hydroxy-7-phenyl-isothiazolo[5,4-c]pyridine-5-carbonyl]-amino}-acetic acid | 200 | 100 |
| 35 | {[3-(2-Fluoro-phenyl)-4-hydroxy-7-(4-phenoxy-phenyl)-isothiazolo[5,4-c]pyridine-5-carbonyl]-amino}-acetic acid | 200 | 100 |
| 36 | {[3-(2-Fluoro-phenyl)-4-hydroxy-7-methyl-isothiazolo[5,4-c]pyridine-5-carbonyl]-amino}-acetic acid | 200 | 100 |
| 37 | [(4-Hydroxy-3-methyl-7-pyridin-3-yl-isothiazolo[5,4-c]pyridine-5-carbonyl)-amino]-acetic acid | 200 | 100 |
| 38 | [(4-Hydroxy-3-methyl-7-pyridin-2-yl-isothiazolo[5,4-c]pyridine-5-carbonyl)-amino]-acetic acid | 200 | 74 |
| 39 | [(7-Ethynyl-4-hydroxy-3-methyl-isothiazolo[5,4-c]pyridine-5-carbonyl)-amino]-acetic acid | 200 | 100 |
| 40 | [(4-Hydroxy-3-methyl-7-pyrazin-2-yl-isothiazolo[5,4-c]pyridine-5-carbonyl)-amino]-acetic acid | 22.22 | 70 |
| 41 | [(7-Hydroxy-3-methyl-4-pyrazin-2-yl-isothiazolo[4,5-c]pyridine-6-carbonyl)-amino]-acetic acid | 22.22 | 98 |
| 42 | [(7-Hydroxy-3-indol-1-ylmethyl-4-phenyl-isothiazolo[4,5-c]pyridine-6-carbonyl)-amino]-acetic acid | 22.22 | 100 |
| 43 | [(4-Hydroxy-3-phenyl-isothiazolo[5,4-c]pyridine-5-carbonyl)-amino]-acetic acid | 22.22 | 97 |
| 44 | [(4-Hydroxy-7-methyl-3-phenyl-isothiazolo[5,4-c]pyridine-5-carbonyl)-amino]-acetic acid | 22.22 | 91 |
| 45 | [(4-Hydroxy-3,7-diphenyl-isothiazolo[5,4-c]pyridine-5-carbonyl)-amino]-acetic acid | 22.22 | 97 |
| 46 | [(7-Ethyl-4-hydroxy-3-methyl-isothiazolo[5,4-c]pyridine-5-carbonyl)-amino]-acetic acid | 200 | 99 |
| 47 | [(4-Ethyl-7-hydroxy-3-methyl-isothiazolo[4,5-c]pyridine-6-carbonyl)-amino]-acetic acid | 200 | 99 |

7. Pharmaceutical Formulations and Routes of Administration

The compositions of the present invention can be delivered directly or in pharmaceutical compositions along with suitable carriers or excipients, as is well known in the art. Present methods of treatment can comprise administration of an effective amount of a compound of the invention to a subject in need; e.g., a subject having or at risk for anemia due to, e.g., chronic renal failure, diabetes, cancer, AIDS, radiation therapy, chemotherapy, kidney dialysis, or surgery; or, e.g., a subject having or at risk for ischemia due to, e.g., myocardial infarction, congestive heart failure, cardiac cirrhosis, pulmonary insufficiency, atherosclerosis, peripheral vascular disease, or the like. In a preferred embodiment, the subject is a mammalian subject, and in a most preferred embodiment, the subject is a human subject.

An effective amount of such agents can readily be determined by routine experimentation, as can the most effective and convenient route of administration, and the most appropriate formulation. Various formulations and drug delivery systems are available in the art. See, e.g., Gennaro, A. R., ed. (1995) Remington's Pharmaceutical Sciences, supra.

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art and include those listed in various pharmacopoeias. (See, e.g., the U.S. Pharmacopeia (USP), Japanese Pharmacopoeia (JP), European Pharmacopoeia (EP), and British pharmacopeia (BP); the U.S. Food and Drug Administration (www.fda.gov) Center for Drug Evaluation and Research (CEDR) publications, e.g., Inactive Ingredient Guide (1996); Ash and Ash, Eds. (2002) Handbook of Pharmaceutical Additives, Synapse Information Resources, Inc., Endicott N.Y.; etc.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms, and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid, or a liquid formulation, for example a gel, a (micro-) emulsion, an ointment, a solution, a (nano/micro-)suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methane and ethane, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound; sucrose or sodium chloride as a tonicity agent; and a buffer, for example, a buffer that contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack; or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Unless otherwise stated all temperatures are in degrees Celsius. Also, in these examples and elsewhere, abbreviations have the following meanings:

Aq.=aqueous

μCi=Microcuries

μL=Microliter
μM=Micromolar
BuOH=butanol
Boc=tert-Butoxycarbonyl
br=Broad
$Bu_3SnPh$=Tributyl tin phenyl
$Bz_2O_2$=Benzoyl peroxide
$CCl_4$=Carbon tetrachloride
$CH_2Cl_2$=Methylene dichloride
$CHCl_3$=Chloroform
$Cs_2CO_3$=Cesium carbonate
CuCN=Copper cyanide
CuI=Copper iodide
d=Doublet
DMA=N,N-dimethylacetamide
DMB=2,4-Dimethoxybenzyl
DMF=Dimethyl formamide
DMSO=Dimethyl sulfoxide
dppf=1,1'-bis(diphenylphosphino)ferrocene
EDTA=Ethylenediamine tetraacetic acid
ESI MS=Electrospray Ionization Mass Spectrometry
Et=Ethyl
EtOH=Ethanol
EtOAc=Ethyl acetate
g=Gram
h=Hour
HCOOH=Formic acid
Hz=Hertz
$K_2CO_3$=Potassium carbonate
KOtBu=Potassium tert-butoxide
L=Liter
M=Molar
m=Multiplet
m/z=Mass to charge ratio
Me=Methyl
$Me_4Sn$=Tetramethyltin (IV)
MeOH=Methanol
mg=Milligram
$MgSO_4$=Magnesium sulfate
MHz=Mega Hertz
min=Minute
mL=Milliliter
mM=Millimolar
mmol=Millimole
mol=Mole
N=Normal
NaCl=Sodium chloride
NaH=Sodium hydride
$NaHCO_3$=Sodium bicarbonate
NaOH=Sodium hydroxide
NaOMe=Sodium methoxide
NBS=N-bromosuccinimide
$NEt_3$=Triethylamine
$NH_4Cl$=Ammonium chloride
NMP=N-Methylpyrrolidone
NMR=Nuclear magnetic resonance
$POBr_3$=Phosphoryl bromide
$PPh_3$=Triphenyl phosphine
$Pd_2(dba)_3$=Tris(dibenzylideneacetone)dipalladium(0)
$Pd(PPh_3)_2Cl_2$=Dichlorobis(triphenylphosphine)palladium (II),
$Pd(PPh_3)_4$=tetrakis(triphenylphosphine)palladium(0)
$P_2S_5$=Phosphorus pentasulfide
Pd/C=Palladium over carbon
rt=Room temperature
s=Singlet
Sat.=Saturated
$SOCl_2$=Thionly chloride
$SnCl_4$=Tin tetrachloride
TFA=Trifluoroacetic acid
THF=Tetrahydrofuran
TLC=Thin layer chromatography
$Zn(CN)_2$=Zinc cyanide

EXAMPLES

Example 1

{[7-(4-Fluoro-phenyl)-4-hydroxy-3-phenyl-isothiazolo[5,4-c]pyridine-5-carbonyl]-amino}-acetic acid a) 2-(Amino-phenyl-methylene)-3-oxo-butyric acid ethyl ester To a solution of the benzonitrile (40 g, 388.3 mmol) in benzene (600 mL) were added $SnCl_4$ (44.75 mL, 388.3 mmol) and ethyl acetoacetate (49.1 mL, 388.3 mmol) at r.t. with stirring. The mixture was stirred at r.t. for 40 min, and was then refluxed with stirring for 2 h. After cooling to r.t. sat. $NaHCO_3$ solution (200 mL) was added, and the mixture extracted with EtOAc (4×200 mL). The combined organic phases were washed with sat. aq. NaCl solution and water, dried over $MgSO_4$, and concentrated in vacuo. The residue was purified by flash column chromatography on silica gel. Elution with 5-33% EtOAc/$CH_2Cl_2$ gave the title compound as a white solid (41.1 g): MS (m/z) 234.3 (M+1).

b) 5-Methyl-3-phenyl-isothiazole-4-carboxylic acid ethyl ester

To a solution of the 2-(amino-phenyl-methylene)-3-oxobutyric acid ethyl ester (41 g, 170 mmol) in toluene (340 mL) were added $P_2S_5$ (117.3 g, 520 mmol) and tetrachloro-1,4-benzoquinone (43.2 g, 170 mmol) at r.t. with stirring. The mixture was then refluxed with stirring for 15 min. After cooling to r. t. the mixture was filtered and the filtrate was concentrated to give a brown oil, which was purified by flash column chromatography on silica gel. Elution with 5-35% EtOAc/hexanes gave the title compound as a reddish oil (16.7 g): MS (m/z) 248.2 (M+1).

c) N-(2,4-dimethoxy-benzyl),N-(ethyl ethanylat-2-yl)-5-aminomethyl-3-phenyl-isothiazole-4-carboxylic acid ethyl ester To a solution of the 5-methyl-3-phenyl-isothiazole-4-carboxylic acid ethyl ester (14.47 g, 58 mmol) in $CCl_4$ (146 mL) was added N-bromosuccinimide (10.9 g, 61 mmol) and benzoyl peroxide (426 mg, 1.76 mmol). The reaction mixture was refluxed for 18 h. After cooling to r.t. the mixture was filtered. The filtrate was concentrated in vacuo. The residue (11.1 g) was dissolved in DMF (58 mL) and $K_2CO_3$ (7.24 g, 52 mmol) and (2,4-dimethoxy-benzylamino)-acetic acid ethyl ester (9.8 g, 39 mmol) were added. Then the reaction mixture was stirred at r. t. for 20 h. Subsequently, the reaction was quenched by addition of water, and the mixture extracted with EtOAc (3×100 mL). The combined organic layers were washed with brine and water, dried over $MgSO_4$ and concentrated in vacuo. The residue was purified by flash column chromatography on silica gel. Elution with 2-50% EtOAc/hexanes gave the title compound as brown oil (11.1 g): MS (m/z) 499.2 (M+1).

d) 6-(2,4-Dimethoxy-benzyl)-4-oxo-3-phenyl-4,5,6, 7-tetrahydro-isothiazolo[5,4-c]pyridine-5-carboxylic acid ethyl ester To a solution of N-(2,4-dimethoxy-benzyl),N-(ethyl ethanylat-2-yl)-5-aminomethyl-3-phenyl-isothiazole-4-carboxylic acid ethyl ester (11.0 g, 22.0 mmol) in THF (44 mL) was added potassium tert-butoxide (44 mL, 44 mmol, 1.0 M solution in THF) at −78° C. After the reaction mixture was stirred at −78° C. for 30 min, it was allowed to warm to r.t. After 2 h the reaction was quenched with sat. NH$_4$Cl solution and the mixture was then extracted with EtOAc (3×100 mL). The combined organic layers were washed with brine, water, dried over MgSO$_4$, and then concentrated in vacuo. The residue was purified by flash column chromatography on silica gel. Elution with 2-50% EtOAc/hexanes gave the title compound as yellow solid (9.1 g): MS (m/z) 453.1 (M+1).

e) 4-Hydroxy-3-phenyl-isothiazolo[5,4-c]pyridine-5-carboxylic acid ethyl ester To a solution of 6-(2,4-dimethoxy-benzyl)-4-oxo-3-phenyl-4,5,6,7-tetrahydro-isothiazolo[5,4-c]pyridine-5-carboxylic acid ethyl ester (5.42 g, 11.99 mmol) in CH$_2$Cl$_2$ was added SOCl$_2$ (1.31 mL, 17.98 mmol) and the mixture was stirred at r.t. After 3 h the mixture was filtered and the filter cake was washed with hexanes/CH$_2$Cl$_2$ (4/1, 12 mL). The solid was then suspended in sat. NaHCO$_3$ (200 mL) and the mixture extracted with EtOAc (3×200 mL). The combined organic layers were washed with brine, water, dried over MgSO$_4$, and concentrated in vacuo to give the title compound as yellow solid (2.56 g): MS (m/z) 301.1 (M+1).

f) 7-Bromo-4-hydroxy-3-phenyl-isothiazolo[5,4-c]pyridine-5-carboxylic acid ethyl ester To a solution of 4-hydroxy-3-phenyl-isothiazolo[5,4-c]pyridine-5-carboxylic acid ethyl ester (1.07 g, 3.56 mmol) in CCl$_4$ was added N-bromosuccinimide (666 mg, 3.74 mmol) and benzoyl peroxide (43.1 mg, 0.18 mmol). The reaction mixture was refluxed with stirring for 4 h. After cooling to r. t. the mixture was filtered. The filtrate was concentrated in vacuo and purified by flash column chromatography on silica gel. Elution with 0-20% EtOAc/CH$_2$Cl$_2$, gave the title compound as white solid (1.08 g): MS (m/z) 378.9, 380.9 (M+1).

g) 7-(4-Fluoro-phenyl)-4-hydroxy-3-phenyl-isothiazolo[5,4-c]pyridine-5-carboxylic acid ethyl ester A mixture of 7-bromo-4-hydroxy-3-phenyl-isothiazolo[5,4-c]pyridine-5-carboxylic acid ethyl ester (53 mg, 0.139 mmol), Pd(PPh$_3$)$_4$ (16.1 mg, 0.0139 mmol), 4-fluorophenylboronic acid (29.3 mg, 0.209 mmol), K$_2$CO$_3$ (57.8 mg, 0.418 mmol), and 1,4-dioxane (1.39 mL) was heated at 140° C. in a microwave oven with stirring for 5 min. After cooling to r. t., the mixture was filtered and the filter cake was washed with CH$_2$Cl$_2$. The filtrate was concentrated in vacuo and the residue was purified by flash column chromatography on silica gel. Elution with 0-20% EtOAc/CH$_2$Cl$_2$, gave the title compound as a white solid (27.6 mg): MS (m/z) 395.2 (M+1).

h) {[7-(4-Fluoro-phenyl)-4-hydroxy-3-phenyl-isothiazolo[5,4-c]pyridine-5-carbonyl]-amino}-acetic acid A mixture of 7-(4-fluoro-phenyl)-4-hydroxy-3-phenyl-isothiazolo[5,4-c]pyridine-5-carboxylic acid ethyl ester (69 mg, 0.175 mmol), glycine (394 mg, 5.25 mmol), and NaOMe (8.75 mL, 4.37 mmol, 0.5 M solution in MeOH) was refluxed for 24 h. After the mixture was cooled to r. t. it was concentrated in vacuo. The residue was dissolved in water (25 mL) and washed with CH$_2$Cl$_2$ (2×15 mL). The aqueous solution was then acidified by addition of aqueous 1N HCl solution. The resulting precipitate was sucked off, washed with water, and dried in vacuo to give the title compound as white solid (50 mg): MS (m/z) 424.2 (M+1).

Example 2

{[4-Hydroxy-7-(4-methoxy-phenyl)-3-phenyl-isothiazolo[5,4-c]pyridine-5-carbonyl]-amino}-acetic acid a) 4-Hydroxy-7-(4-methoxy-phenyl)-3-phenyl-isothiazolo[5,4-c]pyridine-5-carboxylic acid ethyl ester The title compound was synthesized in analogy to Example 1 from 7-bromo-4-hydroxy-3-phenyl-isothiazolo[5,4-c]pyridine-5-carboxylic acid ethyl ester and 4-methoxyphenylboronic acid: MS (m/z) 407.2 (M+1).

b) {[4-Hydroxy-7-(4-methoxy-phenyl)-3-phenyl-isothiazolo[5,4-c]pyridine-5-carbonyl]-amino}-acetic acid The title compound was synthesized in analogy to Example 1 from 7-(4-methoxy-phenyl)-4-hydroxy-3-phenyl-isothiazolo[5,4-c]pyridine-5-carboxylic acid ethyl ester and glycine: MS (m/z) 436.2 (M+1).

Example 3

[(4-Hydroxy-3-phenyl-7-pyridin-3-yl-isothiazolo[5,4-c]pyridine-5-carbonyl)-amino]-acetic acid a) 4-Hydroxy-3-phenyl-7-pyridin-3-yl-isothiazolo[5,4-c]pyridine-5-carboxylic acid ethyl ester To a solution of 7-bromo-4-hydroxy-3-phenyl-isothiazolo[5,4-c]pyridine-5-carboxylic acid ethyl ester (180 mg, 0.47 mmol) in DMF (2.37 mL) was added 3-(tributylstannyl)pyridine (349 mg, 0.95 mmol) and PdCl$_2$(PPh$_3$)$_2$ (33.3 mg, 0.047 mmol). The reaction mixture was stirred at 120° C. for 30 min. After cooling to r. t. the mixture was partitioned between water (150 mL) and EtOAc (150 mL). The organic layer was washed with brine, water, dried over MgSO$_4$, and concentrated in vacuo. The residue was purified by flash column chromatography on silica gel. Elution with 0-20% EtOAc/CH$_2$Cl$_2$ gave the title compound as white solid (28 mg): MS (m/z) 378.1 (M+1).

b) [(4-Hydroxy-3-phenyl-7-pyridin-3-yl-isothiazolo[5,4-c]pyridine-5-carbonyl)-amino]-acetic acid The title compound was synthesized in analogy to Example 1 from 4-hydroxy-3-phenyl-7-pyridin-3-yl-isothiazolo[5,4-c]pyridine-5-carboxylic acid ethyl ester and glycine: MS (m/z) 407.1 (M+1).

Example 4

[(4-Hydroxy-3-phenyl-7-pyridin-2-yl-isothiazolo[5,4-c]pyridine-5-carbonyl)-amino]-acetic acid a) 4-Hydroxy-3-phenyl-7-pyridin-2-yl-isothiazolo[5,4-c]pyridine-5-carboxylic acid ethyl ester The title compound was synthesized in analogy to Example 3 from 7-bromo-4-hydroxy-3-phenyl-isothiazolo[5,4-c]pyridine-5-carboxylic acid ethyl ester and 2-(tributyl-stannyl)pyridine: MS (m/z) 378.1 (M+1).

b) [(4-Hydroxy-3-phenyl-7-pyridin-2-yl-isothiazolo[5,4-c]pyridine-5-carbonyl)-amino]-acetic acid The title compound was synthesized in analogy to Example 1 from 4-Hydroxy-3-phenyl-7-pyridin-2-yl-isothiazolo[5,4-c]pyridine-5-carboxylic acid ethyl ester and glycine: MS (m/z) 407.1 (M+1).

Example 5

[(4-Hydroxy-3-phenyl-7-pyridin-4-yl-isothiazolo[5,4-c]pyridine-5-carbonyl)-amino]-acetic acid a) 4-Hydroxy-3-phenyl-7-pyridin-4-yl-isothiazolo[5,4-c]pyridine-5-carboxylic acid ethyl ester The title compound was synthesized in analogy to Example 3 from 7-bromo-4-hydroxy-3-phenyl-isothiazolo[5,4-c]pyridine-5-carboxylic acid ethyl ester and 4-(tributyl-stannyl)pyridine: MS (m/z) 378.1 (M+1).

b) [(4-Hydroxy-3-phenyl-7-pyridin-4-yl-isothiazolo[5,4-c]pyridine-5-carbonyl)-amino]-acetic acid The title compound was synthesized in analogy to Example 1 from 4-hydroxy-3-phenyl-7-pyridin-4-yl-isothiazolo[5,4-c]pyridine-5-carboxylic acid ethyl ester and glycine: MS (m/z) 407.1 (M+1).

Example 6

{[7-Ethynyl-3-(4-fluoro-phenyl)-4-hydroxy-isothiazolo[5,4-c]pyridine-5-carbonyl]-amino}-acetic acid a) 2-[Amino-(4-fluoro-phenyl)-methylene]-3-oxo-butyric acid ethyl ester

The title compound was synthesized in analogy to Example 1 from 4-fluorobenzonitrile and ethyl acetoacetate: MS (m/z) 252.2 (M+1).

b) 3-(4-Fluoro-phenyl)-5-methyl-isothiazole-4-carboxylic acid ethyl ester

The title compound was synthesized in analogy to Example 1 from 2-(amino-4-fluoro-phenyl-methylene)-3-oxo-butyric acid ethyl ester: MS (m/z) 266.2 (M+1).

c) N-(2,4-dimethoxy-benzyl),N-(ethyl ethanylat-2-yl)-5-aminomethyl-3-(4-fluoro-phenyl)-isothiazole-4-carboxylic acid ethyl ester The title compound was synthesized in analogy to Example 1 from 3-(4-fluoro-phenyl)-5-methyl-isothiazole-4-carboxylic acid ethyl ester: MS (m/z) 517.3 (M+1).

d) 6-(2,4-Dimethoxy-benzyl)-3-(4-fluoro-phenyl)-4-oxo-4,5,6,7-tetrahydro-isothiazolo[5,4-c]pyridine-5-carboxylic acid ethyl ester The title compound was synthesized in analogy to Example 1 from N-(2,4-dimethoxy-benzyl),N-(ethyl ethanylat-2-yl)-5-aminomethyl-3-(4-fluoro-phenyl)-isothiazole-4-carboxylic acid ethyl ester: MS (m/z) 471.2 (M+1).

e) 3-(4-Fluoro-phenyl)-4-hydroxy-isothiazolo[5,4-c]pyridine-5-carboxylic acid ethyl ester The title compound was synthesized in analogy to Example 1 from 6-(2,4-dimethoxy-benzyl)-3-(4-fluoro-phenyl)-4-oxo-4,5,6,7-tetrahydro-isothiazolo[5,4-c]pyridine-5-carboxylic acid ethyl ester: MS (m/z) 319.2 (M+1).

f) 7-Bromo-3-(4-fluoro-phenyl)-4-hydroxy-isothiazolo[5,4-c]pyridine-5-carboxylic acid ethyl ester The title compound was synthesized in analogy to Example 1 from 3-(4-fluoro-phenyl)-4-hydroxy-isothiazolo[5,4-c]pyridine-5-carboxylic acid ethyl ester: MS (m/z) 396.9, 398.9 (M+1).

g) 3-(4-Fluoro-phenyl)-4-hydroxy-7-trimethylsilanylethynyl-isothiazolo[5,4-c]pyridine-5-carboxylic acid ethyl ester To a solution of 7-Bromo-3-(4-fluoro-phenyl)-4-hydroxy-isothiazolo[5,4-c]pyridine-5-carboxylic acid ethyl ester (124.9 mg, 0.39 mmol) in THF (5.6 mL) was added trimethylsilylacetylene (0.11 mL, 0.78 mmol), PdCl$_2$(PPh$_3$)$_2$ (55.1 mg, 0.078 mmol), CuI (29.9 mg, 0.156 mmol) and isopropylamine (0.34 mL, 2.42 mmol). The reaction mixture refluxed for 16 h with stirring. After cooling to r. t. the mixture was diluted with EtOAc (20 mL), filtered and the filter cake washed with EtOAc (10 mL). The filtrate was concentrated in vacuo. The residue was purified by flash column chromatography on silica gel. Elution with 0-20% EtOAc/CH$_2$Cl$_2$ gave the title compound as white solid (57 mg): MS (m/z) 415.1 (M+1).

h) {[7-Ethynyl-3-(4-fluoro-phenyl)-4-hydroxy-isothiazolo[5,4-c]pyridine-5-carbonyl]-amino}-acetic acid The title compound was synthesized in analogy to Example 1 from 3-(4-fluoro-phenyl)-4-hydroxy-7-trimethylsilanylethynyl-isothiazolo[5,4-c]pyridine-5-carboxylic acid ethyl ester and glycine: MS (m/z) 370.1 (M−1).

Example 7

{[7-Bromo-3-(4-fluoro-phenyl)-4-hydroxy-isothiazolo[5,4-c]pyridine-5-carbonyl]-amino}-acetic acid The title compound was synthesized in analogy to Example 1 from 7-bromo-3-(4-fluoro-phenyl)-4-hydroxyisothiazolo[5,4-c]pyridine-5-carboxylic acid ethyl ester and glycine: MS (m/z) 423.9, 426.0 (M−1).

Example 8

{[7-Cyano-3-(4-fluoro-phenyl)-4-hydroxy-isothiazolo[5,4-c]pyridine-5-carbonyl]-amino}-acetic acid A mixture of {[7-bromo-3-(4-fluoro-phenyl)-4-hydroxy-isothiazolo[5,4-c]pyridine-5-carbonyl]-amino}-acetic acid (105 mg, 0.246 mmol), Pd$_2$(dba)$_3$ (22.5 mg, 0.0246 mmol), dppf (27.2 mg, 0.0492 mmol), Zn(CN)$_2$ (28.9 mg, 0.246 mmol), Zn dust (1.6 mg, 0.0246 mmol), and DMA (0.49 mL) was stirred at 120° C. for 1 h. After cooling to r.t. the mixture was concentrated in vacuo. The residue was purified by flash column chromatography on silica gel. Elution with 0-20% MeOH/CH$_2$Cl$_2$/0.1% HCOOH gave the title compound as a white solid (21.8 mg): MS (m/z) 371.1 (M−1).

Example 9

{[3-(4-Fluoro-phenyl)-4-hydroxy-7-methyl-isothiazolo[5,4-c]pyridine-5-carbonyl]-amino}-acetic acid a) 3-(4-fluoro-phenyl)-4-hydroxy-7-iodo-isothiazolo[5,4-c]pyridine-5-carboxylic acid ethyl ester To a solution of 3-(4-fluoro-phenyl)-4-hydroxy-isothiazolo[5,4-c]pyridine-5-carboxylic acid ethyl ester (400 mg, 1.25 mmol) in CH$_2$Cl$_2$ (12.5 mL) was added bis(2,4,6-trimethylpyridine)iodine(I) hexafluorophosphate (1.29 g, 2.51 mmol). The reaction mixture was allowed to stir at r.t. for 20 h. Then the mixture was filtered and the filtrate was concentrated in vacuo. The residue was purified by flash column chromatography on silica gel. Elution with 0-20% EtOAc/CH$_2$Cl$_2$, gave the title product (382 mg) as a yellow solid: MS (m/z) 442.9 (M−1).

b) 3-(4-Fluoro-phenyl)-4-hydroxy-7-methyl-isothiazolo[5,4-c]pyridine-5-carboxylic acid ethyl ester A mixture of 3-(4-fluoro-phenyl)-4-hydroxy-7-iodo-isothiazolo[5,4-c]pyridine-5-carboxylic acid ethyl ester (295 mg, 0.66 mmol), Pd$_2$(dba)$_3$ (60.8 mg, 0.066 mmol), PPh$_3$ (17.4 mg, 0.066 mmol), and NMP (3.3 mL) was stirred at 70° C. for 10 min. After cooling to r. t. CuI (12.6 mg, 0.066 mmol) was added and the reaction mixture was stirred at 70° C. for another 10 min. After cooling to r. t. Me$_4$Sn (0.37 mL, 2.65 mmol) was added and the mixture was stirred at 70° C. for 15 h. After cooling to r. t. the mixture was partitioned between 1 M HCl (28 mL) and EtOAc (60 mL). The organic layer was washed with brine, water, dried over MgSO$_4$, and was then concentrated in vacuo. The residue was purified by flash column chromatography on silica gel. Elution with 0-20% EtOAc/CH$_2$Cl$_2$, gave the title compound as a white solid (117 mg): MS (m/z) 333.2 (M+1).

c) {[3-(4-Fluoro-phenyl)-4-hydroxy-7-methyl-isothiazolo[5,4-c]pyridine-5-carbonyl]-amino}-acetic acid The title compound was synthesized in analogy to Example 1 from 3-(4-Fluoro-phenyl)-4-hydroxy-7-methyl-isothiazolo[5,4-c]pyridine-5-carboxylic acid ethyl ester and glycine: MS (m/z) 360.1 (M−1).

Example 10

{[3-(4-Fluoro-phenyl)-4-hydroxy-7-phenyl-isothiazolo[5,4-c]pyridine-5-carbonyl]-amino}-acetic acid a) 3-(4-Fluoro-phenyl)-4-hydroxy-7-phenyl-isothiazolo[5,4-c]pyridine-5-carboxylic acid ethyl ester The title compound was synthesized in analogy to Example 1 from 7-bromo-3-(4-fluoro-phenyl)-4-hydroxy-isothiazolo[5,4-c]pyridine-5-carboxylic acid ethyl ester and phenylboronic acid: MS (m/z) 395.2 (M+1).

b) {[3-(4-Fluoro-phenyl)-4-hydroxy-7-phenyl-isothiazolo[5,4-c]pyridine-5-carbonyl]-amino}-acetic acid The title compound was synthesized in analogy to Example 1 from 3-(4-Fluoro-phenyl)-4-hydroxy-7-phenyl-isothiazolo[5,4-c]pyridine-5-carboxylic acid ethyl ester and glycine: MS (m/z) 422.1 (M−1).

Example 11

{[7-(4-Cyano-phenyl)-3-(4-fluoro-phenyl)-4-hydroxy-isothiazolo[5,4-c]pyridine-5-carbonyl]-amino}-acetic acid a) 7-(4-Cyano-phenyl)-3-(4-fluoro-phenyl)-4-hydroxy-isothiazolo[5,4-c]pyridine-5-carboxylic acid ethyl ester The title compound was synthesized in analogy to Example 1 from 7-bromo-3-(4-fluoro-phenyl)-4-hydroxy-isothiazolo[5,4-c]pyridine-5-carboxylic acid ethyl ester and 4-cyanophenylboronic acid: MS (m/z) 420.2 (M+1).

b) {[7-(4-Cyano-phenyl)-3-(4-fluoro-phenyl)-4-hydroxy-isothiazolo[5,4-c]pyridine-5-carbonyl]-amino}-acetic acid The title compound was synthesized in analogy to Example 1 from 7-(4-cyano-phenyl)-3-(4-fluoro-phenyl)-4-hydroxy-isothiazolo[5,4-c]pyridine-5-carboxylic acid ethyl ester and glycine: MS (m/z) 447.1 (M−1).

Example 12

{[3-(4-Fluoro-phenyl)-4-hydroxy-isothiazolo[5,4-c]pyridine-5-carbonyl]-amino}-acetic acid A mixture of 3-(4-Fluoro-phenyl)-4-hydroxy-isothiazolo[5,4-c]pyridine-5-carboxylic acid ethyl ester (150 mg, 0.47 mmol), glycine (1.06 g, 14.1 mmol), and NaOMe (23.5 mL, 11.75 mmol, 0.5 M solution in MeOH) was refluxed for 24 h. After cooling to r.t. the mixture was concentrated in vacuo. The residue was dissolved in water (50 mL), and the solution washed with CH$_2$Cl$_2$ (2×30 mL) before it was acidified by addition of aqueous 1N HCl solution. The resulting precipitate was sucked off, washed with water, and dried in vacuo to give the title compound (146 mg) as white solid: MS (m/z) 346.1 (M−1)$^+$.

Example 13

{[3-(4-Chloro-phenyl)-4-hydroxy-7-(4-methoxy-phenyl)-isothiazolo[5,4-c]pyridine-5-carbonyl]-amino}-acetic acid a) 2-[Amino-(4-chloro-phenyl)-methylene]-3-oxo-butyric acid ethyl ester

The title compound was synthesized in analogy to Example 1 from 4-chlorobenzonitrile and ethyl acetoacetate: MS (m/z) 268.2 (M+1).

b) 3-(4-Chloro-phenyl)-5-methyl-isothiazole-4-carboxylic acid ethyl ester

The title compound was synthesized in analogy to Example 1 from 2-(amino-4-chloro-phenyl-methylene)-3-oxo-butyric acid ethyl ester: MS (m/z) 282.2 (M+1).

c) N-(2,4-dimethoxy-benzyl),N-(ethyl ethanylat-2-yl)-5-aminomethyl-3-(4-chloro-phenyl)-isothiazole-4-carboxylic acid ethyl ester The title compound was synthesized in analogy to Example 1 from 3-(4-Chloro-phenyl)-5-methyl-isothiazole-4-carboxylic acid ethyl ester: MS (m/z) 533.1 (M+1).

d) 3-(4-Chloro-phenyl)-6-(2,4-dimethoxy-benzyl)-4-oxo-4,5,6,7-tetrahydro-isothiazolo[5,4-c]pyridine-5-carboxylic acid ethyl ester The title compound was synthesized in analogy to Example 1 from N-(2,4-dimethoxy-benzyl),N-(ethyl ethanylat-2-yl)-5-aminomethyl-3-(4-chloro-phenyl)-isothiazole-4-carboxylic acid ethyl ester: MS (m/z) 487.1 (M+1).

e) 3-(4-Chloro-phenyl)-4-hydroxy-isothiazolo[5,4-c]pyridine-5-carboxylic acid ethyl ester The title compound was synthesized in analogy to Example 1 from 3-(4-Chloro-phenyl)-6-(2,4-dimethoxy-benzyl)-4-oxo-4,5,6,7-tetrahydro-isothiazolo[5,4-c]pyridine-5-carboxylic acid ethyl ester: MS (m/z) 335.1 (M+1).

f) 7-Bromo-3-(4-chloro-phenyl)-4-hydroxy-isothiazolo[5,4-c]pyridine-5-carboxylic acid ethyl ester The title compound was synthesized in analogy to Example 1 from 3-(4-Chloro-phenyl)-4-hydroxy-isothiazolo[5,4-c]pyridine-5-carboxylic acid ethyl ester: MS (m/z) 412.9, 415.0 (M+1).

g) 3-(4-Chloro-phenyl)-4-hydroxy-7-(4-methoxy-phenyl)-isothiazolo[5,4-c]pyridine-5-carboxylic acid ethyl ester The title compound was synthesized in analogy to Example 1 from 7-bromo-3-(4-chloro-phenyl)-4-hydroxy-isothiazolo[5,4-c]pyridine-5-carboxylic acid ethyl ester: MS (m/z) 441.1 (M+1).

h) {[3-(4-Chloro-phenyl)-4-hydroxy-7-(4-methoxy-phenyl)-isothiazolo[5,4-c]pyridine-5-carbonyl]-amino}-acetic acid The title compound was synthesized in analogy to Example 1 from 3-(4-Chloro-phenyl)-4-hydroxy-7-(4-methoxy-phenyl)-isothiazolo[5,4-c]pyridine-5-carboxylic acid ethyl ester and glycine: MS (m/z) 470.0 (M+1).

Example 14

{[3-(4-Chloro-phenyl)-7-ethynyl-4-hydroxy-isothiazolo[5,4-c]pyridine-5-carbonyl]-amino}-acetic acid a) 3-(4-Chloro-phenyl)-4-hydroxy-7-trimethylsilanylethynyl-isothiazolo[5,4-c]pyridine-5-carboxylic acid ethyl ester To a solution of 7-Bromo-3-(4-chloro-phenyl)-4-hydroxy-isothiazolo[5,4-c]pyridine-5-carboxylic acid ethyl ester (152.5 mg, 0.369 mmol) in THF (5.2 mL) were added Trimethylsilylacetylene (0.105 mL, 0.738 mmol), PdCl$_2$(PPh$_3$)$_2$ (51.8 mg, 0.0738 mmol), CuI (28.1 mg, 0.147 mmol) and isopropylamine (0.32 mL, 2.28 mmol). The reaction mixture was refluxed for 16 h. After cooling to rt, the mixture was diluted with EtOAc (20 mL), and filtered. The filtrate was concentrated in vacuo and purified by flash chromatography on silica gel. Elution with 0-20% EtOAc/CH$_2$Cl$_2$, gave the desired product (60 mg) as white solid: MS (m/z) 431.1 (M+1).

b) {[3-(4-Chloro-phenyl)-7-ethynyl-4-hydroxy-isothiazolo[5,4-c]pyridine-5-carbonyl]-amino}-acetic acid A mixture of 3-(4-Chloro-phenyl)-4-hydroxy-7-trimethylsilanylethynyl-isothiazolo[5,4-c]pyridine-5-carboxylic acid ethyl ester (51.5 mg, 0.119 mmol), glycine (269.7 mg, 3.59 mmol) and NaOMe (5.98 mL, 2.99 mmol, 0.5 M solution in MeOH) was refluxed for 24 h before it was concentrated in vacuo. The residue was dissolved in water (50 mL). The solution was then washed with CH$_2$Cl$_2$ (2×20 mL) before it was acidified by addition on aqueous 1N HCl solution. The resulting precipitate was sucked off, washed with water, and dried in vacuo to give the title compound (40 mg) as white solid: MS (m/z) 388.0 (M+1).

Example 15

{[3-(4-Chloro-phenyl)-4-hydroxy-7-methyl-isothiazolo[5,4-c]pyridine-5-carbonyl]-amino}-acetic acid a) 3-(4-Chloro-phenyl)-4-hydroxy-7-iodo-isothiazolo[5,4-c]pyridine-5-carboxylic acid ethyl ester The title compound was synthesized in analogy to Example 9 from 3-(4-Chloro-phenyl)-4-hydroxy-isothiazolo[5,4-c]pyridine-5-carboxylic acid ethyl ester: MS (m/z) 460.9 (M+1).

b) 3-(4-Chloro-phenyl)-4-hydroxy-7-methyl-isothiazolo[5,4-c]pyridine-5-carboxylic acid ethyl ester The title compound was synthesized in analogy to Example 9 from 3-(4-Chloro-phenyl)-4-hydroxy-7-iodo-isothiazolo[5,4-c]pyridine-5-carboxylic acid ethyl ester: MS (m/z) 349.1 (M+1).

c) {[3-(4-Chloro-phenyl)-4-hydroxy-7-methyl-isothiazolo[5,4-c]pyridine-5-carbonyl]-amino}-acetic acid The title compound was synthesized in analogy to Example 1 from 3-(4-Chloro-phenyl)-4-hydroxy-7-methyl-isothiazolo[5,4-c]pyridine-5-carboxylic acid ethyl ester: MS (m/z) 376.0 (M−1).

Example 16

{[3-(4-Chloro-phenyl)-4-hydroxy-isothiazolo[5,4-c]pyridine-5-carbonyl]-amino}-acetic acid The title compound was synthesized in analogy to Example 1 from 3-(4-Chloro-phenyl)-4-hydroxy-isothiazolo[5,4-c]pyridine-5-carboxylic acid ethyl ester: MS (m/z) 362.1 (M−1).

Example 17

{[3-(4-Chloro-phenyl)-4-hydroxy-7-phenyl-isothiazolo[5,4-c]pyridine-5-carbonyl]-amino}-acetic acid a) 3-(4-Chloro-phenyl)-4-hydroxy-7-phenyl-isothiazolo[5,4-c]pyridine-5-carboxylic acid ethyl ester The title compound was synthesized in analogy to Example 1 from 7-Bromo-3-(4-chloro-phenyl)-4-hydroxy-isothiazolo[5,4-c]pyridine-5-carboxylic acid ethyl ester and phenylboronic acid: MS (m/z) 411.1 (M+1).

b) {[3-(4-Chloro-phenyl)-4-hydroxy-7-phenyl-isothiazolo[5,4-c]pyridine-5-carbonyl]-amino}-acetic acid The title compound was synthesized in analogy to Example 1 from 3-(4-Chloro-phenyl)-4-hydroxy-7-phenyl-isothiazolo[5,4-c]pyridine-5-carboxylic acid ethyl ester: MS (m/z) 438.0 (M−1).

Example 18

(R)-2-{[3-(4-Chloro-phenyl)-4-hydroxy-isothiazolo[5,4-c]pyridine-5-carbonyl]-amino}-propionic acid A mixture of 3-(4-Chloro-phenyl)-4-hydroxy-isothiazolo[5,4-c]pyridine-5-carboxylic acid ethyl ester (50 mg, 0.149 mmol), D-alanine (400 mg, 4.49 mmol) and NaOMe (7.45 mL, 3.72 mmol, 0.5 M solution in MeOH) was refluxed for 48 h before it was concentrated in vacuo. The residue was dissolved in water (50 mL) and washed with $CH_2Cl_2$ (2×20 mL). The aqueous solution was then acidified by addition of 1N HCl solution. The resulting precipitate was sucked off, washed with water, and dried in vacuo to give the title compound as a white solid (39.2 mg): MS (m/z) 376.0 (M−1).

Example 19

(S)-2-{[3-(4-Chloro-phenyl)-4-hydroxy-isothiazolo[5,4-c]pyridine-5-carbonyl]-amino}-propionic acid The title compound was synthesized in analogy to Example 18 from 3-(4-Chloro-phenyl)-4-hydroxy-isothiazolo[5,4-c]pyridine-5-carboxylic acid ethyl ester: MS (m/z) 378.0 (M+1).

Example 20

{[3-(4-Chloro-phenyl)-4-hydroxy-7-(3-methoxy-phenyl)-isothiazolo[5,4-c]pyridine-5-carbonyl]-amino}-acetic acid a) 3-(4-Chloro-phenyl)-4-hydroxy-7-(3-methoxy-phenyl)-isothiazolo[5,4-c]pyridine-5-carboxylic acid ethyl ester The title compound was synthesized in analogy to Example 1 from 7-Bromo-3-(4-chloro-phenyl)-4-hydroxy-isothiazolo[5,4-c]pyridine-5-carboxylic acid ethyl ester and 3-methoxyphenylboronic acid: MS (m/z) 441.1 (M+1).

b) {[3-(4-Chloro-phenyl)-4-hydroxy-7-(3-methoxy-phenyl)-isothiazolo[5,4-c]pyridine-5-carbonyl]-amino}-acetic acid The title compound was synthesized in analogy to Example 1 from 3-(4-Chloro-phenyl)-4-hydroxy-7-(3-methoxy-phenyl)-isothiazolo[5,4-c]pyridine-5-carboxylic acid ethyl ester: MS (m/z) 468.0 (M−1).

Example 21

{[3-(4-Chloro-phenyl)-4-hydroxy-7-(6-methoxy-pyridin-3-yl)-isothiazolo[5,4-c]pyridine-5-carbonyl]-amino}-acetic acid a) 3-(4-Chloro-phenyl)-4-hydroxy-7-(6-methoxy-pyridin-3-yl)-isothiazolo[5,4-c]pyridine-5-carboxylic acid ethyl ester The title compound was synthesized in analogy to Example 1 from 7-bromo-3-(4-chloro-phenyl)-4-hydroxy-isothiazolo[5,4-c]pyridine-5-carboxylic acid ethyl ester and 2-methoxy-5-pyridineboronic acid: MS (m/z) 440.1 (M−1).

b) {[3-(4-Chloro-phenyl)-4-hydroxy-7-(6-methoxy-pyridin-3-yl)-isothiazolo[5,4-c]pyridine-5-carbonyl]-amino}-acetic acid The title compound was synthesized in analogy to Example 1 from 3-(4-chloro-phenyl)-4-hydroxy-7-(6-methoxy-pyridin-3-yl)-isothiazolo[5,4-c]pyridine-5-carboxylic acid ethyl ester: MS (m/z) 469.0 (M−1).

Example 22

{[7-Benzyl-3-(4-chloro-phenyl)-4-hydroxy-isothiazolo[5,4-c]pyridine-5-carbonyl]-amino}-acetic acid a) 7-Benzyl-3-(4-chloro-phenyl)-4-hydroxy-isothiazolo[5,4-c]pyridine-5-carboxylic acid ethyl ester The title compound was synthesized in analogy to Example 1 from 7-bromo-3-(4-chloro-phenyl)-4-hydroxy-isothiazolo[5,4-c]pyridine-5-carboxylic acid ethyl ester and benzylboronic acid: MS (m/z) 425.1 (M+1).

b) {[7-Benzyl-3-(4-chloro-phenyl)-4-hydroxy-isothiazolo[5,4-c]pyridine-5-carbonyl]-amino}-acetic acid The title compound was synthesized in analogy to Example 1 from 7-benzyl-3-(4-chloro-phenyl)-4-hydroxy-isothiazolo[5,4-c]pyridine-5-carboxylic acid ethyl ester: MS (m/z) 454.1 (M+1).

Example 23

{[7-(1-Benzyl-1H-[1,2,3]triazol-4-yl)-3-(4-chloro-phenyl)-4-hydroxy-isothiazolo[5,4-c]pyridine-5-carbonyl]-amino}-acetic acid a) 3-(4-Chloro-phenyl)-7-ethynyl-4-hydroxy-isothiazolo[5,4-c]pyridine-5-carboxylic acid ethyl ester To a solution of 3-(4-chloro-phenyl)-4-hydroxy-7-trimethylsilanylethynyl-isothiazolo[5,4-c]pyridine-5-carboxylic acid ethyl ester (0.189 mmol) in EtOH/$CH_2Cl_2$ (1/1, 0.76 mL) was added $Cs_2CO_3$ (0.227 mmol) with stirring at r.t. After 16 h the mixture was partitioned between 1N HCl (10 mL) and EtOAc (10 mL). The aqueous phase was extracted with EtOAc (2×10 mL). The combined organic layers were washed with brine and water, dried over $MgSO_4$ and concentrated in vacuo. The residue was purified by flash column chromatography on silica gel, eluting with 0-20% EtOAc/$CH_2Cl_2$, to give the title compound (38 mg) as a white solid: MS (m/z) 357.0 (M−1).

b) 7-(1-Benzyl-1H-[1,2,3]triazol-4-yl)-3-(4-chloro-phenyl)-4-hydroxy-isothiazolo[5,4-c]pyridine-5-carboxylic acid ethyl ester To a mixture of 3-(4-chloro-phenyl)-7-ethynyl-4-hydroxy-isothiazolo[5,4-c]pyridine-5-carboxylic acid ethyl ester (0.106 mmol) and $CH_2Cl_2/H_2O$ (1/1, 0.70 mL) was added benzylazide (0.117 mmol), $CuSO_4 \cdot 5H_2O$ (0.0053 mmol) and sodium L-ascorbate (0.0159 mmol). The mixture was stirred at rt for 16 h before it was partitioned between $H_2O$ (20 mL) and $CH_2Cl_2$ (20 mL). The aqueous phase was then extracted with $CH_2Cl_2$ (2×15 mL). The combined organic layers were washed with brine and water, dried over $MgSO_4$ and concentrated in vacuo. The residue was purified by flash column chromatography on silica gel, eluting with 0-20% EtOAc/$CH_2Cl_2$, to give the title compound (40 mg) as a white solid: MS (m/z) 492.1 (M+1).

c) {[7-(1-Benzyl-1H-[1,2,3]triazol-4-yl)-3-(4-chloro-phenyl)-4-hydroxy-isothiazolo[5,4-c]pyridine-5-carbonyl]-amino}-acetic acid The title compound was synthesized in analogy to Example 1 from 7-(1-benzyl-1H-[1,2,3]triazol-4-yl)-3-(4-chloro-phenyl)-4-hydroxy-isothiazolo[5,4-c]pyridine-5-carboxylic acid ethyl ester: MS (m/z) 519.0 (M−1).

Example 24

{[3-(4-Chloro-phenyl)-4-hydroxy-7-naphthalen-1-yl-isothiazolo[5,4-c]pyridine-5-carbonyl]-amino}-acetic acid a) 3-(4-Chloro-phenyl)-4-hydroxy-7-naphthalen-1-yl-isothiazolo[5,4-c]pyridine-5-carboxylic acid ethyl ester The title compound was synthesized in analogy to Example 1 from 7-bromo-3-(4-chloro-phenyl)-4-hydroxy-isothiazolo[5,4-c]pyridine-5-carboxylic acid ethyl ester and 1-naphthylboronic acid: MS (m/z) 461.0 (M+1).

b) {[3-(4-Chloro-phenyl)-4-hydroxy-7-naphthalen-1-yl-isothiazolo[5,4-c]pyridine-5-carbonyl]-amino}-acetic acid The title compound was synthesized in analogy to Example 1 from 3-(4-chloro-phenyl)-4-hydroxy-7-naphthalen-1-yl-isothiazolo[5,4-c]pyridine-5-carboxylic acid ethyl ester: MS (m/z) 490.0 (M+1).

Example 25

{[7-Acetyl-3-(4-chloro-phenyl)-4-hydroxy-isothiazolo[5,4-c]pyridine-5-carbonyl]-amino}-acetic acid To the solution of {[3-(4-chloro-phenyl)-7-ethynyl-4-hydroxy-isothiazolo[5,4-c]pyridine-5-carbonyl]-amino}-acetic acid (0.28 mmol) in actone/water=4:1 (2.8 mL) was added conc. $H_2SO_4$ (36.2 mg, 0.37 mmol) and $HgSO_4$ (84.3 mg, 0.28 mmol). The reaction mixture was refluxed for 2 h. After cooling to r.t. the mixture was concentrated in vacuo. The residue was dissolved in DMSO (2.5 mL) and purified by flash column chromatography on C18 (40 g), eluting with 30-80% $CH_3CN/H_2O$ in 0.1% HCOOH to give the title compound (26 mg) as a brown solid: MS (m/z) 406.0 (M+1).

Example 26

{[3-(4-Chloro-phenyl)-4-hydroxy-7-trifluoromethyl-isothiazolo[5,4-c]pyridine-5-carbonyl]-amino}-acetic acid a) 3-(4-Chloro-phenyl)-4-(2,2-dimethyl-propionyloxy)-7-iodo-isothiazolo[5,4-c]pyridine-5-carboxylic acid ethyl ester To a solution of 3-(4-chloro-phenyl)-4-hydroxy-7-iodo-isothiazolo[5,4-c]pyridine-5-carboxylic acid ethyl ester (0.47 mmol) in $CH_2Cl_2$ (2.38 mL) was added trimethylacetyl chloride (0.57 mmol) and $Et_3N$ (0.71 mmol). The reaction mixture was stirred at r.t. for 2 h before the mixture was filtered. The filtrate was concentrated in vacuo and the residue purified by flash column chromatography on silica gel. Eluting with 0-20% EtOAc/$CH_2Cl_2$, gave the title compound (225 mg) as a white solid: MS (m/z) 544.9 (M+1).

b) 3-(4-Chloro-phenyl)-4-hydroxy-7-trifluoromethyl-isothiazolo[5,4-c]pyridine-5-carboxylic acid ethyl ester To a solution of 3-(4-Chloro-phenyl)-4-(2,2-dimethyl-propionyloxy)-7-iodo-isothiazolo[5,4-c]pyridine-5-carboxylic acid ethyl ester (0.41 mmol) in DMF (2.05 mL) was added copper iodide (1.24 mmol) and methyl 2,2-difluoro-2-(fluorosulfonyl)acetate (2.06 mmol). The reaction mixture was stirred at 70° C. for 15 h before the mixture was partitioned between water (100 mL) and EtOAc (100 mL). The organic layer was washed with brine and water before it was dried over $MgSO_4$ and concentrated in vacuo. The residue was purified by flash column chromatography on silica gel. Eluting with 2-50% EtOAc/hexanes gave the title compound (27.7 mg) as a white solid: MS (m/z) 403.0 (M+1).

c) {[3-(4-Chloro-phenyl)-4-hydroxy-7-trifluoromethyl-isothiazolo[5,4-c]pyridine-5-carbonyl]-amino}-acetic acid The title compound was synthesized in analogy to Example 1 from 3-(4-Chloro-phenyl)-4-hydroxy-7-trifluoromethyl-isothiazolo[5,4-c]pyridine-5-carboxylic acid ethyl ester: MS (m/z) 432.0 (M+1).

Example 27

[(4-Bromo-7-hydroxy-3-phenyl-isothiazolo[4,5-c]pyridine-6-carbonyl)-amino]-acetic acid a) 5-Phenyl-[1,3,4]oxathiazol-2-one To a solution of benzamide (66.03 mmol) in toluene (132 mL) was added chlorocarbonylsulfenyl chloride (82.4 mmol). The reaction mixture was stirred at 100° C. for 4 h. After cooling to r.t. the reaction mixture was concentrated in vacuo, and the residue was crystallized from EtOAc to give the title compound (9.43 g) as a white solid: MS (m/z) 179.1 (M+1).

b) 3-Phenyl-isothiazole-4,5-dicarboxylic acid dimethyl ester

A solution of 5-phenyl-[1,3,4]oxathiazol-2-one (30.33 mmol) and dimethylacetylenedicarboxylate (60.67 mmol) in chlorobenzene (17.8 mL) was refluxed with stirring for 6 h before it was concentrated in vacuo. The residue was crystallized from cold MeOH to give the title compound (5.0 g) as a slightly yellow solid: MS (m/z) 278.1 (M+1).

c) 3-Phenyl-isothiazole-4,5-dicarboxylic acid 5-methyl ester and 3-Phenyl-isothiazole-4,5-dicarboxylic acid 4-methyl ester To a solution of 3-Phenyl-isothiazole-4,5-dicarboxylic acid dimethyl ester (18.05 mmol) in THF (17.5 mL) and MeOH (7.2 mL) was added 2N NaOH solution (9.02 mL). After the reaction mixture was stirred at r.t. for 90 min, it was partitioned between water and methyl 1-tert-butyl ether. The aqueous layer was acidified by addition of 1N HCl to pH=2, and then extracted with EtOAc (3×80 mL). The combined organic layers were washed with brine and water, dried over $MgSO_4$, and concentrated in vacuo to give a mixture of the title compounds (4.44 g) as a yellow solid: MS (m/z) 264.1 (M+1).

d) N-(2-Methoxy-2-oxoethyl)-4-carbamoyl-3-phenyl-isothiazole-5-carboxylic acid methyl ester and N-(2-Methoxy-2-oxoethyl)-5-carbamoyl-3-phenyl-isothiazole-4-carboxylic acid methyl ester To a solution of 3-phenyl-isothiazole-4,5-dicarboxylic acid 5-methyl ester and 3-phenyl-isothiazole-4,5-dicarboxylic acid 4-methyl ester (16.88 mmol) in $CH_2Cl_2$ (42 mL) was added oxalyl chloride (33.76 mmol) and three drops of DMF at 0° C. The reaction mixture was stirred at 0° C. for 5 min, and then allowed to stir at r.t. for 1 h. Then the solvent was removed in vacuo. To a solution of the residue in $CH_2Cl_2$ (42 mL) was added glycine methyl ester hydrochloride (33.76 mmol) and $Et_3N$ (50.64 mmol) at 0° C. The reaction mixture was allowed to warm to r.t. overnight, and was subsequently quenched with 0.5 N HCl (30 mL). The organic layer was washed with brine and water, dried over $MgSO_4$, and concentrated in vacuo. The residue was purified by flash column chromatography on silica gel. Eluting with 0-20% EtOAc/$CH_2Cl_2$ gave a mixture of the title compounds (4.52 g) as a white solid: MS (m/z) 335.1 (M+1).

f) 4,7-Dihydroxy-3-phenyl-isothiazolo[5,4-c]pyridine-5-carboxylic acid butyl ester, 4,7-Dihydroxy-3-phenyl-isothiazolo[4,5-c]pyridine-6-carboxylic acid butyl ester, 4,7-Dihydroxy-3-phenyl-isothiazolo[5,4-c]pyridine-5-carboxylic acid methyl ester, and 4,7-Dihydroxy-3-phenyl-isothiazolo[4,5-c]pyridine-6-carboxylic acid methyl ester To a solution of N-(2-methoxy-2-oxoethyl)-4-carbamoyl-3-phenyl-isothiazole-5-carboxylic acid methyl ester and N-(2-methoxy-2-oxoethyl)-5-carbamoyl-3-phenyl-isothiazole-4-carboxylic acid methyl ester (10.56 mmol) in 1-BuOH (30 mL) was added sodium tert-butoxide (23.25 mmol). The reaction mixture was stirred at 110° C. for 50 min. After cooling to r.t. the mixture was acidified by addition of 1 N HCl to pH=2. The mixture was filtered, the filter cake washed with water (100 mL) and dried in vacuo to give a mixture of the title compounds (2.23 g): MS (m/z) 345.1 (M+1) (butyl ester), MS (m/z) 303.1 (M+1) (methyl ester).

g) 4-Bromo-7-hydroxy-3-phenyl-isothiazolo[4,5-c]pyridine-6-carboxylic acid butyl ester To a solution of the 4,7-dihydroxy-3-phenyl-isothiazolo[5,4-c]pyridine-5-carboxylic acid butyl ester, 4,7-dihydroxy-3-phenyl-isothiazolo[4,5-c]pyridine-6-carboxylic acid butyl ester, 4,7-dihydroxy-3-phenyl-isothiazolo[5,4-c]pyridine-5-carboxylic acid methyl ester, and 4,7-dihydroxy-3-phenyl-isothiazolo[4,5-c]pyridine-6-carboxylic acid methyl ester mixture obtained above (1.14 g) in dichloroethane (16.5 mL) was added $POBr_3$ (3.97 mmol). The reaction mixture was stirred at 120° C. in a microwave oven for 35 min. After cooling to r.t. the mixture was partitioned between $CH_2Cl_2$ and sat. $NaHCO_3$ and filtered. The organic layer was washed with brine, dried over $MgSO_4$ and concentrated in vacuo. The residue was purified by flash column chromatography on silica gel. Eluting with 0-20% EtOAc/$CH_2Cl_2$, gave the title compound (40 mg) as a white solid: MS (m/z) 405.0 (M−1), 407.0 (M−1).

h) [(4-Bromo-7-hydroxy-3-phenyl-isothiazolo[4,5-c]pyridine-6-carbonyl)-amino]-acetic acid The title compound was synthesized in analogy to Example 1 from 4-bromo-7-hydroxy-3-phenyl-isothiazolo[4,5-c]pyridine-6-carboxylic acid butyl ester: MS (m/z) 406.0 (M−1), 408.0 (M−1).

Example 28

[(4-Hydroxy-3,7-dimethyl-isothiazolo[5,4-c]pyridine-5-carbonyl)-amino]-acetic acid a) 5-Methyl-[1,3,4]oxathiazol-2-one To a solution of acetamide (91.6 mmol) in toluene (183 mL) was added chlorocarbonylsulfenyl chloride (15.0 g, 114.5 mmol). The reaction mixture was allowed to stir at 100° C. for 4 h. After cooling to r.t., the reaction mixture was concentrated in vacuo. Distillation of the residue gave the desired product (4.44 g) at by 70-73° C. (30 Torr) as an oil.

b) 3-Methyl-isothiazole-4,5-dicarboxylic acid dimethyl ester

A solution of 5-Methyl-[1,3,4]oxathiazol-2-one (37.94 mmol) and dimethylacetylenedicarboxylate (75.89 mmol) in chlorobenzene (22.3 mL) was refluxed with stirring for 6 h before the mixture was concentrated in vacuo. Distillation of the residue gave the desired product (4.38 g) at by 100-105° C. (1.0 Torr) as an oil: MS (m/z) 216.0 (M+1).

c) 3-Methyl-isothiazole-4,5-dicarboxylic acid 5-methyl ester and 3-Methyl-isothiazole-4,5-dicarboxylic acid 4-methyl ester To a solution of 3-methyl-isothiazole-4,5-dicarboxylic acid dimethyl ester (20.37 mmol) in THF (19.7 mL) and MeOH (8.1 mL) was added 2N NaOH solution (10.18 mL). After the reaction mixture was stirred at r.t. for 90 min, it was partitioned between water and methyl 1-tert-butyl ether. The aqueous solution was acidified by addition of 1N HCl to pH=2, and extracted with EtOAc (3×100 mL). The combined organic layers were washed with brine and water, dried over $MgSO_4$, and concentrated in vacuo to give a mixture of the title compounds (3.74 g) as a yellow solid: MS (m/z) 202.0 (M+1).

d) N-(2-Methoxy-2-oxoethyl)-4-carbamoyl-3-methyl-isothiazole-5-carboxylic acid methyl ester and N-(2-Methoxy-2-oxoethyl)-5-carbamoyl-3-methyl-isothiazole-4-carboxylic acid methyl ester To a solution of the mixture of 3-methyl-isothiazole-4,5-dicarboxylic acid 5-methyl ester and 3-methyl-isothiazole-4,5-dicarboxylic acid 4-methyl ester (3.74 g, 18.6 mmol) described above in $CH_2Cl_2$ (46 mL) at 0° C. was added oxalyl chloride (37.21 mmol) and three drops of DMF. The reaction mixture was stirred at 0° C. for 5 min, then stirred at r.t. for 1 h, and concentrated in vacuo. To a solution of the resulting residue in $CH_2Cl_2$ (46 mL) was added glycine methyl ester hydrochloride (37.21 mmol) and $Et_3N$ (55.8 mmol) at 0° C. The reaction mixture was allowed to warm to r.t. overnight, and was then quenched with 0.5 N HCl (50 mL). The organic layer was washed with brine and water, dried over $MgSO_4$, and concentrated in vacuo. The residue was purified by flash column chromatography on silica gel. Eluting with 0-20% EtOAc/$CH_2Cl_2$ gave a mixture of the title compounds (4.38 g) as a yellow solid: MS (m/z) 273.1 (M+1).

e) 4,7-Dihydroxy-3-methyl-isothiazolo[5,4-c]pyridine-5-carboxylic acid butyl ester, 4,7-Dihydroxy-3-methyl-isothiazolo[4,5-c]pyridine-6-carboxylic acid butyl ester, 4,7-Dihydroxy-3-methyl-isothiazolo[5,4-c]pyridine-5-carboxylic acid methyl ester and 4,7-Dihydroxy-3-methyl-isothiazolo[4,5-c]pyridine-6-carboxylic acid methyl ester To a solution of the mixture of N-(2-methoxy-2-oxoethyl)-4-carbamoyl-3-methyl-isothiazole-5-carboxylic acid methyl ester and N-(2-methoxy-2-oxoethyl)-5-carbamoyl-3-methyl-isothiazole-4-carboxylic acid methyl ester (16.1 mmol) describe above in 1-BuOH (46 mL) was added sodium tert-butoxide (35.42 mmol). The reaction mixture was stirred at 110° C. for 50 min. After cooling to r.t., the mixture was acidified by addition of 1 N HCl to pH=2. The mixture was filtered and the filter cake washed with water (100 mL). The filter cake was then dissolved in $CH_2Cl_2$, the solution dried over $MgSO_4$ and concentrated in vacuo. The residue was purified by flash column chromatography on silica gel. Eluting with 0-20% EtOAc/$CH_2Cl_2$, gave a mixture of 4,7-dihydroxy-3-methyl-isothiazolo[5,4-c]pyridine-5-carboxylic acid butyl ester and 4,7-dihydroxy-3-methyl-isothiazolo[4,5-c]pyridine-6-carboxylic acid butyl ester (1.88 g) as a yellow solid: MS (m/z) 283.1 (M+1), and a mixture of 4,7-dihydroxy-3-methyl-isothiazolo[5,4-c]pyridine-5-carboxylic acid methyl ester and 4,7-dihydroxy-3-methyl-isothiazolo[4,5-c]pyridine-6-carboxylic acid methyl ester (400 mg) as a yellow solid: MS (m/z) 241.1 (M+1).

f) 7-Bromo-4-hydroxy-3-methyl-isothiazolo[5,4-c]pyridine-5-carboxylic acid butyl ester and 4-Bromo-7-hydroxy-3-methyl-isothiazolo[4,5-c]pyridine-6-carboxylic acid butyl ester To a solution of the mixture of 4,7-dihydroxy-3-methyl-isothiazolo[5,4-c]pyridine-5-carboxylic acid butyl ester and 4,7-dihydroxy-3-methyl-isothiazolo[4,5-c]pyridine-6-carboxylic acid butyl ester (6.67 mmol) obtained as described above in dichloroethane (33.3 mL) was added $POBr_3$ (8.0 mmol). The reaction mixture was stirred at 120° C. in a microwave oven for 35 min. After cooling to r.t., the mixture was partitioned between $CH_2Cl_2$ and sat. $NaHCO_3$, then filtered and the organic layer of the filtrate was washed with brine before it was dried over $MgSO_4$ and concentrated in vacuo. The residue was purified by flash column chromatography on silica gel. Eluting with 0-20% EtOAc/$CH_2Cl_2$, gave 7-bromo-4-hydroxy-3-methyl-isothiazolo[5,4-c]pyridine-5-carboxylic acid butyl ester (850 mg) as a white solid: MS (m/z) 342.9 (M−1), 345.0 (M−1), and 4-Bromo-7-hydroxy-3-methyl-isothiazolo[4,5-c]pyridine-6-carboxylic acid butyl ester (473 mg) as a white solid: MS (m/z) 342.9 (M−1), 345.0 (M−1).

g) 4-Hydroxy-3,7-dimethyl-isothiazolo[5,4-c]pyridine-5-carboxylic acid butyl ester To a solution of 7-bromo-4-hydroxy-3-methyl-isothiazolo[5,4-c]pyridine-5-carboxylic acid butyl ester (0.338 mmol) in DMF (2.05 mL) was added tetramethyltin (0.67 mmol) and $PdCl_2(PPh_3)_2$ (0.0338 mmol). The reaction mixture was stirred at 120° C. for 1 h. After cooling to r.t., the mixture was partitioned between water (100 mL) and EtOAc (100 mL). The organic layer was washed with brine and water, then dried over $MgSO_4$ and concentrated in vacuo. The residue was purified by flash column chromatography on silica gel. Eluting with 0-20% EtOAc/$CH_2Cl_2$, gave the title compound (38.1 mg) as a white solid: MS (m/z) 281.2 (M+1).

h) [(4-Hydroxy-3,7-dimethyl-isothiazolo[5,4-c]pyridine-5-carbonyl)-amino]-acetic acid The title compound was synthesized in analogy to Example 1 from 4-hydroxy-3,7-dimethyl-isothiazolo[5,4-c]pyridine-5-carboxylic acid butyl ester: MS (m/z) 282.1 (M+1).

Example 29

[(7-Hydroxy-3,4-dimethyl-isothiazolo[4,5-c]pyridine-6-carbonyl)-amino]-acetic acid a) 7-Hydroxy-3,4-dimethyl-isothiazolo[4,5-c]pyridine-6-carboxylic acid butyl ester The title compound was synthesized in analogy to Example 28 from 4-Bromo-7-hydroxy-3-methyl-isothiazolo[4,5-c]pyridine-6-carboxylic acid butyl ester: MS (m/z) 281.1 (M+1).

b) [(7-Hydroxy-3,4-dimethyl-isothiazolo[4,5-c]pyridine-6-carbonyl)-amino]-acetic acid The title compound was synthesized in analogy to Example 1 from 7-Hydroxy-3,4-dimethyl-isothiazolo[4,5-c]pyridine-6-carboxylic acid butyl ester: MS (m/z) 282.1 (M+1).

Example 30

[(4-Hydroxy-3-methyl-7-phenyl-isothiazolo[5,4-c]pyridine-5-carbonyl)-amino]-acetic acid a) 4-Hydroxy-3-methyl-7-phenyl-isothiazolo[5,4-c]pyridine-5-carboxylic acid butyl ester The title compound was synthesized in analogy to Example 1 from 7-Bromo-4-hydroxy-3-methyl-isothiazolo[5,4-c]pyridine-5-carboxylic acid butyl ester and phenyl boronic acid: MS (m/z) 343.1 (M+1).

b) [(4-Hydroxy-3-methyl-7-phenyl-isothiazolo[5,4-c]pyridine-5-carbonyl)-amino]-acetic acid The title compound was synthesized in analogy to Example 1 from 4-hydroxy-3-methyl-7-phenyl-isothiazolo[5,4-c]pyridine-5-carboxylic acid butyl ester: MS (m/z) 344.1 (M+1).

Example 31

[(7-Hydroxy-3-methyl-4-phenyl-isothiazolo[4,5-c]pyridine-6-carbonyl)-amino]-acetic acid a) 7-Hydroxy-3-methyl-4-phenyl-isothiazolo[4,5-c]pyridine-6-carboxylic acid butyl ester The title compound was synthesized in analogy to Example 1 from 4-Bromo-7-hydroxy-3-methyl-isothiazolo[4,5-c]pyridine-6-carboxylic acid butyl ester and phenyl boronic acid: MS (m/z) 343.1 (M+1).

b) [(7-Hydroxy-3-methyl-4-phenyl-isothiazolo[4,5-c]pyridine-6-carbonyl)-amino]-acetic acid The title compound was synthesized in analogy to Example 1 from 7-Hydroxy-3-methyl-4-phenyl-isothiazolo[4,5-c]pyridine-6-carboxylic acid butyl ester: MS (m/z) 344.1 (M+1).

Example 32

[(7-Hydroxy-3-methyl-isothiazolo[4,5-c]pyridine-6-carbonyl)-amino]-acetic acid a) 7-Hydroxy-3-methyl-isothiazolo[4,5-c]pyridine-6-carboxylic acid butyl ester A mixture of 4-Bromo-7-hydroxy-3-methyl-isothiazolo[4,5-c]pyridine-6-carboxylic acid butyl ester (0.19 mmol), 10% Pd/C (33 mg), ammonium formate (9.7 mmol), and EtOH/EtOAc (1:1, 1.9 mL) was refluxed with stirring for 4 h. After cooling to r.t. the mixture was filtered and the filtrate was concentrated in vacuo. The residue was purified by flash column chromatography on silica gel. Eluting with 0-20% EtOAc/CH$_2$Cl$_2$ gave the title compound (35.4 mg) as a white solid: MS (m/z) 267.2 (M+1).

b) [(7-Hydroxy-3-methyl-isothiazolo[4,5-c]pyridine-6-carbonyl)-amino]-acetic acid The title compound was synthesized in analogy to Example 1 from 7-Hydroxy-3-methyl-isothiazolo[4,5-c]pyridine-6-carboxylic acid butyl ester: MS (m/z) 268.1 (M+1).

Example 33

{[3-(2-Fluoro-phenyl)-4-hydroxy-isothiazolo[5,4-c]pyridine-5-carbonyl]-amino}-acetic acid a) 2-[Amino-(2-fluoro-phenyl)-methylene]-3-oxo-butyric acid ethyl ester The title compound was synthesized in analogy to Example 1 from 2-fluoro-benzonitrile and ethyl acetoacetate: MS (m/z) 252.2 (M+1).

b) 3-(2-Fluoro-phenyl)-5-methyl-isothiazole-4-carboxylic acid ethyl ester

The title compound was synthesized in analogy to Example 1 from 2-[amino-(2-fluoro-phenyl)-methylene]-3-oxo-butyric acid ethyl ester: MS (m/z) 266.1 (M+1).

c) N-(2,4-Dimethoxy-benzyl),N-(ethyl ethanylat-2-yl)-5-aminomethyl-3-(2-fluoro-phenyl)-isothiazole-4-carboxylic acid ethyl ester The title compound was synthesized in analogy to Example 1 from 3-(2-fluoro-phenyl)-5-methyl-isothiazole-4-carboxylic acid ethyl ester: MS (m/z) 517.3 (M+1).

d) 6-(2,4-Dimethoxy-benzyl)-3-(2-fluoro-phenyl)-4-oxo-4,5,6,7-tetrahydro-isothiazolo[5,4-c]pyridine-5-carboxylic acid ethyl ester The title compound was synthesized in analogy to Example 1 from N-(2,4-dimethoxy-benzyl),N-(ethyl ethanylat-2-yl)-5-aminomethyl-3-(2-fluoro-phenyl)-isothiazole-4-carboxylic acid ethyl ester: MS (m/z) 471.1 (M+1).

e) 3-(2-Fluoro-phenyl)-4-hydroxy-isothiazolo[5,4-c]pyridine-5-carboxylic acid ethyl ester The title compound was synthesized in analogy to Example 1 from 6-(2,4-dimethoxy-benzyl)-3-(2-fluoro-phenyl)-4-oxo-4,5,6,7-tetrahydro-isothiazolo[5,4-c]pyridine-5-carboxylic acid ethyl ester: MS (m/z) 319.1 (M+1).

f) {[3-(2-Fluoro-phenyl)-4-hydroxy-isothiazolo[5,4-c]pyridine-5-carbonyl]-amino}-acetic acid The title compound was synthesized in analogy to Example 1 from 3-(2-fluoro-phenyl)-4-hydroxy-isothiazolo[5,4-c]pyridine-5-carboxylic acid ethyl ester and glycine: MS (m/z) 348.1 (M+1).

Example 34

{[3-(2-Fluoro-phenyl)-4-hydroxy-7-phenyl-isothiazolo[5,4-c]pyridine-5-carbonyl]-amino}-acetic acid a) 7-Bromo-3-(2-fluoro-phenyl)-4-hydroxy-isothiazolo[5,4-c]pyridine-5-carboxylic acid ethyl ester The title compound was synthesized in analogy to Example 1 from 3-(2-fluoro-phenyl)-4-hydroxy-isothiazolo[5,4-c]pyridine-5-carboxylic acid ethyl ester: MS (m/z) 396.9 (M+1), 398.8 (M+1).

b) 3-(2-Fluoro-phenyl)-4-hydroxy-7-phenyl-isothiazolo[5,4-c]pyridine-5-carboxylic acid ethyl ester The title compound was synthesized in analogy to Example 1 from 7-Bromo-3-(2-fluoro-phenyl)-4-hydroxy-isothiazolo[5,4-c]pyridine-5-carboxylic acid ethyl ester and phenylboronic acid: MS (m/z) 395.1 (M+1).

c) {[3-(2-Fluoro-phenyl)-4-hydroxy-7-phenyl-isothiazolo[5,4-c]pyridine-5-carbonyl]-amino}-acetic acid The title compound was synthesized in analogy to Example 1 from 3-(2-fluoro-phenyl)-4-hydroxy-7-phenyl-isothiazolo[5,4-c]pyridine-5-carboxylic acid ethyl ester and glycine: MS (m/z) 422.0 (M−1).

Example 35

{[3-(2-Fluoro-phenyl)-4-hydroxy-7-(4-phenoxy-phenyl)-isothiazolo[5,4-c]pyridine-5-carbonyl]-amino}-acetic acid a) 3-(2-Fluoro-phenyl)-4-hydroxy-7-(4-phenoxy-phenyl)-isothiazolo[5,4-c]pyridine-5-carboxylic acid ethyl ester The title compound was synthesized in analogy Example 1 from 7-bromo-3-(2-fluoro-phenyl)-4-hydroxy-isothiazolo[5,4-c]pyridine-5-carboxylic acid ethyl ester and 4-phenoxyphenylboronic acid: MS (m/z) 487.1 (M+1).

b) {[3-(2-Fluoro-phenyl)-4-hydroxy-7-(4-phenoxy-phenyl)-isothiazolo[5,4-c]pyridine-5-carbonyl]-amino}-acetic acid The title compound was synthesized in analogy Example 1 from 3-(2-fluoro-phenyl)-4-hydroxy-7-(4-phenoxy-phenyl)-isothiazolo[5,4-c]pyridine-5-carboxylic acid ethyl ester and glycine: MS (m/z) 516.1 (M+1).

Example 36

{[3-(2-Fluoro-phenyl)-4-hydroxy-7-methyl-isothiazolo[5,4-c]pyridine-5-carbonyl]-amino}-acetic acid a) 3-(2-Fluoro-phenyl)-4-hydroxy-7-methyl-isothiazolo[5,4-c]pyridine-5-carboxylic acid ethyl ester The title compound was synthesized in analogy Example 28 from 7-bromo-3-(2-fluoro-phenyl)-4-hydroxy-isothiazolo[5,4-c]pyridine-5-carboxylic acid ethyl ester and tetramethyltin: MS (m/z) 333.2 (M+1).

b) {[3-(2-Fluoro-phenyl)-4-hydroxy-7-methyl-isothiazolo[5,4-c]pyridine-5-carbonyl]-amino}-acetic acid The title compound was synthesized in analogy Example 1 from 3-(2-fluoro-phenyl)-4-hydroxy-7-methyl-isothiazolo[5,4-c]pyridine-5-carboxylic acid ethyl ester and glycine: MS (m/z) 333.2 (M+1).

Example 37

[(4-Hydroxy-3-methyl-7-pyridin-3-yl-isothiazolo[5,4-c]pyridine-5-carbonyl)-amino]-acetic acid a) 4-Hydroxy-3-methyl-7-pyridin-3-yl-isothiazolo[5,4-c]pyridine-5-carboxylic acid butyl ester The title compound was synthesized in analogy Example 3 from 7-bromo-4-hydroxy-3-methyl-isothiazolo[5,4-c]pyridine-5-carboxylic acid butyl ester and 3-(tributylstannyl)pyridine: MS (m/z) 344.2 (M+1).

b) [(4-Hydroxy-3-methyl-7-pyridin-3-yl-isothiazolo[5,4-c]pyridine-5-carbonyl)-amino]-acetic acid The title compound was synthesized in analogy Example 1 from 4-hydroxy-3-methyl-7-pyridin-3-yl-isothiazolo[5,4-c]pyridine-5-carboxylic acid butyl ester and glycine: MS (m/z) 345.1 (M+1).

Example 38

[(4-Hydroxy-3-methyl-7-pyridin-2-yl-isothiazolo[5,4-c]pyridine-5-carbonyl)-amino]-acetic acid a) 4-Hydroxy-3-methyl-7-pyridin-2-yl-isothiazolo[5,4-c]pyridine-5-carboxylic acid butyl ester The title compound was synthesized in analogy Example 3 from 7-bromo-4-hydroxy-3-methyl-isothiazolo[5,4-c]pyridine-5-carboxylic acid butyl ester and 2-(tributylstannyl)pyridine: MS (m/z) 344.2 (M+1).

b) [(4-Hydroxy-3-methyl-7-pyridin-2-yl-isothiazolo[5,4-c]pyridine-5-carbonyl)-amino]-acetic acid The title compound was synthesized in analogy Example 1 from 4-hydroxy-3-methyl-7-pyridin-2-yl-isothiazolo[5,4-c]pyridine-5-carboxylic acid butyl ester and glycine: MS (m/z) 345.2 (M+1).

Example 39

[(7-Ethynyl-4-hydroxy-3-methyl-isothiazolo[5,4-c]pyridine-5-carbonyl)-amino]-acetic acid a) 4-Hydroxy-3-methyl-7-trimethylsilanylethynyl-isothiazolo[5,4-c]pyridine-5-carboxylic acid butyl ester The title compound was synthesized in analogy Example 6 from 7-bromo-4-hydroxy-3-methyl-isothiazolo[5,4-c]pyridine-5-carboxylic acid butyl ester and trimethylsilylacetylene: MS (m/z) 363.2 (M+1).

b) [(7-Ethynyl-4-hydroxy-3-methyl-isothiazolo[5,4-c]pyridine-5-carbonyl)-amino]-acetic acid The title compound was synthesized in analogy Example 1 from 4-hydroxy-3-methyl-7-trimethylsilanylethynyl-isothiazolo[5,4-c]pyridine-5-carboxylic acid butyl ester and glycine: MS (m/z) 290.1 (M−1).

Example 40

[(4-Hydroxy-3-methyl-7-pyrazin-2-yl-isothiazolo[5,4-c]pyridine-5-carbonyl)-amino]-acetic acid a) 4-Hydroxy-3-methyl-7-pyrazin-2-yl-isothiazolo[5,4-c]pyridine-5-carboxylic acid butyl ester The title compound was synthesized in analogy Example 3 from 7-bromo-4-hydroxy-3-methyl-isothiazolo[5,4-c]pyridine-5-carboxylic acid butyl ester and 2-(tributylstannyl)pyrazine: MS (m/z) 345.2 (M+1).

b) [(4-Hydroxy-3-methyl-7-pyrazin-2-yl-isothiazolo[5,4-c]pyridine-5-carbonyl)-amino]-acetic acid The title compound was synthesized in analogy Example 1 from 4-hydroxy-3-methyl-7-pyrazin-2-yl-isothiazolo[5,4-c]pyridine-5-carboxylic acid butyl ester and glycine: MS (m/z) 346.1 (M+1).

Example 41

[(7-Hydroxy-3-methyl-4-pyrazin-2-yl-isothiazolo[4,5-c]pyridine-6-carbonyl)-amino]-acetic acid a) 7-Hydroxy-3-methyl-4-pyrazin-2-yl-isothiazolo[4,5-c]pyridine-6-carboxylic acid butyl ester The title compound was synthesized in analogy Example 3 from 4-bromo-7-hydroxy-3-methyl-isothiazolo[4,5-c]pyridine-6-carboxylic acid butyl ester and 2-(tributylstannyl)pyrazine: MS (m/z) 345.2 (M+1)⁺.

b) [(7-Hydroxy-3-methyl-4-pyrazin-2-yl-isothiazolo[4,5-c]pyridine-6-carbonyl)-amino]-acetic acid The title compound was synthesized in analogy Example 3 from 7-hydroxy-3-methyl-4-pyrazin-2-yl-isothiazolo[4,5-c]pyridine-6-carboxylic acid butyl ester and glycine: MS (m/z) 346.1 (M+1).

Example 42

[(7-Hydroxy-3-indol-1-ylmethyl-4-phenyl-isothiazolo[4,5-c]pyridine-6-carbonyl)-amino]-acetic acid a) 7-Hydroxy-3-methyl-4-phenyl-isothiazolo[4,5-c]pyridine-6-carboxylic acid butyl ester The title compound was synthesized in analogy Example 3 from 4-Bromo-7-hydroxy-3-methyl-isothiazolo[4,5-c]pyridine-6-carboxylic acid butyl ester and tributylphenylstannane: MS (m/z) 343.1 (M+1).

b) 7-(2,2-Dimethyl-propionyloxy)-3-methyl-4-phenyl-isothiazolo[4,5-c]pyridine-6-carboxylic acid butyl ester A mixture of 7-Hydroxy-3-methyl-4-phenyl-isothiazolo[4,5-c]pyridine-6-carboxylic acid butyl ester (1.15 mmol), trimethylacetyl chloride (1.39 mmol), Et$_3$N (1.74 mmol), and CH$_2$Cl$_2$ (5.7 mL) was stirred at r.t. for 2 h. The mixture was then quenched with water and extracted with EtOAc (3×10 mL). The combined organic layers were washed with brine and water, dried over MgSO$_4$, and concentrated in vacuo. The residue was purified by flash chromatography on silica gel. Eluting with 0-20% EtOAc/CH$_2$Cl$_2$ gave the title compound (392.8 mg) as a colorless oil: MS (m/z) 427.2 (M+1).

c) 3-Bromomethyl-7-(2,2-dimethyl-propionyloxy)-4-phenyl-isothiazolo[4,5-c]pyridine-6-carboxylic acid butyl ester To a solution of 7-(2,2-dimethyl-propionyloxy)-3-methyl-4-phenyl-isothiazolo[4,5-c]pyridine-6-carboxylic acid butyl ester (392 mg) in CCl$_4$ (1.8 mL) was added N-bromosuccinimide (172 mg) and benzoyl peroxide (11.1 mg). The reaction mixture was refluxed for 18 h. After cooling to r.t. the mixture was filtered. The filtrate was concentrated in vacuo and purified by flash chromatography on silica gel. Eluting with 0-20% EtOAc/CH$_2$Cl$_2$ gave the title compound (398 mg) as a yellow oil: MS (m/z) 505.1 (M+1), 507.1 (M+1).

d) 7-Hydroxy-3-indol-1-ylmethyl-4-phenyl-isothiazolo[4,5-c]pyridine-6-carboxylic acid butyl ester To a solution of 3-bromomethyl-7-(2,2-dimethyl-propionyloxy)-4-phenyl-isothiazolo[4,5-c]pyridine-6-carboxylic acid butyl ester (86.1 mg) in DMF (0.85 mL) at 0° C. was added indole (39.9 mg) and 60% NaH (13.6 mg). The reaction mixture was allowed to warm up to r.t. and stirred for 2 h before water (20 mL) was added. The mixture was extracted with EtOAc (4×20 mL). The combined organic phases were washed with brine and water, dried over MgSO$_4$, and concentrated in vacuo. The residue was purified by flash chromatography on silica gel. Eluting with 1-50% EtOAc/hexanes gave the title compound (11 mg) as a white solid: MS (m/z) 458.2 (M+1).

e) [(7-Hydroxy-3-indol-1-ylmethyl-4-phenyl-isothiazolo[4,5-c]pyridine-6-carbonyl)-amino]-acetic acid The title compound was synthesized in analogy Example 1 from 7-hydroxy-3-indol-1-ylmethyl-4-phenyl-isothiazolo[4,5-c]pyridine-6-carboxylic acid butyl ester and glycine: MS (m/z) 459.1 (M+1).

Example 43

[(4-Hydroxy-3-phenyl-isothiazolo[5,4-c]pyridine-5-carbonyl)-amino]-acetic acid a) 2-(Amino-phenyl-methylene)-3-oxo-butyric acid methyl ester The title compound was synthesized in analogy Example 1 from benzonitrile: $^1$H NMR (CDCl$_3$, 200 MHz): δ=11.0 (br s, 1H), 7.43 (m, 5H), 5.50 (br s, 1H), 3.28 (s, 3H), 2.37 (s, 3H); MS: (+) m/z 220.36 (M+H$^+$).

b) 5-Methyl-3-phenyl-isothiazole-4-carboxylic acid methyl ester

A mixture of 2-(amino-phenyl-methylene)-3-oxo-butyric acid methyl ester (4.48 mmol), phosphorus pentasulfide (13.43 mmol), chloranil (4.48 mmol), and toluene was refluxed for 15 minutes before it was cooled to room temperature and filtered. The filtrate was concentrated and the residue was purified by flash column chromatography with a gradient of ethyl acetate and hexanes on silica gel (40 g) to give the title compound as a red oil (445 mg); $^1$H NMR (CDCl$_3$, 200 MHz): δ=7.51 (m, 2H), 7.42 (m, 3H), 3.75 (s, 3H), 2.74 (s, 3H); MS: (+) m/z 224.32 (M+H$^+$).

c) 5-Bromomethyl-3-phenyl-isothiazole-4-carboxylic acid methyl ester

Prepared in analogy to Example 1 from 5-methyl-3-phenyl-isothiazole-4-carboxylic acid methyl ester; MS (m/z): 312.18, 314.18 (M+H$^+$, $^{79}$Br/$^{81}$Br).

d) N-(2,4-Dimethoxy-benzyl),N-(ethyl ethanylat-2-yl)-5-aminomethyl-3-phenyl-isothiazole-4-carboxylic acid methyl ester Prepared in analogy to Example 1 from 5-bromomethyl-3-phenyl-isothiazole-4-carboxylic acid methyl ester; MS (m/z): 485.32 (M+H$^+$).

e) 4-Hydroxy-3-phenyl-isothiazolo[5,4-c]pyridine-5-carboxylic acid ethyl ester

Prepared in analogy to Example 1 from N-(2,4-dimethoxy-benzyl),N-(ethyl ethanylat-2-yl)-5-aminomethyl-3-phenyl-isothiazole-4-carboxylic acid methyl ester: MS (m/z): 301.30 (M+H$^+$).

f) [(4-Hydroxy-3-phenyl-isothiazolo[5,4-c]pyridine-5-carbonyl)-amino]-acetic acid Prepared in analogy to Example 1 from 4-hydroxy-3-phenyl-isothiazolo[5,4-c]pyridine-5-carboxylic acid ethyl ester and glycine; MS (m/z): 330.09 (M+H$^+$).

Example 44

[(4-Hydroxy-7-methyl-3-phenyl-isothiazolo[5,4-c]pyridine-5-carbonyl)-amino]-acetic acid a) 4-Hydroxy-7-methyl-3-phenyl-isothiazolo[5,4-c]pyridine-5-carboxylic acid ethyl ester Prepared in analogy to Example 36 from 7-bromo-4-hydroxy-3-phenyl-isothiazolo[5,4-c]pyridine-5-carboxylic acid ethyl ester and tetramethyltin; MS (m/z): 315.32 (M+H$^+$).

b) [(4-Hydroxy-7-methyl-3-phenyl-isothiazolo[5,4-c]pyridine-5-carbonyl)-amino]-acetic acid Prepared in analogy to Example 1 from 4-hydroxy-7-methyl-3-phenyl-isothiazolo[5,4-c]pyridine-5-carboxylic acid ethyl ester; MS (m/z): 344.32 (M+H$^+$).

Example 45

[(4-Hydroxy-3,7-diphenyl-isothiazolo[5,4-c]pyridine-5-carbonyl)-amino]-acetic acid a) 4-Hydroxy-3,7-diphenyl-isothiazolo[5,4-c]pyridine-5-carboxylic acid methyl ester Prepared in analogy to Example 1 from 7-bromo-4-hydroxy-3-phenyl-isothiazolo[5,4-c]pyridine-5-carboxylic acid ethyl ester; MS (m/z): 363.31 (M+H$^+$).

b) [(4-Hydroxy-3,7-diphenyl-isothiazolo[5,4-c]pyridine-5-carbonyl)-amino]-acetic acid Prepared in analogy to Example 1 from 4-hydroxy-3,7-diphenyl-isothiazolo[5,4-c]pyridine-5-carboxylic acid methyl ester and phenylboronic acid; MS (m/z): 406.27 (M+H$^+$).

Example 46

[(7-Ethyl-4-hydroxy-3-methyl-isothiazolo[5,4-c]pyridine-5-carbonyl)-amino]-acetic acid a) 7-Ethyl-4-hydroxy-3-methyl-isothiazolo[5,4-c]pyridine-5-carboxylic acid butyl ester The title compound was synthesized in analogy to Example 28 from 7-bromo-4-hydroxy-3-methyl-isothiazolo[5,4-c]pyridine-5-carboxylic acid butyl ester and tetraethyltin: MS (m/z) 295.2 (M+1).

b) [(7-Ethyl-4-hydroxy-3-methyl-isothiazolo[5,4-c]pyridine-5-carbonyl)-amino]-acetic acid The title compound was synthesized in analogy to Example 1 from 7-Ethyl-4-hydroxy-3-methyl-isothiazolo[5,4-c]pyridine-5-carboxylic acid butyl ester and glycine: MS (m/z) 296.2 (M+1).

Example 47

[(4-Ethyl-7-hydroxy-3-methyl-isothiazolo[4,5-c]pyridine-6-carbonyl)-amino]-acetic acid a) 4-Ethyl-7-hydroxy-3-methyl-isothiazolo[4,5-c]pyridine-6-carboxylic acid butyl ester The title compound was synthesized in analogy to Example 28 from 4-bromo-7-hydroxy-3-methyl-isothiazolo[4,5-c]pyridine-6-carboxylic acid butyl ester and tetraethyltin: MS (m/z) 295.2 (M+1).

b) [(4-Ethyl-7-hydroxy-3-methyl-isothiazolo[4,5-c]pyridine-6-carbonyl)-amino]-acetic acid The title compound was synthesized in analogy to Example 1 from 4-ethyl-7-hydroxy-3-methyl-isothiazolo[4,5-c]pyridine-6-carboxylic acid butyl ester and glycine: MS (m/z) 296.2 (M+1).

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A method of treating or delaying onset of anemia, the method comprising administering to a patient in need thereof a therapeutically effective amount of a compound of Formula I or II:

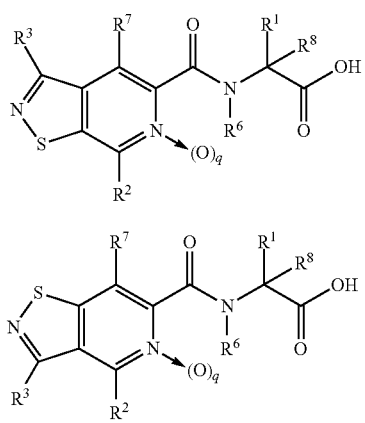

wherein q is 0 or 1;

$R^1$ is selected from the group consisting of hydrogen, deuterium, alkyl, and substituted alkyl;

$R^2$ is selected from the group consisting of hydrogen, hydroxyl, halo, cyano, alkyl, substituted alkyl, alkenyl, substituted alkenyl, alkynyl, substituted alkynyl, alkoxy, substituted alkoxy, cycloalkyl, substituted cycloalkyl, cycloalkoxy, substituted cycloalkoxy, amino, substituted amino, aminoacyl, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyloxy, substituted heterocyclyloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, and acyl;

$R^3$ is selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, aryl, substituted aryl, aryloxy, substituted aryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl;

$R^6$ is selected from the group consisting of hydrogen, alkyl, and substituted alkyl;

$R^7$ is selected from the group consisting of hydroxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, thio, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, amino, substituted amino, and acylamino; and $R^8$ is selected from the group consisting of hydrogen, deuterium, and methyl;

or a pharmaceutically acceptable salt, single stereoisomer, mixture of stereoisomers, ester, or amide thereof.

2. The method of claim 1, wherein q is 0.

3. The method of claim 1, wherein $R^1$ is hydrogen or alkyl.

4. The method of claim 1, wherein $R^6$ and $R^8$ are hydrogen.

5. The method of claim 1, wherein $R^2$ is selected from the group consisting of hydrogen, hydroxyl, halo, cyano, alkyl, substituted alkyl, alkynyl, aryl, substituted aryl, heteroaryl, substituted heteroaryl, and acyl.

6. The method of claim 1, wherein $R^3$ is alkyl, substituted alkyl, aryl or substituted aryl.

7. The method of claim 1, wherein $R^7$ is hydroxy.

8. The method of claim 1, wherein $R^1$ is hydrogen or alkyl;

$R^6$ and $R^8$ are hydrogen;

$R^2$ is selected from the group consisting of hydrogen, hydroxyl, halo, cyano, alkyl, substituted alkyl, alkynyl, aryl, substituted aryl, heteroaryl, substituted heteroaryl, and acyl;

$R^3$ is alkyl, substituted alkyl, aryl or substituted aryl; and $R^7$ is hydroxy.

9. The method of claim 1, wherein $R^1$ is hydrogen or methyl;

$R^6$ and $R^8$ are hydrogen;

$R^2$ is selected from the group consisting of hydrogen, hydroxyl, bromo, cyano, methyl, ethyl, benzyl, trifluoromethyl, ethynyl, phenyl, naphthalene-1-yl, 4-cyanophenyl, 4-fluorophenyl, 3-methoxyphenyl, 4-methoxyphenyl, 4-phenoxyphenyl, pyrid-2-yl, pyrid-3-yl, pyrid-4-yl, pyrazin-2-yl, 6-methoxypyridin-3-yl, 1-benzyl-1H-[1,2,3]triazol-4-yl, and acetyl;

$R^3$ is methyl, indol-1-ylmethyl, phenyl, 2-fluorophenyl, 4-fluorophenyl, or 4-chlorophenyl; and $R^7$ is hydroxy.

10. A method of treating or delaying onset of anemia, the method comprising administering to a patient in need thereof a therapeutically effective amount of a compound selected from the group consisting of {[7-(4-Fluoro-phenyl)-4-hydroxy-3-phenyl-isothiazolo[5,4-c]pyridine-5-carbonyl]-amino}-acetic acid; {[4-Hydroxy-7-(4-methoxy-phenyl)-3-phenyl-isothiazolo[5,4-c]pyridine-5-carbonyl]-amino}-acetic acid; [(4-Hydroxy-3-phenyl-7-pyridin-3-yl-isothiazolo[5,4-c]pyridine-5-carbonyl)-amino]-acetic acid; [(4-Hydroxy-3-phenyl-7-pyridin-2-yl-isothiazolo[5,4-c]pyridine-5-carbonyl)-amino]-acetic acid; [(4-Hydroxy-3-phenyl-7-pyridin-4-yl-isothiazolo[5,4-c]pyridine-5-carbonyl)-amino]-acetic acid; {[7-Ethynyl-3-(4-fluoro-phenyl)-4-hydroxy-isothiazolo[5,4-c]pyridine-5-carbonyl]-amino}-acetic acid; {[7-Bromo-3-(4-fluoro-phenyl)-4-hydroxy-isothiazolo[5,4-c]pyridine-5-carbonyl]-amino}-acetic acid; {[7-Cyano-3-(4-fluoro-phenyl)-4-hydroxy-isothiazolo[5,4-c]pyridine-5-carbonyl]-amino}-acetic acid; {[3-(4-Fluoro-phenyl)-4-hydroxy-7-methyl-isothiazolo[5,4-c]pyridine-5-carbonyl]-amino}-acetic acid; {[3-(4-Fluoro-phenyl)-4-hydroxy-7-phenyl-isothiazolo[5,4-c]pyridine-5-carbonyl]-amino}-acetic acid; {[7-(4-Cyano-phenyl)-3-(4-fluoro-phenyl)-4-hydroxy-isothiazolo[5,4-c]pyridine-5-carbonyl]-amino}-acetic acid; {[3-(4-Fluoro-phenyl)-4-hydroxy-isothiazolo[5,4-c]pyridine-5-carbonyl]-amino}-acetic acid; {[3-(4-Chloro-phenyl)-4-hydroxy-7-(4-methoxy-phenyl)- isothiazolo[5,4-c]pyridine-5-carbonyl]-amino}-acetic acid; {[3-(4-Chloro-phenyl)-7-ethynyl-4-hydroxy-isothiazolo[5,4-c]pyridine-5-carbonyl]-amino}-acetic acid; {[3-(4-Chloro-phenyl)-4-hydroxy-7-methyl-isothiazolo[5,4-c]pyridine-5-carbonyl]-amino}-acetic acid; {[3-(4-Chloro-phenyl)-4-hydroxy-isothiazolo[5,4-c]pyridine-5-carbonyl]-amino}-acetic acid; {[3-(4-Chloro-phenyl)-4-hydroxy-7-phenyl-isothiazolo[5,4-c]pyridine-5-carbonyl]-amino}-acetic acid; (R)-2-{[3-(4-Chloro-phenyl)-4-hydroxy-isothiazolo[5,4-c]pyridine-5-carbonyl]-amino}-propionic acid; (S)-2-{[3-(4-Chloro-phenyl)-4-hydroxy-isothiazolo[5,4-c]pyridine-5-carbonyl]-amino}-propionic acid; {[3-(4-Chloro-phenyl)-4-hydroxy-7-(3-methoxy-phenyl)-isothiazolo[5,4-c]pyridine-5-carbonyl]-amino}-acetic acid; {[3-(4-Chloro-phenyl)-4-hydroxy-7-(6-methoxy-pyridin-3-yl)-isothiazolo[5,4-c]pyridine-5-carbonyl]-amino}-acetic acid; {[7-Benzyl-3-(4-chloro-phenyl)-4-hydroxy-isothiazolo[5,4-c]pyridine-5-carbonyl]-amino}-acetic acid; {[7-(1-Benzyl-1H-[1,2,3]triazol-4-yl)-3-(4-chloro-phenyl)-4-hydroxy-isothiazolo[5,4-c]pyridine-5-carbonyl]-amino}-acetic acid; {[3-(4-Chloro-phenyl)-4-hydroxy-7-naphthalen-1-yl-isothiazolo[5,4-c]pyridine-5-carbonyl]-amino}-acetic acid; {[7-Acetyl-3-(4-chloro-phenyl)-4-hydroxy-isothiazolo[5,4-c]pyridine-5-carbonyl]-amino}-acetic acid; {[3-(4-Chloro-phenyl)-4-hydroxy-7-trifluoromethyl-isothiazolo[5,4-c]pyridine-5-carbonyl]-amino}-acetic acid; [(4-Bromo-7-hydroxy-3-phenyl-isothiazolo[4,5-c]pyridine-6-carbonyl)-amino]-acetic acid; [(4-Hydroxy-3,7-dimethyl-isothiazolo[5,4-c]pyridine-5-carbonyl)-amino]-acetic acid; [(7-Hydroxy-3,4-dimethyl-isothiazolo[4,5-c]pyridine-6-carbonyl)-amino]-acetic acid; [(4-Hydroxy-3-methyl-7-phenyl-isothiazolo[5,4-c]pyridine-5-carbonyl)-amino]-acetic acid; [(7-Hydroxy-3-methyl-4-phenyl-isothiazolo[4,5-c]pyridine-6-carbonyl)-amino]-acetic acid; [(7-Hydroxy-3-methyl-isothiazolo[4,5-c]pyridine-6-carbonyl)-amino]-acetic acid; {[3-(2-Fluoro-phenyl)-4-hydroxy-isothiazolo[5,4-c]pyridine-5-carbonyl]-amino}-acetic acid; {[3-(2-Fluoro-phenyl)-4-hydroxy-7-phenyl-isothiazolo[5,4-c]pyridine-5-carbonyl]-amino}-acetic acid; {[3-(2-Fluoro-phenyl)-4-hydroxy-7-(4-phenoxy-phenyl)-isothiazolo[5,4-c]pyridine-5-carbonyl]-amino}-acetic acid; {[3-(2-Fluoro-phenyl)-4-hydroxy-7-methyl-isothiazolo[5,4-c]pyridine-5-carbonyl]-amino}-acetic acid; [(4-Hydroxy-3-methyl-7-pyridin-3-yl-isothiazolo[5,4-c]pyridine-5-carbonyl)-amino]-acetic acid; [(4-Hydroxy-3-methyl-7-pyridin-2-yl-isothiazolo[5,4-c]pyridine-5-carbonyl)-amino]-acetic acid; [(7-Ethynyl-4-hydroxy-3-methyl-isothiazolo[5,4-c]pyridine-5-carbonyl)-amino]-acetic acid; [(4-Hydroxy-3-methyl-7-pyrazin-2-yl-isothiazolo[5,4-c]pyridine-5-carbonyl)-amino]-acetic acid; [(7-Hydroxy-3-methyl-4-pyrazin-2-yl-isothiazolo[4,5-c]pyridine-6-carbonyl)-amino]-acetic acid; [(7-Hydroxy-3-indol-1-ylmethyl-4-phenyl-isothiazolo[4,5-c]pyridine-6-carbonyl)-amino]-acetic acid; [(4-Hydroxy-3-phenyl-isothiazolo[5,4-c]pyridine-5-carbonyl)-amino]-acetic acid; [(4-Hydroxy-7-methyl-3-phenyl-isothiazolo[5,4-c]pyridine-5-carbonyl)-amino]-acetic acid; [(4-Hydroxy-3,7-diphenyl-isothiazolo[5,4-c]pyridine-5-carbonyl)-amino]-acetic acid; [(7-Ethyl-4-hydroxy-3-methyl-isothiazolo[5,4-c]pyridine-5-carbonyl)-amino]-acetic acid; and [(4-Ethyl-7-hydroxy-3-methyl-isothiazolo[4,5-c]pyridine-6-carbonyl)-amino]-acetic acid, or a pharmaceutically acceptable salt, single stereoisomer, mixture of stereoisomers, ester, or amide thereof.

11. The method of claim 1, wherein the compound is administered in a pharmaceutical composition comprising one or more compounds of claim 1 and a pharmaceutically acceptable excipient.

12. The method of claim 11, wherein the pharmaceutical composition further comprises at least one additional therapeutic agent selected from the group consisting of vitamin B12, folic acid, ferrous sulfate, recombinant human erythropoietin, and an erythropoiesis stimulating agent (ESA).

13. A method of inhibiting the activity of a HIF hydroxylase, the method comprising bringing into contact the HIF hydroxylase and an inhibitory-effective amount of a compound of Formula I or II:

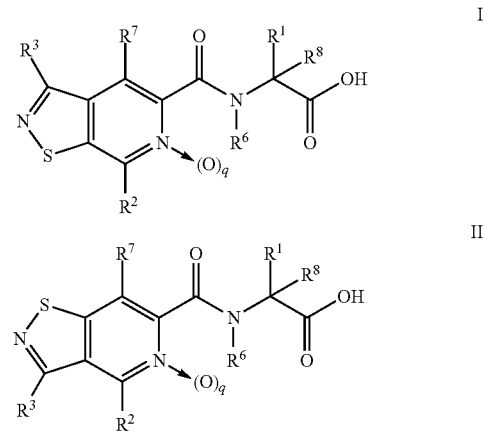

wherein
q is 0 or 1;
le is selected from the group consisting of hydrogen, deuterium, alkyl, and substituted alkyl;
$R^2$ is selected from the group consisting of hydrogen, hydroxyl, halo, cyano, alkyl, substituted alkyl, alkenyl, substituted alkenyl, alkynyl, substituted alkynyl, alkoxy, substituted alkoxy, cycloalkyl, substituted cycloalkyl, cycloalkoxy, substituted cycloalkoxy, amino, substituted amino, aminoacyl, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyloxy, substituted heterocyclyloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, and acyl;
$R^3$ is selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, aryl, substituted aryl, aryloxy, substituted aryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl;
$R^6$ is selected from the group consisting of hydrogen, alkyl, and substituted alkyl;
$R^7$ is selected from the group consisting of hydroxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, thio, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, amino, substituted amino, and acylamino; and
$R^8$ is selected from the group consisting of hydrogen, deuterium, and methyl;

or a pharmaceutically acceptable salt, single stereoisomer, mixture of stereoisomers, ester, or amide thereof.

14. The method of claim 13, wherein the HIF hydroxylase enzyme is an asparaginyl hydroxylase.

15. The method of claim 14, wherein the asparaginyl hydroxylase is factor inhibiting HIF.

16. The method of claim 13, wherein the HIF hydroxylase enzyme is a prolyl hydroxylase.

17. The method of claim 16, wherein the prolyl hydroxylase is selected from the group consisting of human EGLN1, EGLN2, and EGLN3.

* * * * *